US011324548B2

(12) United States Patent
Uhm et al.

(10) Patent No.: US 11,324,548 B2
(45) Date of Patent: May 10, 2022

(54) TRANSVASCULAR ELECTROSURGICAL DEVICES AND SYSTEMS AND METHODS OF USING THE SAME

(71) Applicant: Baylis Medical Company Inc., Montreal (CA)

(72) Inventors: Yun Uhm, Toronto (CA); Gareth Davies, Toronto (CA); Jason Woo, Mississauga (CA); Prateek Mathur, Toronto (CA)

(73) Assignee: Baylis Medical Company Inc., Mississauga (CA)

( * ) Notice: Subject to any disclaimer, the term of this patent is extended or adjusted under 35 U.S.C. 154(b) by 618 days.

(21) Appl. No.: 15/242,191

(22) Filed: Aug. 19, 2016

(65) Prior Publication Data
US 2017/0049511 A1 Feb. 23, 2017

Related U.S. Application Data

(60) Provisional application No. 62/208,404, filed on Aug. 21, 2015, provisional application No. 62/208,138, filed on Aug. 21, 2015.

(51) Int. Cl.
*A61B 18/14* (2006.01)
*A61B 18/00* (2006.01)
*A61B 17/00* (2006.01)

(52) U.S. Cl.
CPC .......... *A61B 18/1492* (2013.01); *A61B 2017/00026* (2013.01); *A61B 2018/00196* (2013.01);
(Continued)

(58) Field of Classification Search
CPC .......... A61B 18/1492; A61B 8/12; A61B 2017/00026; A61B 2218/007;
(Continued)

(56) References Cited

U.S. PATENT DOCUMENTS 5,830,222 A 11/1998 Makower
6,190,353 B1 * 2/2001 Makower ............. A61B 1/3137
604/95.01
(Continued)

FOREIGN PATENT DOCUMENTS

WO 2012068273 A1 5/2012

OTHER PUBLICATIONS

Tsauo, Jiaywei; Luo, Xuefeng; Ye, Linchao; Three-Dimensional Path Planning Software-Assisted Transjugular Intrahepatic Portosystemic Shunt: A Technical Modification, (Jun. 17, 2015), Cardiovasc Intervent Radiol. 38:742-746 https://doi.org/10.1007/S00270-014-0931-0.*
(Continued)

*Primary Examiner* — Jaymi E Della
*Assistant Examiner* — Sean W Collins
(74) *Attorney, Agent, or Firm* — Samuel Tekie; Glenn Arnold; Vincent Man

(57) ABSTRACT

A system, apparatus, and method of using the same are disclosed for carrying out a transvascular procedure such as a Transjugular Intrahepatic Portosystemic Shunt (TIPS) procedure using energy to create a tract between the hepatic vein and the portal vein. The present invention provides a flexible puncturing solution to effectively perform a transvascular procedure such as a TIPS procedure while minimizing damage to the liver and surrounding soft tissues or organs.

18 Claims, 25 Drawing Sheets

(52) U.S. Cl.
CPC ............... *A61B 2018/00404* (2013.01); *A61B 2018/00529* (2013.01); *A61B 2018/00642* (2013.01); *A61B 2018/144* (2013.01); *A61B 2218/007* (2013.01)

(58) Field of Classification Search
CPC .... A61B 2018/144; A61B 2018/00642; A61B 2018/00529; A61B 2018/00428; A61B 2018/00196
See application file for complete search history.

(56) References Cited

U.S. PATENT DOCUMENTS

| | | | | |
|---|---|---|---|---|
| 6,565,562 | B1* | 5/2003 | Shah | A61B 18/1492 128/898 |
| 6,726,677 | B1* | 4/2004 | Flaherty | A61B 1/3137 600/439 |
| 7,387,636 | B2 | 6/2008 | Cohn et al. | |
| 7,853,307 | B2 | 12/2010 | Edwards | |
| 8,628,491 | B2 | 1/2014 | Kahn et al. | |
| 8,632,468 | B2 | 1/2014 | Glossop et al. | |
| 8,753,366 | B2* | 6/2014 | Makower | A61B 8/12 606/185 |
| 8,951,276 | B2 | 2/2015 | Kellerman et al. | |
| 2004/0143262 | A1* | 7/2004 | Visram | A61B 18/1492 606/45 |
| 2008/0171934 | A1 | 7/2008 | Greenan et al. | |
| 2009/0118725 | A1* | 5/2009 | Auth | A61B 18/1492 606/33 |
| 2009/0198124 | A1 | 8/2009 | Adamus et al. | |
| 2010/0290693 | A1 | 11/2010 | Cohen et al. | |
| 2011/0208181 | A1 | 8/2011 | Habib | |
| 2012/0046657 | A1* | 2/2012 | Biadillah | A61B 18/1492 606/33 |
| 2012/0109079 | A1* | 5/2012 | Asleson | A61F 2/2427 604/272 |
| 2012/0179188 | A1* | 7/2012 | Chanduszko | A61B 17/3468 606/185 |
| 2016/0015422 | A1* | 1/2016 | De Cicco | A61B 17/3478 600/439 |

OTHER PUBLICATIONS

Harman, et al. Localization of the Portal Vein for Transjugular Catheterization: Percutaneous Placement of a Metallic Marker with Real-Time US Guidance. J. Vascular and Interventional Radiology, vol. 3, Iss. 3, Aug. 1992, pp. 545-547. doi.org/10.1016/S1051-0443(92)72010-7 (Year: 1992).*

* cited by examiner

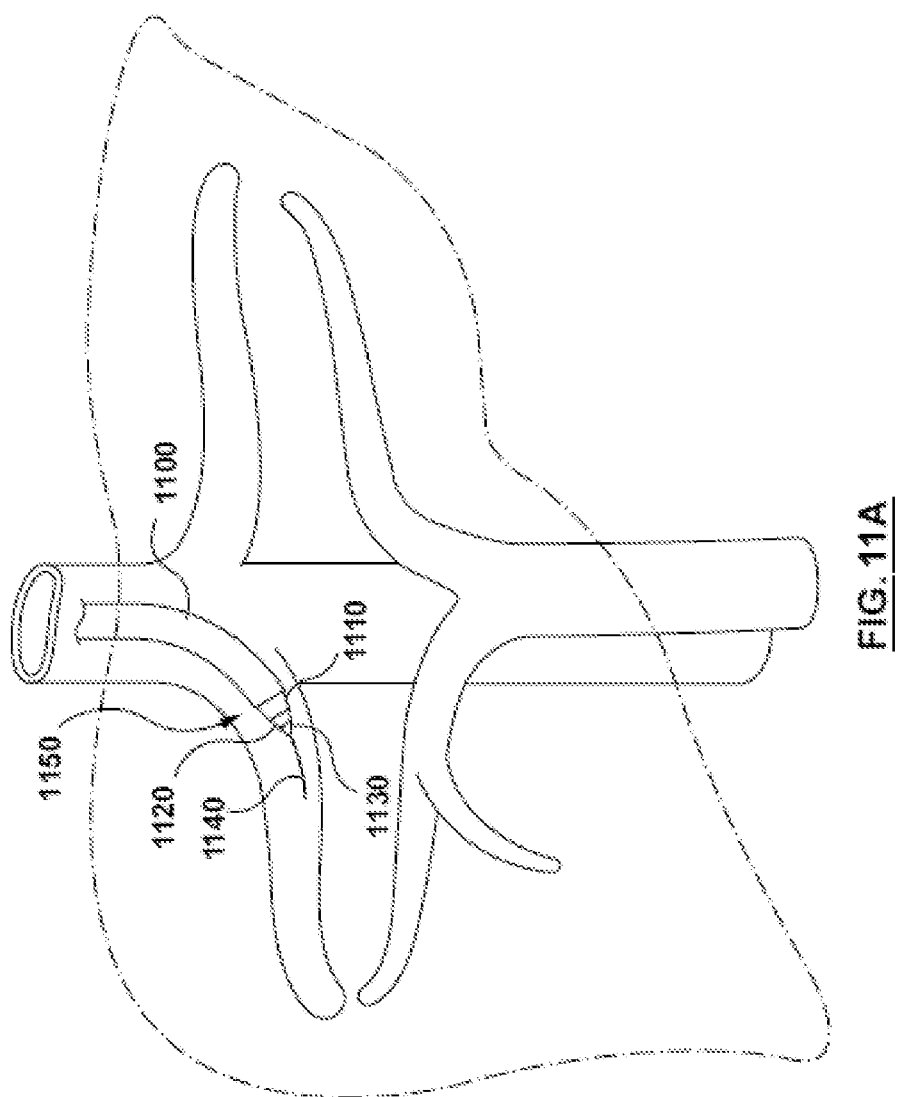

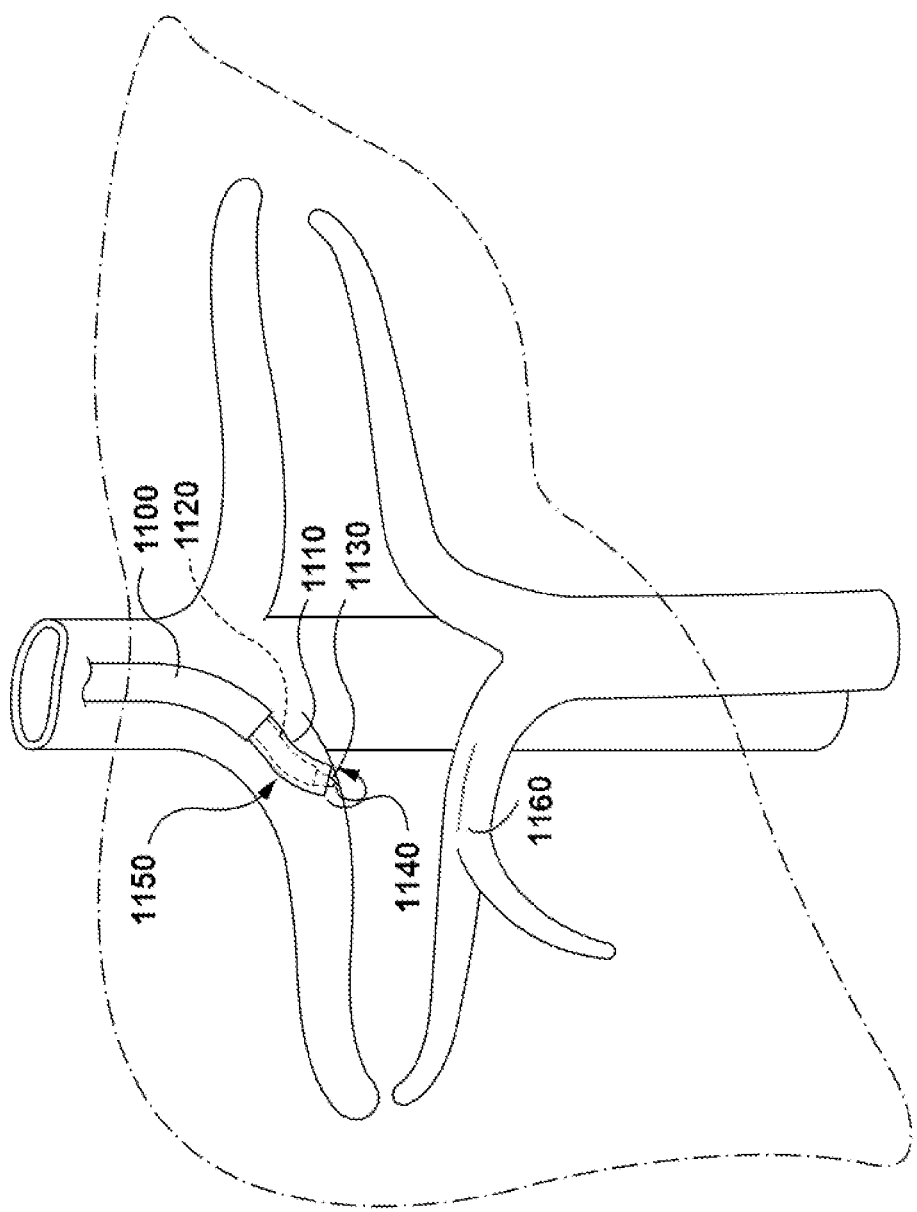

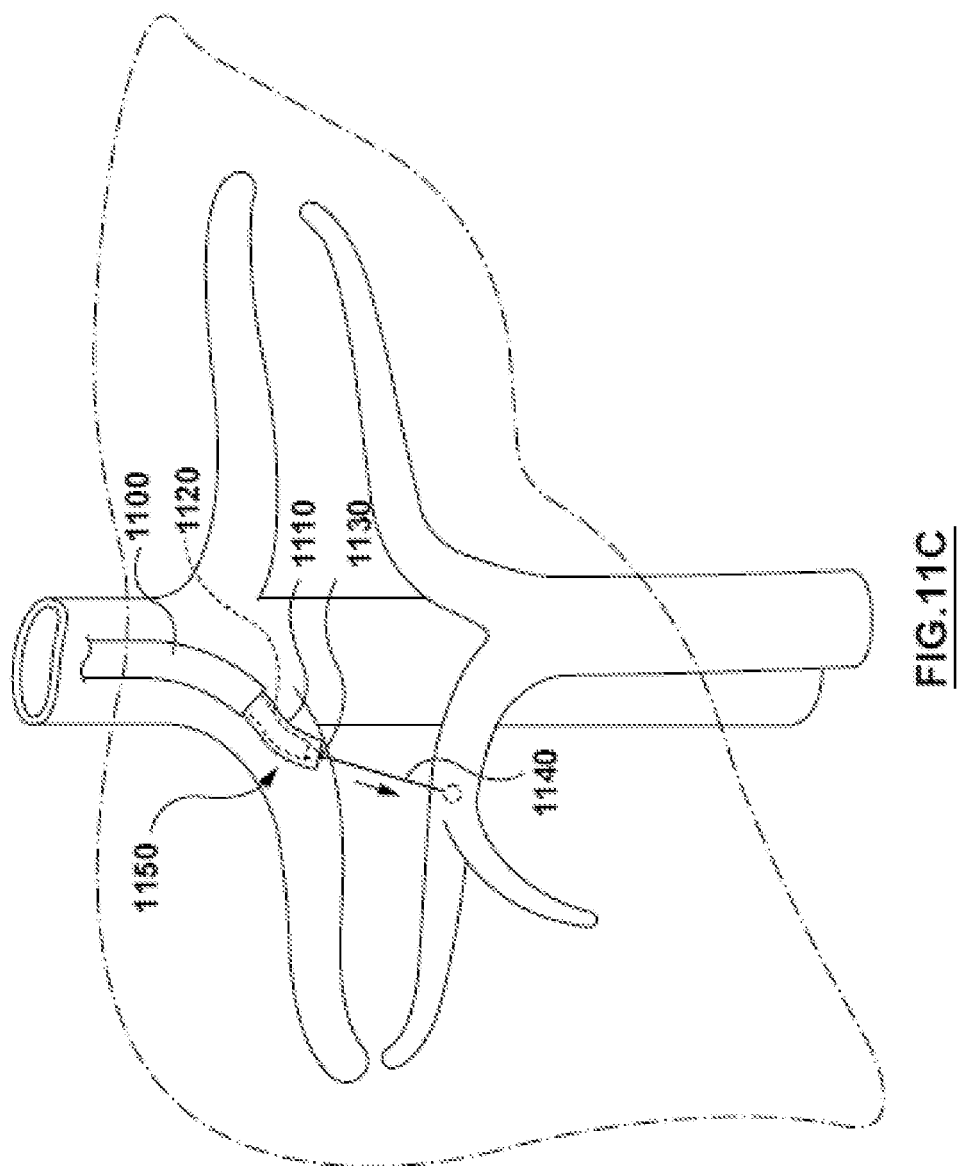

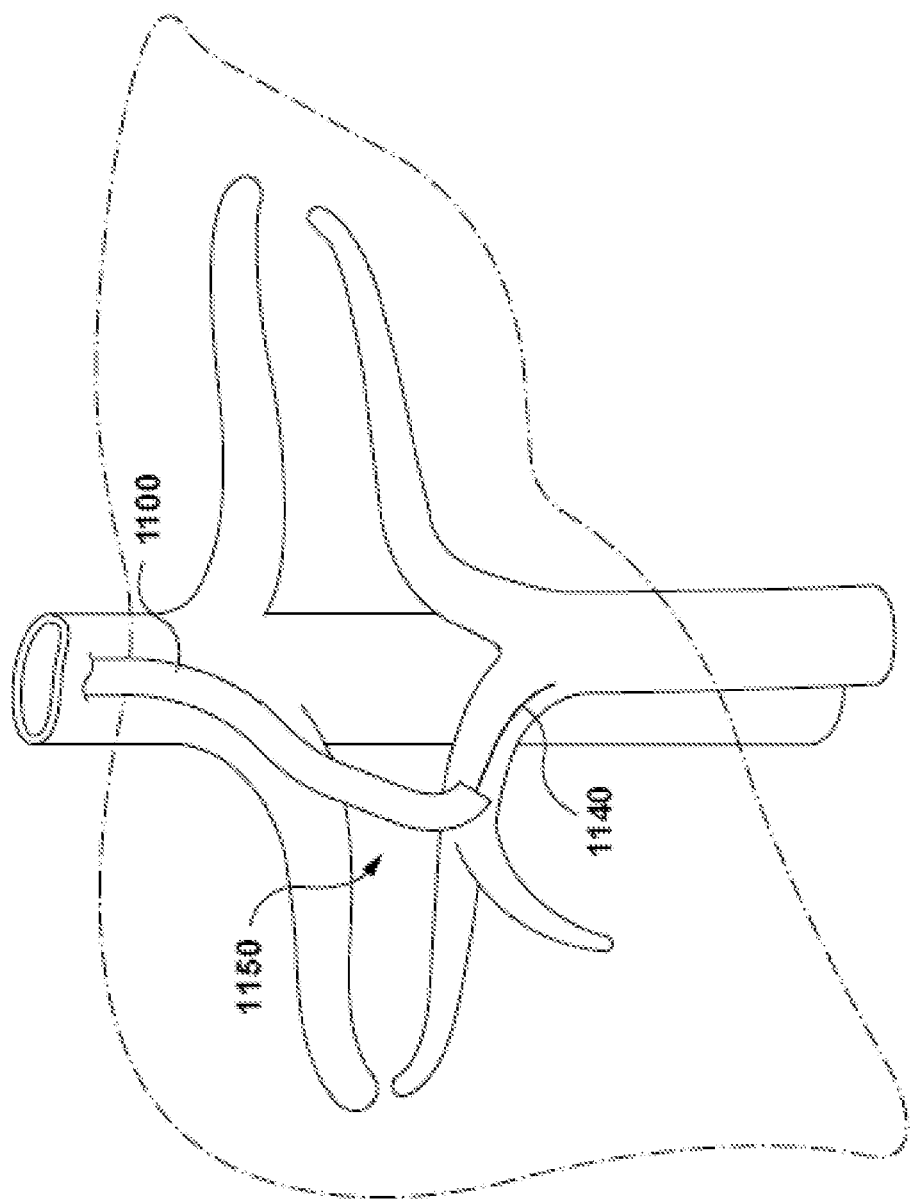

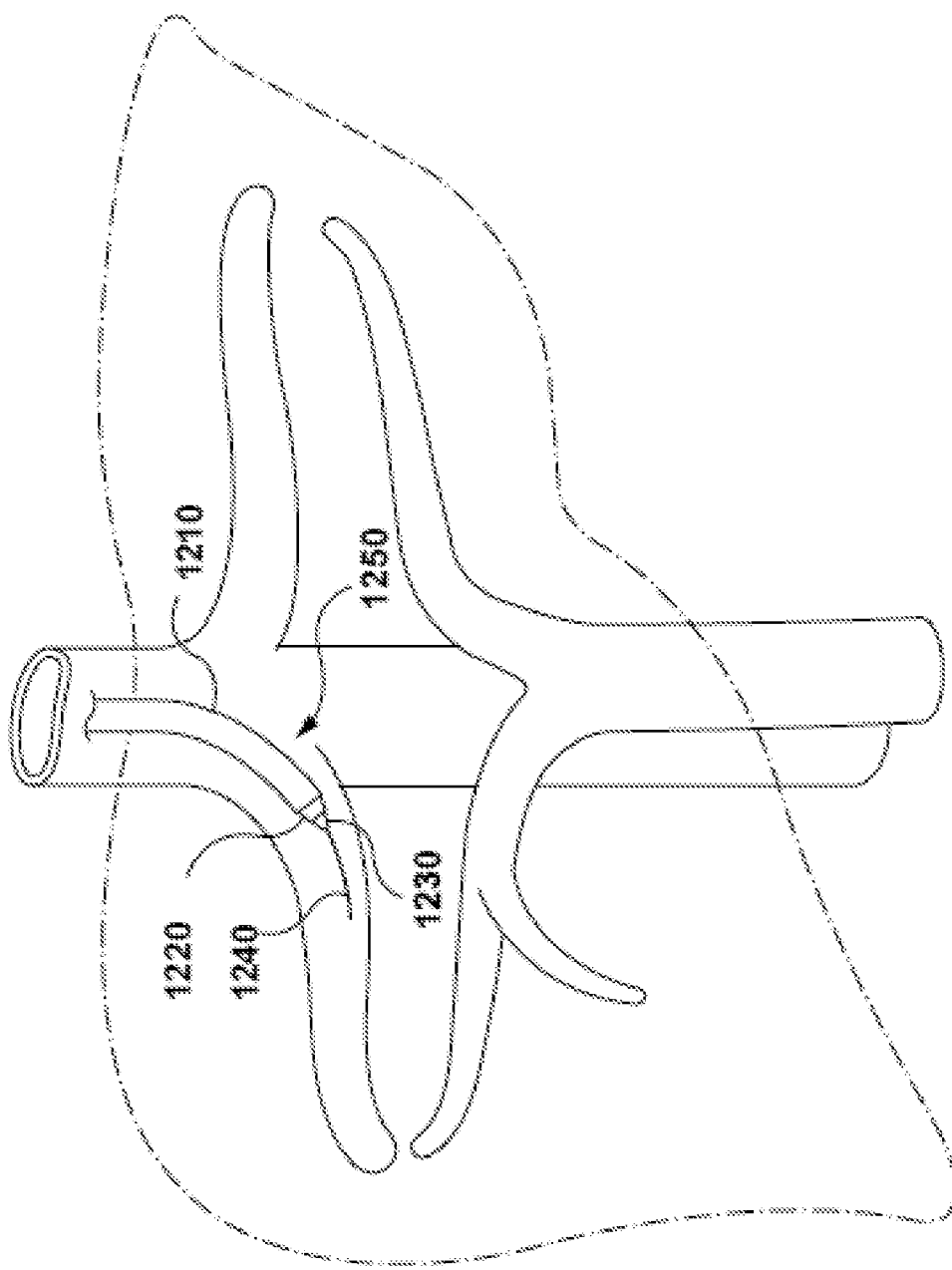

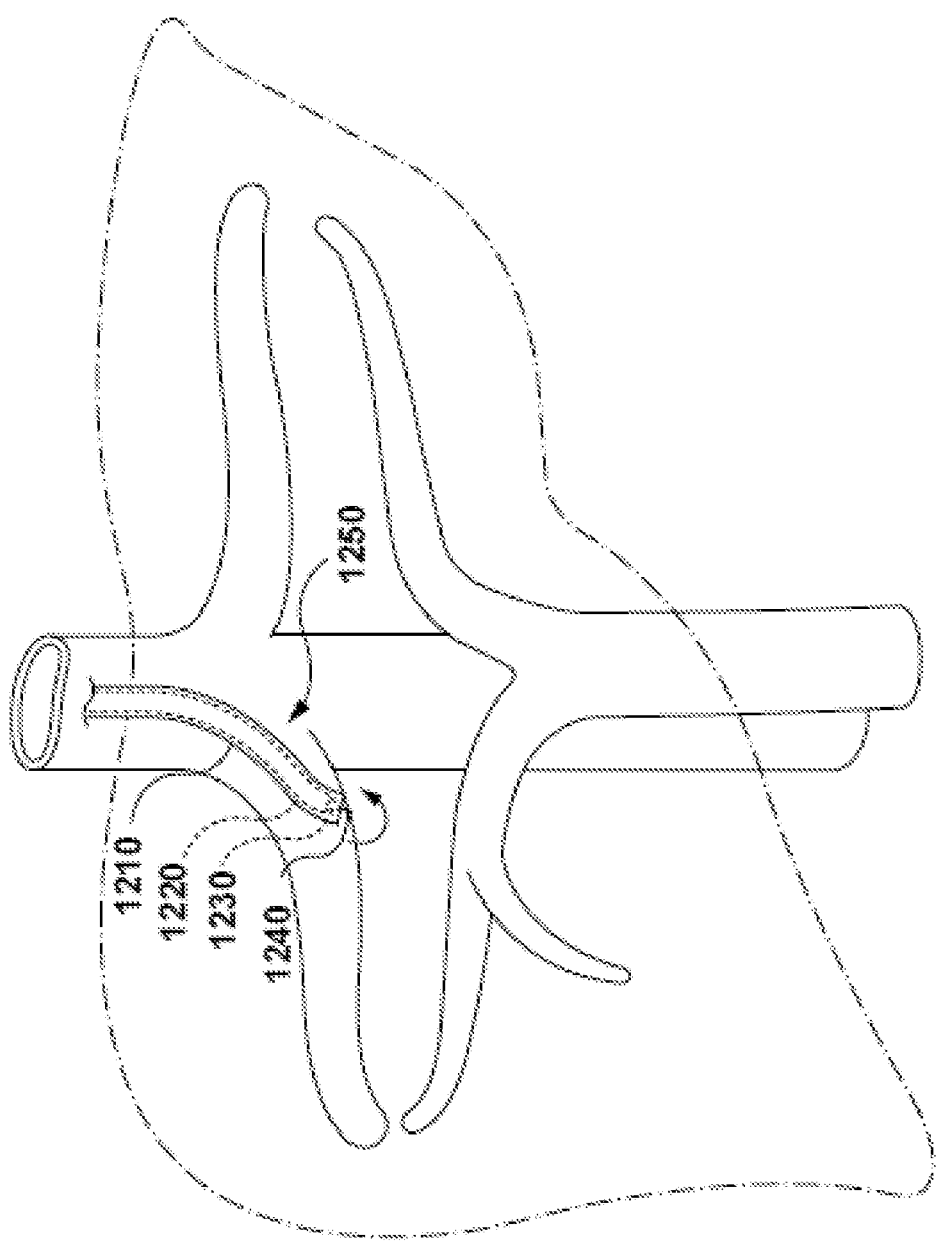

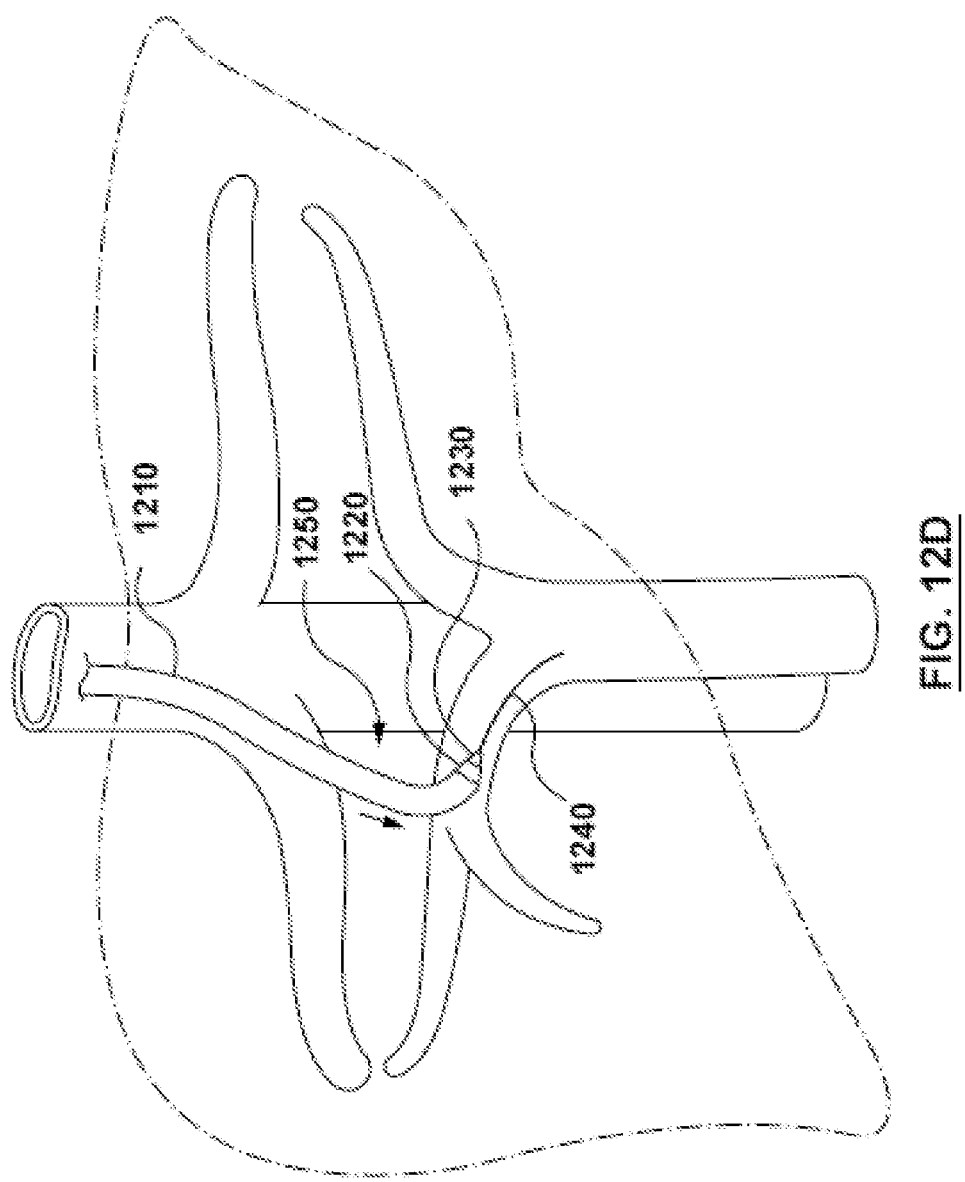

TRANSVASCULAR ELECTROSURGICAL DEVICES AND SYSTEMS AND METHODS OF USING THE SAME

CROSS-REFERENCES TO RELATED APPLICATIONS

This application claims benefit of U.S. Provisional Application Ser. No. 62/208,404, filed Aug. 21, 2015, and claims benefit of U.S. Provisional Application Ser. No. 62/208,138, filed Aug. 21, 2015, the disclosures of which are incorporated herein by reference in their entirety.

TECHNICAL FIELD

The disclosure relates to methods for reducing portal hypertension. More specifically, the disclosure relates to methods for reducing portal hypertension by creating a Transvascular Shunt such as Transjugular Intrahepatic Portosystemic Shunt [TIPS].

BRIEF DESCRIPTION OF THE DRAWINGS

In order that the invention may be readily understood, embodiments of the invention are illustrated by way of examples in the accompanying drawings, in which:

FIGS. 11A-11E disclose a method of facilitating a TIPS procedure, in accordance with an embodiment of the present invention;

FIGS. 12A-12E disclose a method of facilitating a TIPS procedure, in accordance with another embodiment of the present invention.

DETAILED DESCRIPTION

Figure 1A:
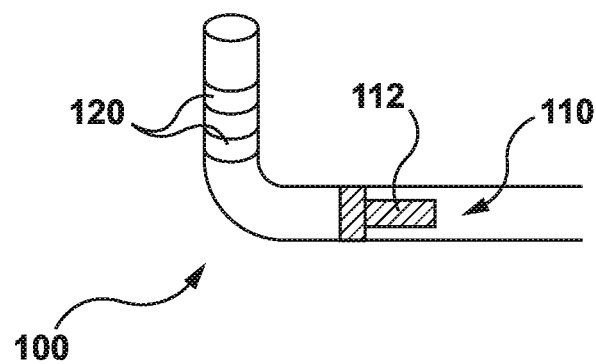
FIG. 1A is an illustration of an RF catheter and method of using the same in accordance with an embodiment of the present invention.

In accordance with an embodiment of the present invention, a method is disclosed for performing a TIPS procedure using a flexible RF device and a steerable sheath, the method comprising: aiming the flexible RF device under imaging by actively steering the steerable sheath to orient the flexible RF device along a trajectory from one vessel to another vessel located at a distance from the first; and delivering RF energy using the flexible RF device to puncture through to the second vessel to advance the RF device in a controlled manner while minimizing the force required to puncture through to the second vessel.

In an example of this broad aspect, the first vessel comprises a branch of the hepatic vein and the second vessel comprises a branch of the portal vein, wherein the step of aiming comprises actuating the steerable sheath, to angle the tip of the steerable sheath towards the portal vein. In one particular example, the step of aiming the steerable sheath towards the portal vein comprises angling the steerable sheath towards a target within the portal vein.

In another example of this broad aspect, the step of delivering energy comprises puncturing through a vessel wall of the hepatic vein, the liver parenchyma and a first vessel wall of the portal vein, wherein the risk of puncturing a second vessel wall of the portal vessel is minimized. Some embodiments of the present invention enable puncturing through a first vessel wall of the portal vein while avoiding puncturing a second vessel wall of the portal vein.

In a further example of this broad aspect, the flexible RF device is taken from the group comprising of a flexible RF guidewire, a flexible RF catheter, and a flexible RF guidewire catheter assembly.

In still another example, the step of aiming the flexible RF device under imaging comprises visualizing the portal vein. In a specific instance of this example, the step of imaging comprises: performing standard $CO_2$ angiography at the hepatic vein to visualize the portal vein under a first viewing plane; and rotating the fluoro to a second viewing plane which is the gun-barrel view plane; wherein a reference image of the portal vein is provided under the two viewing planes using $CO_2$ digital subtraction angiography to provide the physician with 3D information of the portal vein anatomy. In another instance of this example, the imaging technique comprises intravascular ultrasound (IVUS). In another instance of this example, the step of visualizing the portal vein comprises inserting a target device into the portal vein to assist in visualizing the portal vein.

In still another example of the broad aspect, a flexible RF guidewire and the steerable sheath are provided in a telescoping assembly. More specifically, as an example of this broad aspect, the flexible RF device comprises a flexible RF guidewire, and the flexible RF guidewire and the steerable sheath are provided in a telescoping assembly, wherein the step of aiming the flexible RF device comprises aiming the flexible RF guidewire within the telescoping assembly using the steerable sheath.

In another broad aspect, embodiments of the present invention provide a method of performing a TIPS procedure using a flexible RF device and a steerable sheath forming a telescoping assembly, the method comprising: aiming the telescoping assembly under imaging by actively steering the steerable sheath to orient the flexible RF device along a trajectory from one vessel to another vessel located at a distance from the first; and delivering RF energy and advancing the flexible RF device in a controlled manner to puncture through the liver tissue to create a channel between the first vessel and the second vessel, wherein application of RF energy minimizes the force required to traverse through the liver tissue, minimizing the risk of damage to vasculature and the liver tissue while reducing the need for device exchanges by reducing the number of required device exchanges in order to complete the procedure.

In an example of this broad aspect, the method additionally comprising a step of deploying a stent within the channel. In one example, the telescoping assembly additionally comprises a flexible dilator that is received within the steerable sheath, and a crossing catheter received therein, wherein the flexible RF guidewire is received within the crossing catheter. In a specific instance of this example, the telescoping assembly additionally comprises an introducer sheath, wherein the steerable sheath is received within the introducer sheath.

In an example of these broad aspects, the method additionally comprising a step of confirming portal vein access. In a specific instance of this example, the step of confirming portal access is taken from the group comprising of: aspirating through a catheter (such as a flexible RF catheter) and confirming if blood is withdrawn, injecting contrast and observing the vessel under imaging, and using tactile feedback.

In another instance of this example, the step of confirming portal access comprises inserting a target and assessing proximity to the target from the flexible RF puncturing device. In one such example, the target comprises a metal device that is inserted within the portal vein and using a 'metal contact' error from the RF generator as a confirmation feedback.

In an example of these broad aspects, the flexible RF device is advanced in a single step (in other words, in one step) to a desired distance or length. In an alternate example of these broad aspects, the flexible RF device is advanced in several (in other words two or more) discrete steps under the application of RF while confirming a trajectory under imaging.

In some individuals, portal hypertension (high blood pressure in the portal venous system of the liver) may occur, often due to disease progression in the liver. The portal venous system is formed by veins coming from the stomach, intestine, spleen, and pancreas merging into the portal vein. The portal vein branches into smaller vessels that permeate through the liver parenchyma, which cleanses the blood. The blood is then returned to system circulation via the hepatic vein which drains into the inferior vena cava.

High blood pressure may be observed in the portal venous system as a result of conditions such as disease within the venous systems itself, or disease within the liver tissue. For example, there may be an increase in blood pressure within the portal veins due to portal vein thrombosis or cirrhosis of the liver. Cirrhosis of the liver is a condition in which healthy liver tissue within the parenchyma of the liver is replaced with scar tissue. The scar tissue impacts liver function by slowing the processing of nutrients, hormones, and toxins, and may additionally block the flow of blood through the liver, resulting in an increase in blood pressure. As a result, there is a reduction in the volume of blood that leaves from the liver parenchyma into the hepatic vein and into the inferior vena cava, and a resulting increase in the volume of blood in the portal venous system supplying the liver, creating portal hypertension.

Portal hypertension may result in symptoms and complications that include variceal bleeding due to spontaneous rupture and hemorrhage from varices, accumulation of fluid in the abdomen (ascites), and hepatic encephalopathy which may result in confusion or forgetfulness due to inadequate liver function. Relief of portal hypertension may provide respite from symptoms resulting from the condition.

Conventional procedures to alleviate portal hypertension include methods and systems for creating a Transjugular Intrahepatic Portosystemic Shunt (TIPS). These procedures typically require a stiff or rigid needle or stylet to mechanically puncture through the liver in order to create a tract from the hepatic vein to the portal vein. Stiff needles or devices are used in the current solutions due to difficulties in traversing through tough liver tissue or vessel walls. The stiffness of the needle leads to difficulties in advancing and steering due to its inability to conform to tortuous anatomy. This can result in risk of damage to the liver or adjacent organs. Thus, there is a need in the art to provide a flexible solution that enables creation of a transvascular shunt such as TIPS while minimizing trauma to the involved organs.

Additionally, conventional procedures as noted above, use mechanical means to traverse through tough or cirrhotic livers. This may result in the use of excessive force due to the difficulties that may be observed while trying to advance the mechanical device. This may be particularly problematic when resistance is observed while attempting to advance the mechanical device such as a needle through the liver tissue, for example by pushing it. This may result in damage to the liver and/or other organs and vasculature. The present inventors have discovered that the use of radiofrequency (RF) energy to advance through difficult or tough liver tissue alleviates this problem by eliminating the need for applying excessive force in order to cross the tissue.

The present inventors have discovered a novel system and method for carrying out a transvascular procedure for creating transvascular pathways such as a TIPS procedure that uses radiofrequency technology to create a tract between the hepatic vein and the portal vein and enables the use of flexible devices for performing the procedure. Thus, embodiments of the present invention provides a flexible energy based (e.g. radiofrequency (RF)) solution to effectively perform a transvascular procedure such as a TIPS procedure while minimizing damage to the liver and surrounding soft tissues or organs. In some embodiments of the present invention, a flexible RF solution is provided. In other embodiments, other energy-based devices (e.g. optical, microwave or laser etc.) may also be used in embodiments of the present invention. Furthermore, embodiments of the present invention provides devices that use RF energy in order to puncture and traverse the tough tissues which allows for controlled advancement of the RF device without the need for applying excessive force.

In some embodiments, the present invention provides systems and methods for using RF puncture technology instead of mechanical puncturing means in order to create a tract between the hepatic vein and portal vein, which enables the use of flexible devices for carrying out transvascular procedures such as those for creating transvascular pathways, for example TIPS procedures. More specifically, a flexible RF catheter is provided that may be advanced to the hepatic vein from internal jugular access or femoral access. A series of flexible access devices may additionally be provided in order to guide the flexible RF catheter into the hepatic vein and to direct the flexible RF catheter from the hepatic vein towards the portal vein.

Figure 10:
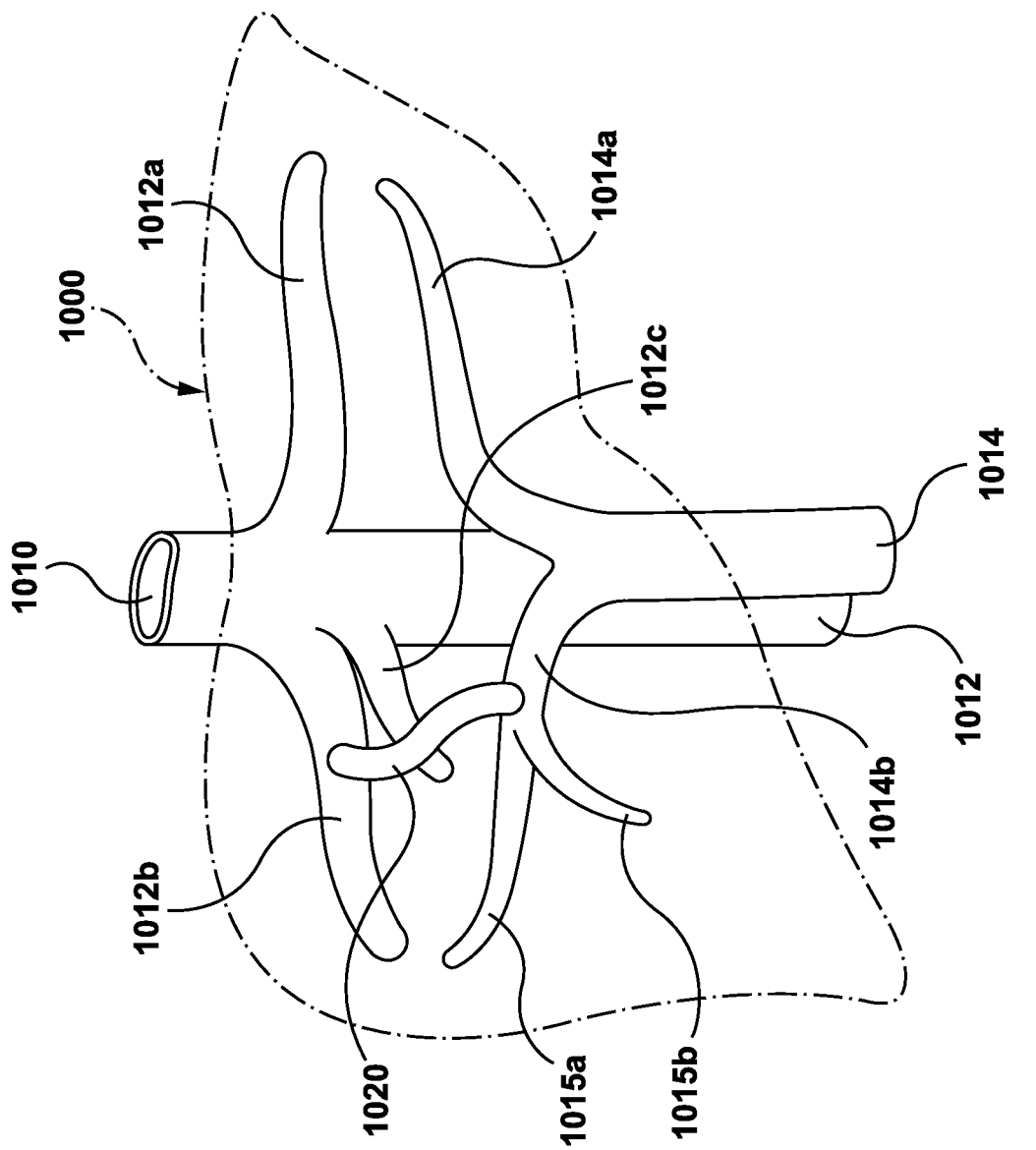
FIG. 10 is an illustration of the anatomy of a liver with the hepatic vein branches and the portal vein branches being shown and a pathway being shown being shown between two of them for placing a shunt there-between after creation of a tract in accordance with various embodiments of the present invention.

More specifically, the system of the present invention allows for positioning of the flexible RF catheter within the hepatic vein to provide a direct path towards the portal vein. Once positioned, the system allows for energy to be delivered from the RF catheter to puncture through the hepatic vessel wall, the liver parenchyma, and the portal vessel wall in order to access the portal vein. Specifically, FIG. 10 illustrates the liver 1000, and further illustrates the vascular anatomy of the liver. More, specifically, the inferior vena cava (IVC) 1010 is shown that branches into the hepatic vein 1012. The hepatic vein 1012 branches into the left hepatic vein 1012*a* and the right hepatic vein 1012*b*, and the middle hepatic vein 1012*c*. FIG. 10 additionally shows the portal vein 1014 that branches into the right portal vein 1014*b* and the left portal vein 1014*a*. The right portal vein 1014*b* then branches into the right lateral sectoral vein 1015*a* and the right medial sectoral vein 1015*b*.

In accordance with an additional broad embodiment of the present invention, a flexible RF puncture device is provided that may be advanced to the hepatic vein from an internal jugular access or femoral access to create a tract or passage there-between. In some embodiments the tract or channel may be created between a branch of the hepatic vein and a branch of the portal vein or any variation there-between. Anatomy of the liver is shown in FIG. 10 of the disclosure which illustrates the hepatic and the portal veins.

In some embodiments of a method and system of the present invention, a steerable sheath is provided for navigating through tortuous anatomy and aiming/directing the flexible RF puncture device. The steerable sheath allows for positioning and/or guidance of the flexible RF puncture device within the hepatic vein to provide a direct path from the hepatic vein towards the portal vein. Once the flexible RF puncture device positioned within the hepatic vein, the system allows for energy to be delivered from the flexible RF puncture device to puncture through the hepatic vessel wall, the liver parenchyma, and the portal vessel wall in order to access the portal vein. Additional flexible access devices may be provided to further assist with the procedure.

In one example, the flexible RF puncture device comprises an RF catheter. In another example, the flexible RF puncture device comprises an RF guidewire, or in other words, an RF wire. In some such examples, an RF guidewire is provided that is usable with a support catheter. The RF guidewire and support catheter can be coupled together to form an RF guidewire catheter assembly. The RF guidewire catheter assembly may be usable with a steerable sheath. In one example, methods and systems are provided that comprise device combinations that have desired compatibility and torqueability.

The use of a steerable sheath in certain embodiments provides further advantages over existing procedures. More specifically, the steerable sheath provides advantages relative to conventional stiff needles when advancing the steerable sheath into the hepatic vein. The flexible distal tip of the steerable sheath is capable of making the required turn(s) to navigate through the tortuous anatomy to enter deep into the vein, as opposed to a needle, which is capable of limited advancement into the vein due to its rigid curve. In some examples, the conventional rigid needles may advance by only about 1-2 cm into the hepatic vein. In some examples, the use of a flexible steerable sheath may allow the sheath (and/or the assembly including the sheath) to be advanced for about 2-5 cm into the hepatic vein. In other embodiments, the sheath and/or the assembly may be advanced to a distance greater than 5 cm. In some embodiments, the use of a steerable sheath also allows more flexibility in choosing the access site. For example, the flexible steerable sheath may allow for access through the femoral vein or the jugular vein. Additional advantages may be available through the use of the steerable sheath when aiming or guiding the puncture device. For example, the tip of the sheath is capable of being torqued and angled to substantially achieve the required position to aim substantially directly at the portal vein. As such, the steerable sheath functions to orient the assembly in a desired trajectory. A conventional stiff needle, on the other hand, typically includes a fixed angle or curve and may only be torqued, which may severely limit the options available to the physician for aiming or guiding the needle at/to the portal vein target.

Furthermore, puncturing using a flexible RF puncture device is advantageous as it allows for controlled advancement where the speed and depth of advancement can be controlled while incurring minimal resistance. A conventional stiff needle, on the other hand, is generally advanced in one swift push since mechanical puncture through cirrhotic tissue requires substantial force, which may result in injury or damage to the liver and/or adjacent organs or the vasculature.

Therefore, in accordance with embodiments of the present invention, methods and systems are disclosed that use RF energy to traverse from the hepatic vein to the portal vein. These embodiments additionally permit the use of flexible devices in conjunction with the use of radiofrequency energy in order to effectively perform transvascular procedures such as TIPS procedures while reducing the risk of damage to internal organs relative to use of conventional rigid devices and systems.

In accordance with certain embodiments of the present invention, apparatus and systems are disclosed for performing a transvascular procedure such as a TIPS procedure and methods for using the same. Some such embodiments enable a physician to effectively perform the TIPS procedure by using radiofrequency energy to create a tract from the hepatic vein to the portal vein through the liver while at the same time minimizing the risk of damage to the liver and other internal organs and/or vasculature by providing flexible devices and systems that conform to and/or may be atraumatically advanced through the internal anatomy and vasculature.

More specifically, in some embodiments, the device combination of the present invention provides enhanced steering or steerability to allow for in-situ adjustment in order to allow the physician to more accurately aim at a target location within the portal vein. In some such examples, the steerable sheath functions to orient the assembly along a predictable trajectory towards the target location. The assembly additionally uses radiofrequency RF energy to allow for controlled advancement through tissue, such as through a vessel wall of the hepatic vein, through the liver parenchyma and through a vessel wall of the portal vein, in order to minimize the force used and to minimize damage to the tissue. The assembly additionally minimizes torsion of the liver as less force is required to puncture through the liver. This may help ensure that the intended target location does not move under imaging as the liver moves. As such, the delivery of RF in a controlled manner may help maintain alignment of the assembly to the target location, for example at location along the portal vein, under imaging. Furthermore, the embodiments of the present invention provide a steerable solution to ensure effective aiming of the assembly.

In some such examples, the assembly of the present invention provides an additional advantage over conventional assemblies as a rigid needle that is inserted into a pre-curved device may result in relaxation of the curve before the needle reaches the intended target. Some embodiments of the present invention provide a steerable sheath is provided that is usable with a flexible RF device, such as an RF catheter or an RF guidewire, that provides an additional advantage over a rigid needle as it enables the steerable sheath to steer and orient the flexible RF device substantially without impeding the intended curvature of the steerable sheath to allow the steerable sheath to aim the assembly including the flexible RF device along an intended trajectory towards a target location within the portal vein. The embodiments presented herein the use of flexible devices and RF deliver may enable enhanced precision, and may additionally reduce the number of passes required in order to complete the procedure, and hence the time for completion of the procedure. The systems or assemblies disclosed herein provide additional advantages in terms of enabling the assembly to effectively aim at a hidden target using active steering to orient the device and to reach out and advance towards the hidden target using RF, both under image guidance. In some such examples, the assembly may traverse through about 1 cm to about 2 cm of the liver parenchyma from the hepatic vein to the portal vein. In some examples, the system provides for a flexible solution that uses RF that enables a TIPS procedure in a more controlled manner to puncture through the hepatic vessel wall, the liver tissue and may permit puncture through only a single vessel wall of the portal vein, eliminating the need for puncturing though both vessel walls of the portal vein, as required in conventional procedures, where the apparatus may then be retracted with aspiration to find out when the apparatus tip is within the portal vein again. Contrary to this, with some embodiments of the present invention, the portal vein may be accessed through a single puncture through a vessel wall of the portal vein, which my reduce the number of passes required in order to access the portal vein and hence may reduce the time required to complete the procedure. Thus, some embodiments of the present invention enable puncturing through a first vessel wall of the portal vein while avoiding puncturing a second vessel wall of the portal vein.

Additionally, in some embodiments of a present invention, a medical imaging method is provided for transvascular procedures. In one such example, a methods is provided for performing dual plane digital subtraction angiography (DSA) for facilitating a Transjugular Intrahepatic Portosystemic Shunt (TIPS) procedure.

As outlined herein above, a Transjugular Intrahepatic Portosystemic Shunt (TIPS) procedure may be used to alleviate portal hypertension. In conventional TIPS procedures, a large percentage of physicians may use carbon-dioxide ($CO_2$) digital subtraction angiography (DSA) to temporarily image or visualize vasculature of interest, such as the hepatic and portal veins. In one example, the $CO_2$ digital subtraction angiography may be used to visualize the portal vein. In such situations, the $CO_2$ may diffuse away quickly so the portal vein is only visible for a very short period of time. Digital subtraction angiography is performed to generate a reference image with the portal vein outlined. In such procedures, the position of the fluoroscopy (fluoro) machine needs to be fixed for the remainder of the procedure. The physician then performs the procedure based on 2D information of the anatomy. The current commonly used $CO_2$ angiography is done under one view (usually AP view), which does not provide 3D information of the anatomy. Thus, there is a need in the art to provide an improved imaging solution which provides the physician with greater or more detailed information of the anatomy.

Furthermore, in the conventional imaging techniques that are generally used for TIPS procedures, the fluoroscopic view cannot be changed once the portal vein target has been imaged. If the physician was to change the view, he/she would risk losing their reference, requiring them to redo the $CO_2$ imaging. Thus, there is an additional need in the art to provide an imaging solution that provides a physician with the flexibility of moving between multiple views.

The present inventors have discovered a novel method that provides an imaging solution that generates a reference image of the portal vein under two different viewing planes with $CO_2$ DSA. This method provides the physician with 3D information of the anatomy for carrying out a transvascular procedure such as a TIPS procedure, in addition to providing additional flexibility to the physician.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Flexible RF Catheter and a Guiding Catheter/Sheath Assembly

In accordance with an embodiment of the present invention, a flexible system is provided for performing or facilitating a transvascular intrahepatic procedure such as a TIPS procedure for creating a pathway between vasculature comprising a hepatic vein and a portal vein. The system comprises a flexible RF catheter and an angled guiding catheter or sheath, the angled guiding catheter or sheath having one or more directional markers, such as radiopaque bands, and one or more alignment markers, such as radiopaque bands. The method comprises the following steps: advancing the RF catheter to the hepatic vein from internal jugular access or femoral access; advancing the angled guiding catheter or sheath over the RF catheter; utilizing a 'gun-barrel' view from the portal vein to the hepatic vein under imaging such as fluoroscopy while steering the guiding catheter or sheath to direct the RF catheter towards the portal vein; delivering RF energy from the RF catheter to puncture through a hepatic vessel wall, the liver parenchyma and a portal vessel wall to access or enter the portal vein to form a channel or tract from the hepatic vein to the portal vein. In one such example, the angled guiding catheter functions to guide and aim the RF catheter from within the hepatic vein towards the portal vein to aim the RF catheter towards the portal vein, allowing the RF catheter to apply RF to puncture through the liver parenchyma tissue for creating a channel between the hepatic and portal veins with minimal force using RF while minimizing damage to the vasculature and the liver tissue. The method then comprises: confirming access into the portal vein; dilating the tract in the liver; and advancing a sheath, such as a 10 French sheath, through the tract to support the placement of a supportive device to keep the keep the tract open, such as a stent or similar device.

In some examples of the present embodiment, the method additionally provides for a step of confirming portal access. In some examples this may be done by aspirating through the RF catheter and confirming if blood is withdrawn. In other examples, access into the portal vein may be additionally confirmed by delivering or injecting contrast through the RF catheter. Alternatively, one can use a 'metal contact' error from the RF generator as a confirmation feedback. This is described in further detail herein below. Still in another example, tactile feedback such as wire feedback from a guidewire, RF guidewire or RF catheter may be used. The tactile feedback may be received once the guidewire or catheter enters the portal vein.

More specifically, in accordance with a detailed embodiment of the present invention, a system is provided for use in a transvascular procedure such as a TIPS procedure that comprises an RF catheter with an electrode at the distal end that punctures tissue upon delivery of RF energy in a controllable manner to create a tract through the liver parenchyma from the hepatic vein to the portal vein. The catheter additionally defines a lumen there-through and comprises a side port to enable delivery of contrast injection or to allow for aspiration of blood, which allows a physician to confirm entry into the portal vein. The system and method overcomes the disadvantages of existing methods and systems that use a stiff needle/cannula to aim and puncture from the hepatic vein to the portal vein. These devices are rigid, and do not have the adaptability to conform to variations in anatomy, making it difficult and dangerous to aim and puncture towards the target. The disclosed embodiment provides a flexible alternative that can navigate tortuous anatomy and effectively aim at the portal vein target and be advanced thereto while minimizing tissue damage.

Figure 1B:
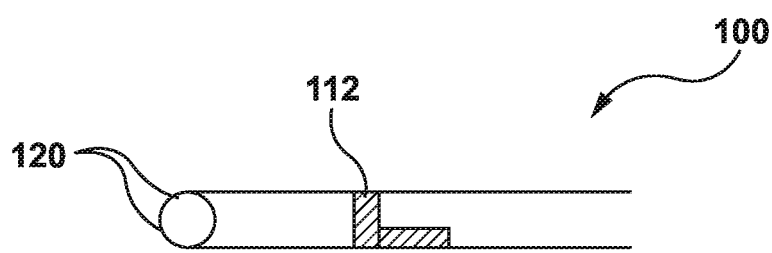
FIG. 1B is an illustration of an RF catheter and method of using the same in accordance with an embodiment of the present invention.
Figure 1C:
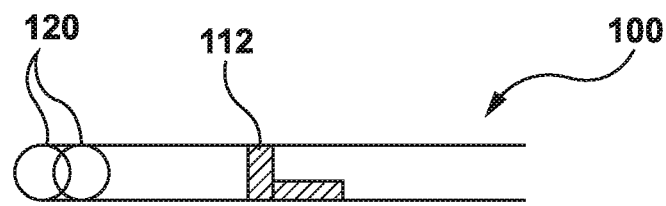
FIG. 1C is an illustration of an RF catheter and method of using the same in accordance with an embodiment of the present invention.
Figure 1D:
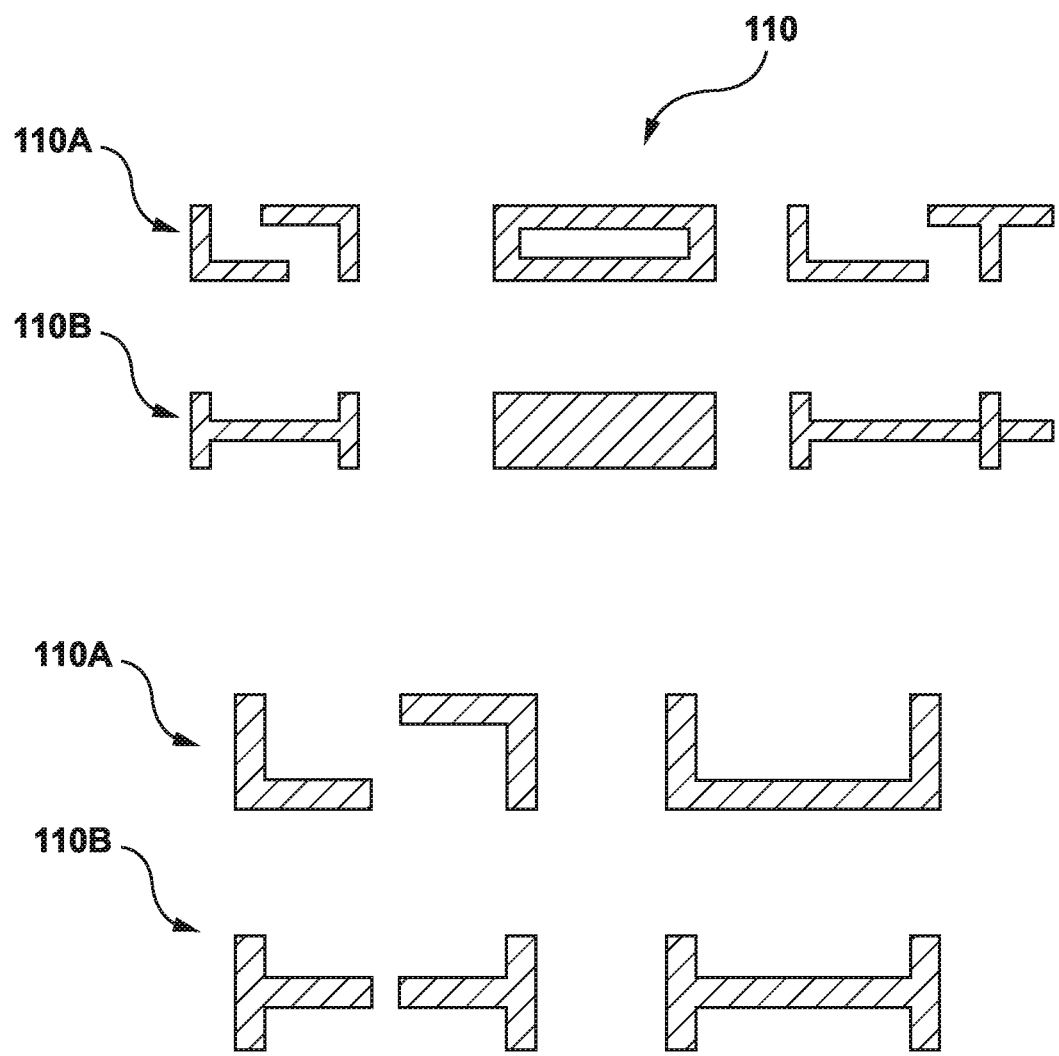
FIG. 1D is an illustration of directional markers in accordance with various embodiments of the present invention.

In some embodiments, the system additionally provides a guiding catheter or sheath 100, as shown in FIG. 1A. In some such examples, a sharp angled (70 degrees to 90 degrees) guiding catheter or sheath 100 is provided, which can direct the RF catheter towards the portal vein from the hepatic vein. In some examples, the guiding catheter or sheath 100 additionally comprises a directional marker such as a directional Radiopaque (RO) band 110 that provides an indication of orientation under imaging, such as fluoroscopy, to ensure adequate positioning of the guiding catheter or sheath within the hepatic vein. In one such example, the directional RO band 110 may be an LT marker 112, as shown in FIG. 1A. Under imaging for example under an Anterior-Posterior or Anteroposterior (A-P) view. The LT marker 112 is visible as a T-shaped marker in a side-view which indicates that the tip of the guiding sheath or catheter 100 is positioned 90 degrees to the desired angle, as shown in FIG. 1A. The physician can re-orient the tip of the sheath or catheter 100 by 90 degrees to visualize the tip in a top view whereby the LT marker 112 is visible as an L-shaped marker as shown in FIGS. 1B and 1C. In some embodiments, when visible as an L-shaped marker, the LT marker indicates that the tip of the guiding sheath or catheter 100 is positioned in the desired plane of orientation. In other examples, as shown in FIG. 1D, the directional RO band 110 may have alternative designs. The directional RO band 110 is visible in different shapes in top views 110A and side views 110B, as shown, to provide directionality or orientation information to the physician.

In some embodiments, the guiding catheter or sheath 100 additionally comprises one or more alignment markers such as alignment RO bands 120 on the angled tip of the guiding catheter or sheath 100, as shown in FIGS. 1B and 1C, which allow alignment under 'gun-barrel' (i.e. 'head-on') view. FIG. 1C illustrates the guiding catheter or sheath 100 when the alignment RO bands 120 are not aligned. The physician may adjust the position of the guiding catheter or sheath 100 to align the alignment bands 120 in the gun-barrel view, as shown in FIG. 1B.

Figure 2A:
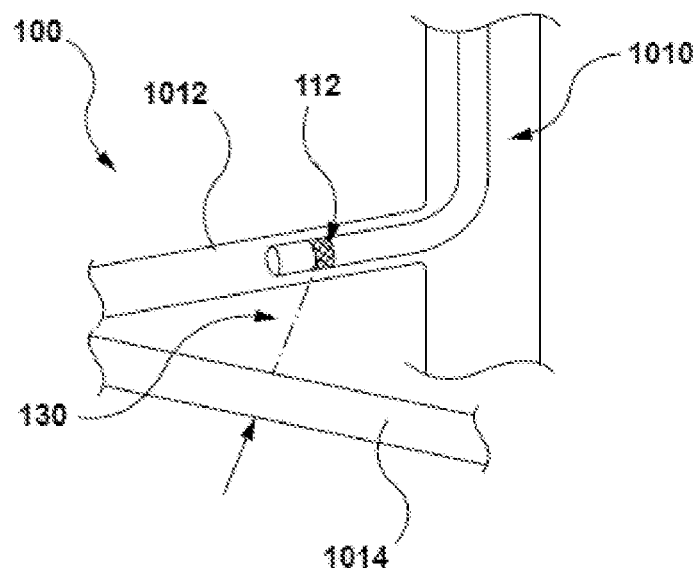
FIG. 2A is an illustration of a device and method of use thereof, in accordance with an embodiment of the present invention.
Figure 2B:
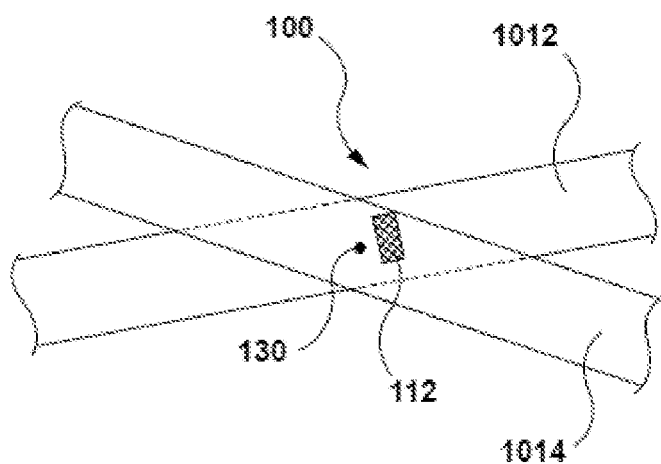
FIG. 2B is an illustration of a method of the present invention utilizing a 'gun-barrel' view plane in accordance with an embodiment of the present invention.

FIGS. 2A and 2B additionally illustrate the guiding catheter or sheath 100 in the A-P view, and the 'gun-barrel' plane view, respectively. FIG. 2A illustrates the guiding catheter or sheath 100 positioned in the hepatic vein 1012 that has been accessed from the inferior vena cava 1010. In one such example, the guiding catheter or sheath 100 positioned in the hepatic vein with the directional RO band 110 visible in the A-P view. The desired path of travel of the RF catheter is shown as a potential straight tract or path 130 from the hepatic vein to the portal vein. FIG. 2B on the other hand shows the directional RO band 110 in the 'gun-barrel' view plane. The path 130 from the portal vein to the hepatic vein is shown in a head-on view for aiming the guiding catheter or sheath 100 for directing an RF catheter from the hepatic vein to the portal vein. The 'gun-barrel' view plane is above the portal vein and perpendicular to a straight trajectory from the puncture location in the hepatic vein to the portal vein. In a particular example, the ideal chosen straight trajectory is the shortest distance from the puncture location to the portal vein.

RF Catheter Method Workflow

Figure 3A:
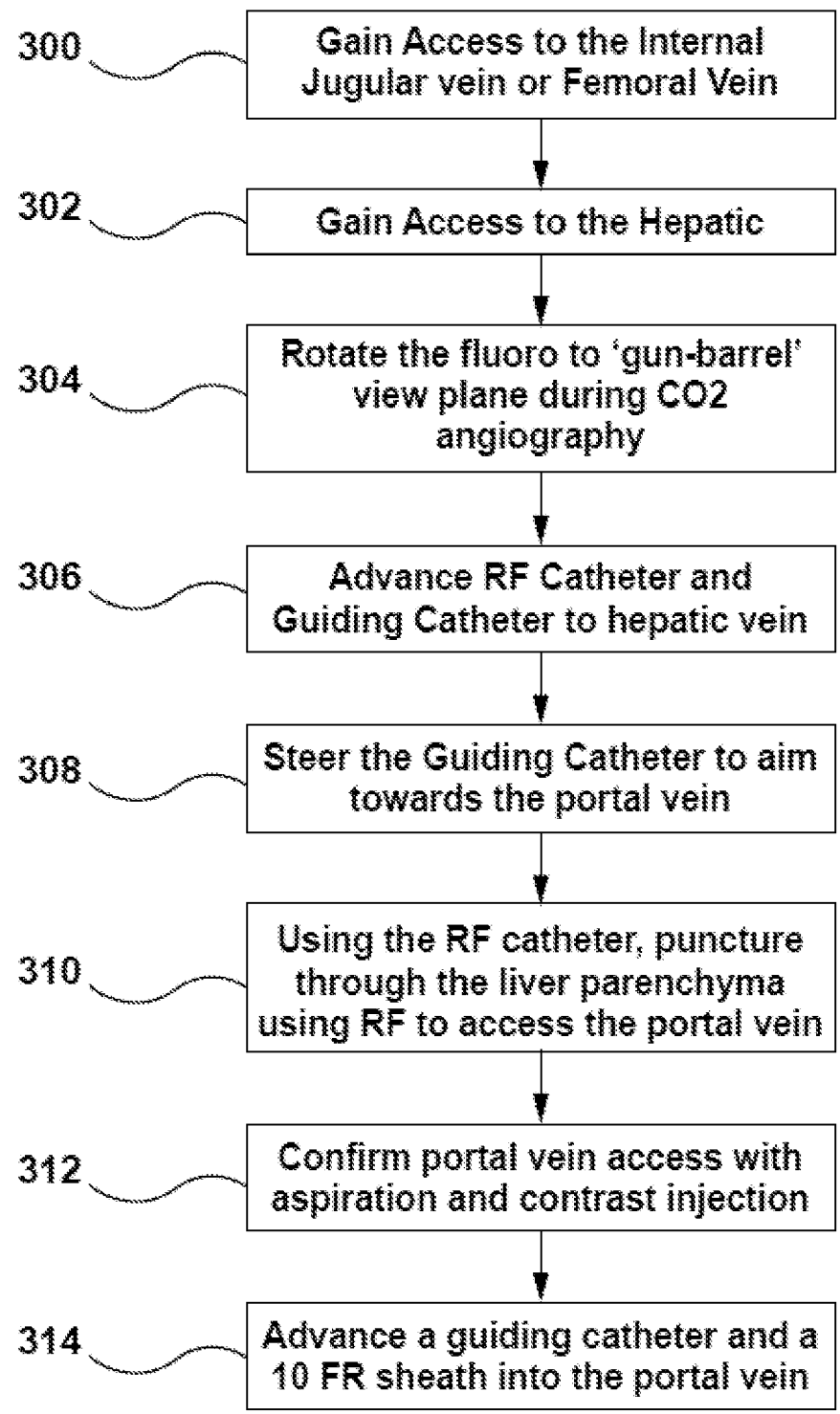
FIG. 3A is a flow diagram showing a method of performing a transvascular procedure using an RF catheter in accordance with an embodiment of the present invention.

In accordance with an embodiment of the present invention, a method is provided for performing a transvascular procedure such as a TIPS procedure to create a pathway from the hepatic vein to the portal vein through the liver parenchyma using RF. An example of a method of the present invention is illustrated in a flow chart shown in FIG. 3A. The method comprises the following steps: at step 300, gaining access to internal jugular vein or femoral vein with an introducer kit; at step 302, gaining access to hepatic vein through the inferior vena cava with a guide wire and a catheter; removing the catheter; advancing a guiding catheter or sheath, e.g. a 10 Fr guiding catheter or sheath with an RO band at the distal end, into hepatic vein (alternatively the 10 Fr sheath may be advanced after the access to the portal vein has been confirmed). In some such examples, a guiding catheter or sheath with one alignment markers and/or directional markers at the distal end may be advanced into the hepatic vein. The method additionally comprises: placing the distal end of the guiding catheter or sheath at the desired puncture location in the hepatic vein; removing the guide wire; at step 304, performing imaging at the hepatic vein to visualize the portal vein. In one such example, standard $CO_2$ angiography may be used at the hepatic vein to visualize the portal vein. In one such example, the step of imaging additionally comprises: rotating the fluoro to the 'gun-barrel' view plane as shown in FIG. 2B. In some examples, the visualization by $CO_2$ is very momentary. It may require repeated injection/visualization (for several seconds) and confirming until the gun-barrel view plane is found. Thus, the process might require $CO_2$ injection to be delivered several times. Once the 'gun-barrel' plane view has been obtaining the method additionally involves the steps of: removing the $CO_2$ angiography devices. The method additionally comprises: at step 306, advancing the RF catheter in the guiding catheter or sheath together through the 10 Fr sheath to the puncture location. The RF catheter may then be connected to the RF generator with a cable or other electrical coupling means. In other examples, other imaging techniques such as intravascular ultrasound (IVUS), as further outlined hereinbelow.

Figure 3B:
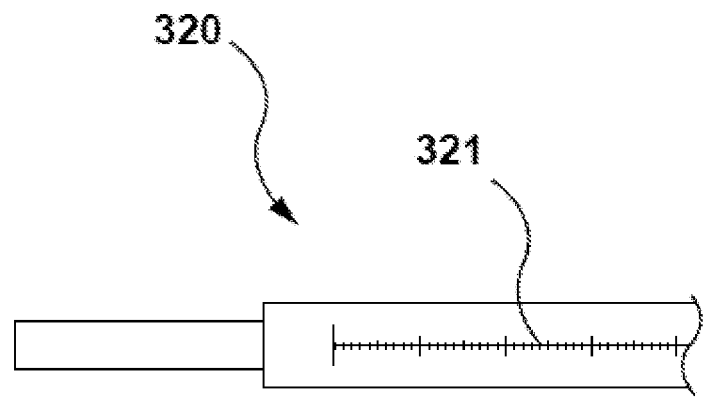
FIG. 3B is a is an illustration of a portion of an RF catheter for carrying out a transvascular procedure, in accordance with an embodiment of the present invention.
Figure 3B:
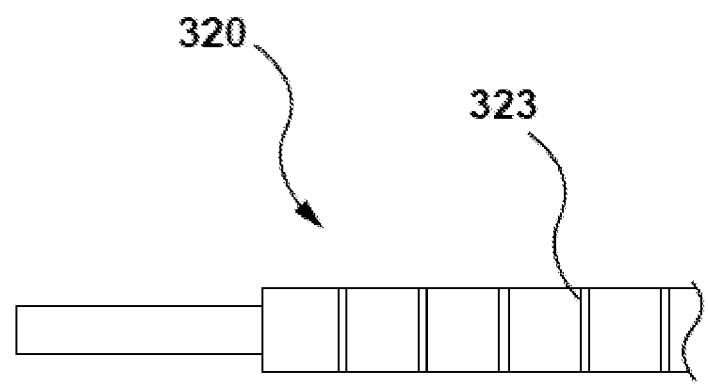

At step 308, the physician may then steer the guiding catheter to aim towards the portal vein. For example, the physician may steer the guiding catheter to aim towards the portal vein utilizing the directional markers and the alignment markers so that the angled section of the guiding catheter is pointing towards and perpendicular to the 'gun-barrel' viewing plane. In a specific example, the physician may utilize the directional RO bands and the alignment RO bands (as shown in FIGS. 1A-1C) to steer the guiding catheter or sheath so that the angled section of the guiding catheter or sheath is pointing towards and perpendicular to the 'gun-barrel' viewing plane. While keeping the guiding catheter in this 'aiming' position, at step 310, the user may apply RF energy and advance the RF catheter towards the portal vein, creating a tract from the hepatic vein to the portal vein to create a shunt there-between. As such, the guiding catheter functions to guide and aim the RF catheter from within the hepatic vein towards the portal vein to aim the RF catheter towards the portal vein, which allows RF catheter to apply RF to puncture through the liver parenchyma tissue along a desired trajectory towards a target site of the portal vein. Application of RF energy enables creation of a channel between the hepatic and portal veins with minimal force using RF while minimizing damage to the vasculature and the liver tissue. In some embodiments, the advancement length of the RF catheter can be controlled by a travel distance indicator placed along the back or proximal portion of the RF catheter. FIG. 3B is an illustration of a proximal end of a device such as an RF catheter (or in alternate embodiments, for example an RF guidewire), in accordance with an embodiment of the present invention. The device comprises depth markers 320 along the proximal end of the device. The depth markers 320 may allow the user to be able to see how far the device is progressing into the patient without relying on fluoroscopic images. In one specific example, depth markers 320 may include etches or printed markings 321 or alternatively, bands 323 that are provided along a proximal shaft of the device, indicating a scale in centimetres or inches. This scale may be used to determine how deep the device is advanced relative to a reference point set by the user.

In some embodiments, the RF catheter can be advanced in a single step to a desired distance or length. Alternatively, the RF catheter can be advanced in several discrete steps (such as two or more discrete steps) under the application of energy while confirming the trajectory under imaging. Under the 'gun-barrel' view, the physician may then verify that the tip of the RF catheter is within the portal vein outline. Additionally, at step 312, the physician can connect a syringe to the RF catheter and aspirate to confirm that the RF catheter has been positioned within the portal vein. If blood is seen, contrast can be injected to confirm access to the portal vein. Alternatively, the step of confirming portal vein access may comprise utilizing any of the techniques for confirming portal access as outlined for alternative methods of the present invention as outlined herein below. Once the portal vein has been accessed by the RF catheter, at step 314, the physician can advance the guiding catheter or sheath into the portal vein. The RF catheter can then be removed and a guidewire can be advanced into the portal vein. A sheath such as a 10 Fr sheath can then be advanced over the guiding catheter or sheath into the portal vein and the guiding catheter or sheath can then be removed. The guidewire may also be removed leaving the 10 Fr sheath in place within the portal vein. The procedure may be completed by placing a stent within the tract between the hepatic and portal veins in a conventional manner. In some examples, the guiding catheter or sheath or the RF catheter may be steerable.

In some embodiments, the guiding catheter or sheath has a relatively large angle or curvature of radius, for example, between about 70 degrees to about 90 degrees. In some such embodiments as described herein above, the guiding catheter or sheath is advanced over the RF catheter through the tract or passage/channel created by the RF catheter between the hepatic and portal veins. In some embodiments, it may be difficult to advance the relatively large angled guiding catheter or sheath. In some such embodiments, in order to further facilitate the procedure, the method and system additionally comprise using an advancing catheter between the guiding catheter or sheath and the RF catheter. In some such examples, once the physician has gained access to the portal vein using the RF catheter, he/she may advance the advancing catheter into the portal vein while the relatively large angled guiding catheter or sheath remains in the hepatic vein. In a specific example, the advancing catheter may be substantially straight or may alternatively have a relatively small angle of curvature. In some such examples, the angle or radius of curvature of the advancing catheter may be between about 0 degrees and 30 degrees. Furthermore, in examples where the advancing catheter has a relatively small angle, the advancing catheter may additionally be used to change the trajectory of the RF catheter during advancement through the liver parenchyma.

In alternative embodiments, the guiding catheter or sheath may be steerable and may enable active steering to allow for in situ angle adjustment of the guiding catheter to aim the RF catheter towards a selected position along the portal vein.

Embodiments of RF Catheters

In accordance with some embodiments of the present invention, an RF catheter 400 is disclosed as outlined herein above. RF puncture systems and methods, as discussed further below, increase ease of puncture through tissue. In addition, in accordance with certain embodiments of the present invention, RF puncture devices enable confirmation of portal vein access. For example, a flexible RF catheter 400 is disclosed that provides RF capabilities to provide ease of puncture through tissue such as the portal vessel wall, the liver parenchyma, and the hepatic vessel wall, and additionally offers the ability to confirm portal vein access without adding steps and complexity to the procedure. The proposed RF catheter 400 additionally provides a large enough lumen, or in other words an adequately sized lumen, to permit aspiration and/or delivery of contrast to allow for confirmation of portal vein access.

Thus, in some embodiments, a flexible RF catheter 400 is provided that may allow the user to confirm (for example, substantially concurrently with RF delivery) whether or not the portal vein, or any other vasculature, has been accessed by the RF device without adding any additional procedural complexity. It may also allow for device exchange without requiring additional devices to be positioned in the portal vein. As such, the use of the RF catheter 400 may reduce the number of devices required to complete a TIPS procedure, and additionally provide a means to readily confirm portal vein access once the RF puncture has been performed. In some embodiments, any of the techniques outlined in the present disclosure may be used for confirming portal vein access. The proposed solution of an RF catheter 400 attempts to reduce the number of required devices and decrease procedural complexity.

The RF catheter may be utilized to perform Transjugular Intrahepatic Portosystemic Shunt (TIPS) procedures and Direct Intrahepatic Portocaval Shunt (DIPS) procedures, and any other procedures that require puncture and aspiration/injection/device exchange, such as transseptal procedures.

Example 1

Figure 4A:
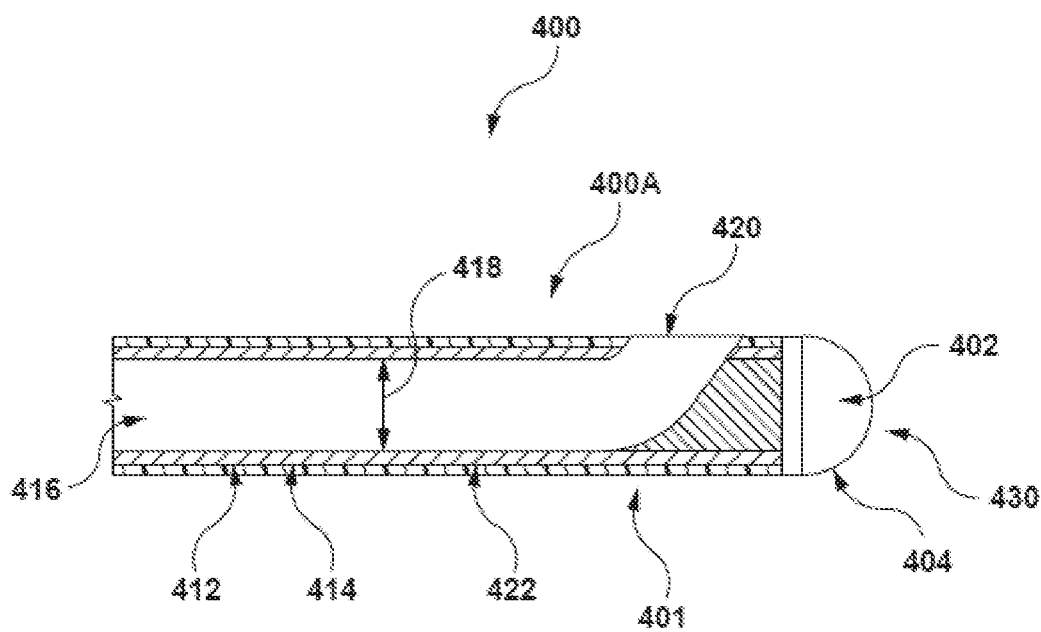
FIG. 4A is a cross-sectional illustration of an RF catheter with a distal electrode, in accordance with an embodiment of the present invention.

In a specific example, as illustrated in FIG. 4A, an RF catheter 400A is disclosed with an RF electrode 402 that forms an active RF tip 404 at its distal end. In some examples, the RF catheter comprises a hypotube 414 defining an inner lumen comparing a polymer insulator disposed thereon. The RF electrode 402 forming an active RF tip at a distal end of the hypotube 414. As such the RF electrode 402, positioned at the distal end 430 of the RF catheter 400A, is connected with the proximal end 410 of the RF catheter 400A via a hypotube 412, for example, a cut hypotube, such as a laser cut hypotube 414, or alternatively through a wire embedded in the wall of the RF catheter. In one such example, where the RF catheter 400A comprises a laser-cut hypotube the laser-cut hypotube may comprise a conductive material such as a metal filler material having a polymer insulation 422 over it. In one example, the RF catheter defines an inner lumen 416 that has an inner diameter 418 that is between about 0.035" to about 0.038" that smoothly transitions to a side port. In some examples, the side-port is positioned proximal to the distal end of the hypotube 414. The side port allows for fluid injection and withdrawal, and enables device exchange. In some examples the distal tip of the RF catheter may be curved. In other examples, the distal tip of the RF catheter may be straight.

In one such example, the transition between the RF electrode 402 and catheter body 401 comprises a smooth taper so it does not form a shoulder. This configuration allows for easy advancement of the RF catheter 400A without the shoulder catching on surrounding tissue. In one example, the side port 420 is large enough, or in other words sufficiently sized, to facilitate advancement of an approximately 0.035"-0.038" guidewire there-through. In one example, the conductive material connecting the proximal and distal ends of the RF catheter 400A comprises a flexible hypotube 414, allowing for strength and a secure connection.

Example 2

Figure 4B:
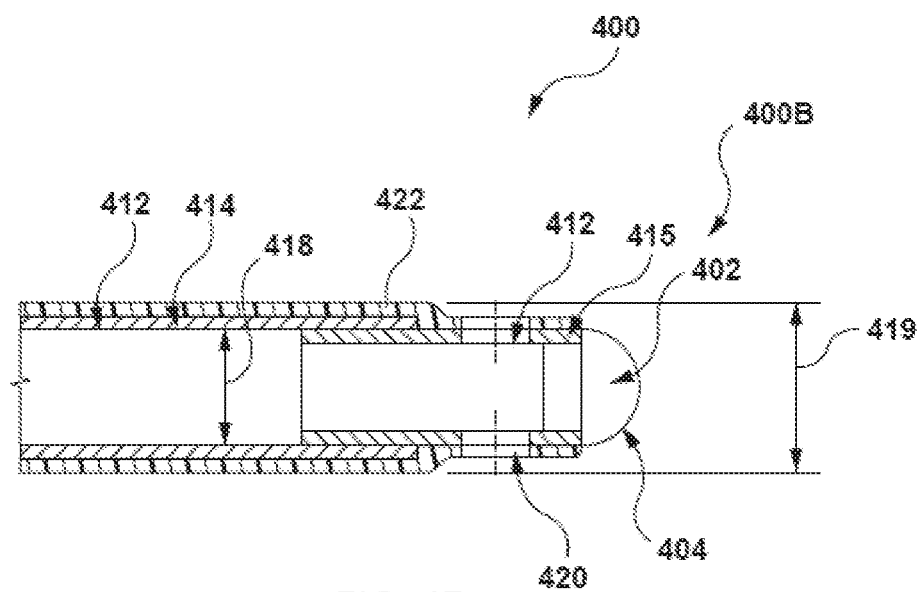
FIG. 4B is a cross-sectional illustration of an RF catheter with a distal electrode, in accordance with an alternative embodiment of the present invention.

In a further alternative as illustrated in FIG. 4B, an RF catheter 400B is disclosed that comprises a hypotube 412 that in one example is a domed distal hypotube 415 that is receivable within a proximal hypotube 414, the domed distal hypotube 415 forming a domed RF electrode at the distal tip. In one specific instance, the domed distal hypotube 415 is inserted into (or in other words received within) the distal end of a catheter such as a microcatheter with an outer diameter (OD) 419 that is approximately between about 0.035"-0.038", creating an electrical connection between the distal end 430 and the proximal end 16 via a proximal laser-cut hypotube 414 embedded within the catheter 400B. As outlined herein, the domed hypotube 415 forms a domed RF electrode 402 at the distal active tip 404. This configuration allows for advancement of a regular 4 Fr-6 Fr catheter over the RF catheter 400B once RF puncture has been performed and access to the desired location within the anatomy confirmed. Similar to the example shown in FIG. 4A, RF Catheter 400B comprises one or more side-ports 420 for fluid delivery or injection.

In one specific example, the outer diameter (OD) 419 of the RF catheter 400B is equal to about 0.035"-0.038" to ensure compatibility with standard 4 Fr-6 Fr catheters. In a specific instance, the domed hypotube 415 is a stiff or rigid distal hypotube and the proximal hypotube 414 is a flexible hypotube. In some such embodiments, the outer diameter of the stiff distal hypotube 415 is either equal to, or slightly greater than, the inner diameter (ID) 418 of a flexible proximal hypotube 414. This configuration ensures a tight fit to maintain the electrical connection without having to rely on epoxies or glues to hold the components together.

In some such examples, an RF Catheter may comprise an RF catheter owned by the Baylis Medical Company Inc., and as described further detail in the PCT application PCT/IB2014/059696, Publication No. WO2014/141105A1, as well as PCT application PCT/IB2014/059830, Publication No. W2014/141197A1 which are both incorporated herein by reference in their entirety. The RF catheter may provide an advantage in terms of instant access confirmation through aspiration as well as wire advancement/exchange.

In accordance with alternative embodiments of the present invention, an RF guidewire, or in other words an RF wire, may be used instead of the RF catheter. In other embodiments, other suitable RF devices may be utilized.

In some embodiments, the guiding sheath or catheter 100 may comprise a fixed angle. In other alternatives, the guiding catheter or sheath 100 may be steerable. In some such examples, the guiding catheter is steerable to allow for in-situ adjustment of the guiding catheter, for example an angle of the guiding catheter, to enable it to aim at a selected position or location along the portal vein.

In some embodiments, the directional marker design or the design of the directional RO band 110 may be altered and may still provide information about the orientation of the device angle, such as that of the RF catheter 400. In some examples, the alignment markers such as the alignment RO bands 120 may comprise one or more RO bands. In other examples, the alignment RO bands may comprise two or more RO bands. In some examples, the present invention utilizes a 'gun-barrel' view plane to provide the necessary directional information. In other examples, other view planes can be used to provide the directional information. In a further alternative, the guiding catheter or sheath 100 may be steerable and may provide the user with a larger angle or radius of curvature, for example between about 70 degrees to about 90 degrees, for aiming, and additionally may provide the user with a smaller angle or radius of curvature, for example between about 0 degrees to about 30 degrees, while advancing.

In an alternative embodiment, an RF wire or RF guidewire is used in conjunction with an advancing catheter with a relatively small angle of between about 0 degrees to about 30 degrees, and a guiding catheter 100 with a relatively large angle of between about 70 degrees to about 90 degrees, along with a 10 Fr sheath.

In one such example, where an RF guidewire is used instead of an RF catheter 400, the method steps are similar to the RF Catheter Method Workflow, described previously, prior to the steps required to obtain portal access confirmation. In the present example, two methods can be used to confirm portal access. The first method uses tactile feedback from the RF wire to identify if the tip of the RF wire is in the portal vein. With a flexible RF wire, the RF wire will not substantially advance without RF in the liver parenchyma but would advance further if the tip of the RF wire is in a vein. The second method for confirming position of the RF wire includes advancing the advancing catheter along with the RF wire following puncture, and then withdrawing the wire completely to use the catheter for aspiration or contrast injection. Alternatively, any of the techniques provided in the present disclosure may be used to confirm portal vein access.

Thus, in accordance with some embodiments of the present invention, a flexible RF puncture device is provided for creating a channel or tract between the hepatic vein and the portal vein through the liver parenchyma with the use of RF energy. The use of RF energy allows the device to traverse through tough liver tissue that may be scarred or diseased and additionally allows for use of a flexible atraumatic device that minimizes damage to the liver and allows traversal through tortuous anatomy. The use of RF energy additionally allows for a series of flexible access devices and methods for guiding the flexible RF puncture device into the hepatic vein and to direct the flexible RF puncture device from the hepatic vein towards the portal vein. Access may be provided to the hepatic vein from internal jugular access or femoral access.

In accordance with various embodiments of the present invention, different imaging modalities may be utilized in order to assist with the procedure in terms of aiding the positioning, steering, and/or aiming of various devices including the RF catheter. In some examples, the imaging modality may comprise one or more of fluoroscopy, $CO_2$ imaging, or Intravascular Ultrasound (IVUS). In other embodiments alternate means of imaging may be used.

RF Guidewire and Steerable Sheath

In accordance with some embodiments of the present invention, an RF guidewire is provided that may be usable independently from a catheter inside a steerable sheath in order to complete a Transvascular procedure, such as a Transjugular Intrahepatic Portosystemic Shunt (TIPS) procedure. In some embodiments, a Radiofrequency (RF) guidewire is provided that is usable with a support catheter. The RF guidewire and support catheter may be usable together to form an RF guidewire catheter assembly. In some such embodiments, the RF guidewire catheter assembly is usable with a steerable sheath. In some examples, the RF guidewire may be coupled to the support catheter to form the RF guidewire catheter assembly. In other examples, the RF guidewire may be usable with but independent from the support catheter to form the RF guidewire catheter assembly. Similarly, such an RF guidewire catheter assembly may also be usable with a steerable sheath in order to complete the TIPS procedure.

In accordance with one such embodiment of the present invention, a system and method are provided for performing a TIPS procedure, the system comprising a flexible RF guidewire, or in other words, a flexible RF wire, for creating a tract or passage from the hepatic vein to the portal vein, and a steerable guiding sheath for navigating through tortuous anatomy for aiming and directing the RF guidewire. In some such embodiments, the steerable sheath comprises an active steering mechanism that enables actuation of the sheath to enable steering. In summary, the steerable sheath and RF guidewire combination allows for accessing the hepatic vein, allows for the assembly to be aimed at the portal vein target, and additionally enables puncture through the hepatic vessel wall, the liver tissue, and the portal vessel wall by applying RF through the RF guidewire while complying to the anatomy with minimal mechanical resistance. In some embodiments the assembly comprises a steerable sheath that allows for in-situ angle adjustment for gaining access to the hepatic vein and aiming; an RF guidewire, which in some examples comprises a guidewire with an RF electrode at its distal end to enable RF cutting; and a catheter to facilitate crossing, aspiration/contrast injection, and device exchange.

In some embodiments of the present invention, a method of carrying out a TransJugular Intrahepatic Portosystemic shunt procedure is provided that utilizes a flexible telescoping assembly comprising an RF guidewire, a crossing catheter, a flexible dilator, a steerable sheath and an introducer sheath in a telescoping arrangement, the method for creating a pathway between vasculature comprising a hepatic vein and a portal vein. The method comprises the steps of: gaining access to the hepatic vein; advancing the telescoped assembly into the hepatic vein; under imaging, using the steerable sheath to aim the telescoped assembly in-situ from within the hepatic vein towards the portal vein to orient the RF guidewire towards the portal vein; delivering RF and advancing the RF guidewire through the liver parenchyma to permit controlled advancement of the RF guidewire towards the portal vein target, the RF guidewire enabling puncturing through the liver parenchyma and a vessel wall of the portal vein; confirming portal vein access; advancing the telescoped assembly into the portal vein and removing all devices except the introducer sheath for deploying a stent there-through; wherein the telescoping assembly allows for creation of an artificial channel between the hepatic and portal veins by enabling the steerable sheath to aim the assembly including the RF guidewire towards the target site within the portal vein, and wherein the system enables the RF guidewire to puncture through a hepatic vein wall, the liver parenchyma, and the portal vein wall with minimal force using RF while minimizing damage to the vasculature and the liver tissue and minimizing the need for device exchanges.

In some examples provided herein below, the steerable sheath provided is a steerable sheath, by Baylis Medical Company Inc., that is described in more detail in PCT application PCT/IB2013/055013, Publication No. WO 2013/190475A2, which is incorporated herein by reference in its entirety. Additionally, in some such examples, the RF guidewire is an RF guidewire sold by Baylis Medical Company Inc., and as disclosed in application Ser. No. 12/926,292, and publication No. US 2011/0118735A1, which is also incorporated herein by reference in its entirety.

Figure 5A:
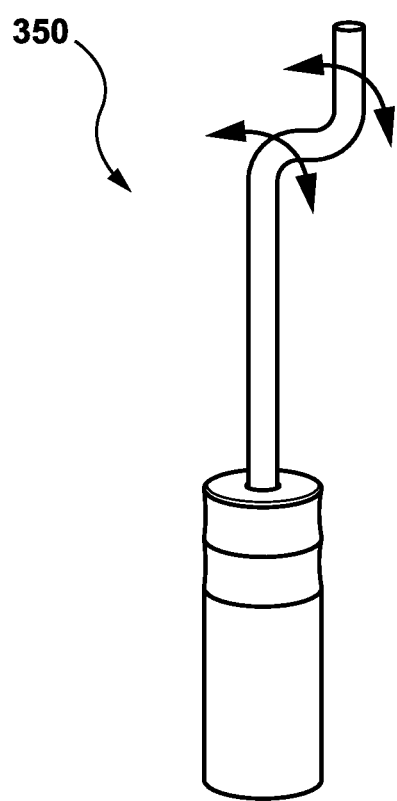
FIG. 5A is an illustration of a dual plane steerable sheath, in accordance with an embodiment of the present invention.

[In some embodiments, as shown in FIG. 5A, a dual plane sheath 350 may be provided that may enable the steerable sheath to be actuated in a first plane (at angle of between about 45 to about 90 degrees to make the turn to the hepatic vein) to access the hepatic vein from the inferior vena cava and then subsequently enables the steerable sheath to be actuated in a second plane (anteriorly or up at an angle of between about 70 to about 90 degrees from the first plane) to allow the steerable sheath to be aligned along a trajectory towards a target within the portal vein. As such the dual plane sheath enables access to the hepatic and enables the sheath to be angled or curved to the desired angle to access the portal vein. With the current embodiment, enhanced benefit may be provided from the ability to achieve multiple angles extending into different planes. The present embodiment provides a second curve to the steerable sheath, and may allow the device to be used in more tortuous anatomy and procedures that require more complex bending angles. In some such embodiments, the second plane of curvature can either be orthogonal, parallel, or anywhere in between to the first plane of curvature.

In other embodiments of the present invention, any other steerable sheath (for example a bi-directional steerable sheath) as outlined in embodiments described herein, may be actuated and oriented to achieve the first plane (at angle of between about 45 to about 90 degrees to make the turn to the hepatic vein) and second plane anteriorly or up at an angle of between about 70 to about 90 degrees from the first plane), similar to the embodiment described herein above to aim and orient a flexible RF device (such as an RF guidewire or an RF catheter) to facilitate a TIPS procedure, in accordance with some embodiments of the present invention.

Example 1 Workflow

Figure 5B:
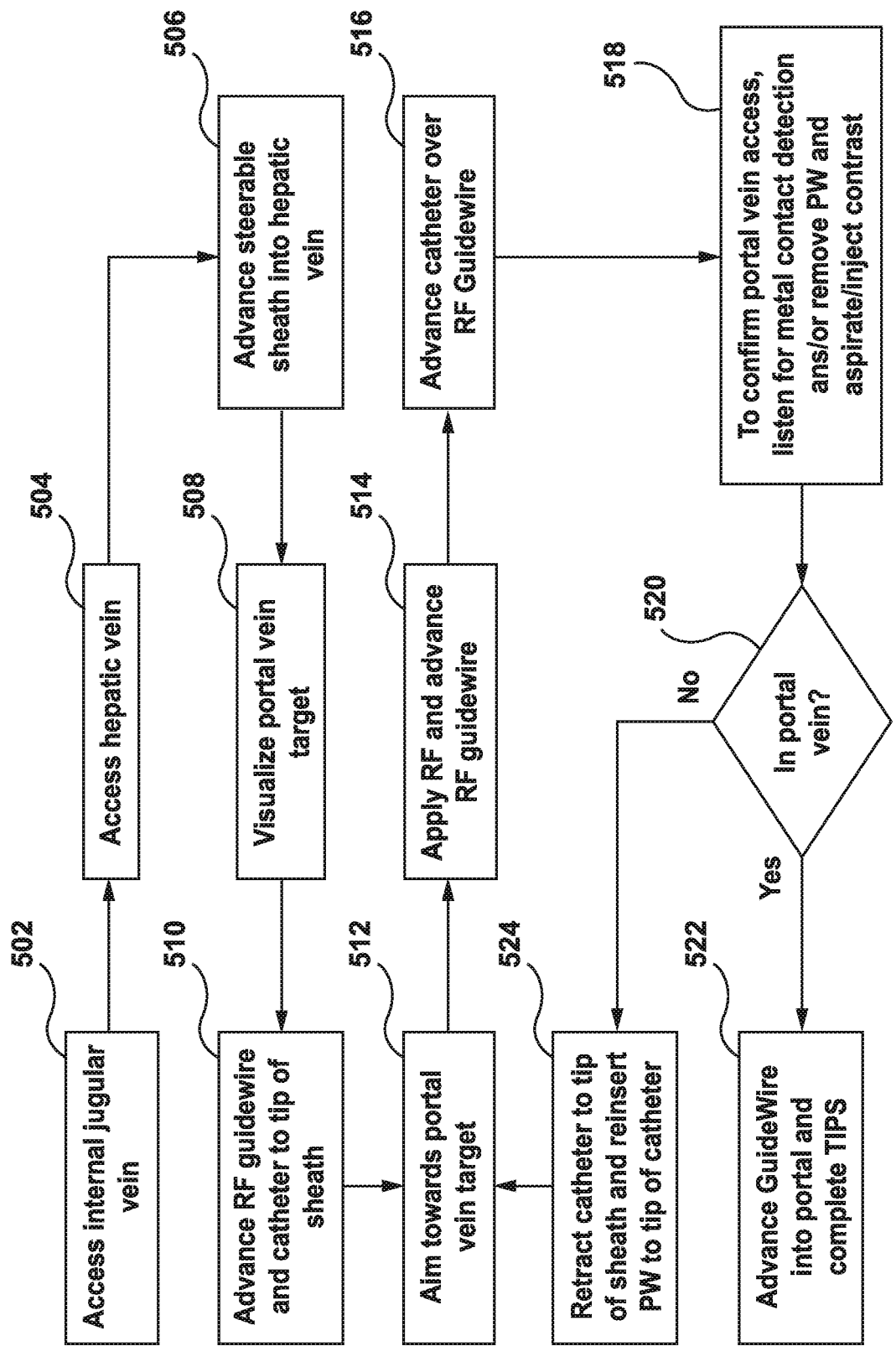
FIG. 5B is a flow diagram showing a method of performing a transvascular procedure using an RF guidewire and a steerable sheath in accordance with an alternative embodiment of the present invention.

In a first example of this embodiment, as shown in the flowchart illustrated FIG. 5B, a system and method are disclosed for carrying out a TIPS procedure using an RF guidewire and a steerable sheath. In some embodiments, the RF guidewire may be an RF guidewire by Baylis Medical Company Inc., and a steerable sheath, also by Baylis Medical Company Inc., both as described in applications referenced herein above and previously incorporated by reference in their entirety.

In one such example, a method is provided for example for carrying out or facilitating a TIPS procedure (for example to treat portal hypertension) using an RF guidewire and a steerable sheath to create a pathway between a portal vein and a hepatic vein. The method comprises the following steps: at step 502, gaining access to internal jugular vein or femoral vein using standard introducer kit; at step 504, gaining access to hepatic vein with a guidewire and catheter via inferior vena cava; removing the catheter; at step 506, advancing a steerable sheath and dilator over guidewire into hepatic vein; removing the dilator and guidewire; and at step 508 visualizing the portal vein using imaging techniques. In some such examples, the method may comprise visualizing the portal vein using standard $CO_2$ angiography techniques, intravascular ultrasound techniques, or fluoroscopy. In a specific example, the step of visualizing the portal vein may comprise inserting a target device (e.g. guidewire, catheter, or snare) into the portal vein to assist in visualizing the portal vein. Alternatively, other imaging techniques may be used to visualize the portal vein, as may be known in the art. The method additionally comprises the following steps: at step 510, advancing an RF guidewire, and a supporting catheter through the steerable sheath to the tip of the steerable sheath. The RF guidewire and the supporting catheter may collectively be referred to as the RF guidewire catheter assembly. In some such examples, the RF guidewire may be an RF guidewire sold by Baylis Medical Company Inc, as described in application referenced herein above and incorporated previously by reference in its entirely. In some examples, the RF guidewire and the supporting catheter may be coupled to one another. In some examples as in the present embodiment, the RF guidewire and the supporting catheter may not be coupled to one another. The method additionally comprises steps of connecting the RF guidewire to an RF generator; at step 512, aiming towards the portal vein target, in some examples, this may involve for example, actuating the steerable sheath, for example, by using the knob on the steerable sheath's handle, to angle the tip of the steerable sheath towards the portal vein or the target within the portal vein. More specifically, in some embodiments, the steerable sheath provides active steering. The method comprises using the steerable sheath to orient in-situ to aim towards the portal vein to provide a predictable trajectory to aim the RF guidewire towards target site within the portal vein. The method additionally comprises: at step 514, applying RF and advancing the RF guidewire through the liver parenchyma towards the portal vein or the target within the portal vein. More specifically, the RF guidewire allows puncture through a wall of the hepatic vein and the liver parenchyma to permit controlled advancement of the RF guidewire towards a target side within the portal vein. The method additionally comprises: at step 516, advancing the supporting catheter over the RF guidewire. As such, the steerable sheath enables the RF guidewire to be aimed towards the target site within the portal vein, and wherein the RF guidewire allows puncture through the hepatic vein wall, the liver parenchyma, and the portal vein wall with minimal force using RF while minimizing damage to the vasculature and the liver tissue and minimizing the need for device exchanges.

Confirmation of Portal Vein Access

The physician may then confirm if the portal vein has been accessed, as shown at step 518. Portal vein access may be confirmed through one or more of various methods described herein. In one specific example, a method is provided whereby a metal target device (e.g. a guidewire) is placed in the portal vein to function as a portal vein target. In some such examples, the step of confirming portal access may comprise inserting a target and assessing proximity to the target from the puncturing device, such as the RF guidewire (or an RF catheter in alternative embodiments of the present invention) In accordance with some of the embodiments described herein above, as the RF guidewire is advanced into the portal vein, it contacts the target device. A radiofrequency generator coupled to the RF guidewire is operable to generate or prompt a "Metal Detection" error, indicating that portal vein access has been achieved. In one such example, the methods outlined in US application number U.S. Ser. No. 13/410,868 and publication number US2012/0215213A1, may be used, which is incorporated herein by reference in its entirely. The portal vein access can be further confirmed through aspiration as described previously. Alternatively, a method is provided to confirm portal vein access, whereby once the RF puncture has been performed and portal vein access is suspected, the RF guidewire is removed and a syringe is connected to the supporting catheter that remains. The plunger of the syringe is then pulled back. If blood is withdrawn it provides an indication that a vessel has been successfully accessed. In order to confirm that the vessel is in fact the portal vein, contrast may be injected under fluoroscopy and the vessel may be observed under imaging. Alternatively, the step of confirming portal access may comprise using tactile feedback.

At step 520, once portal vein access is confirmed, the present embodiment of the method additionally comprises, at step 522, advancing the supporting catheter further into portal vein and inserting and advancing a guidewire such as a stiff guidewire into the portal vein to facilitate the rest of the procedure and to complete the procedure. Alternatively, the core wire maybe re-inserted and may be re-advanced into portal vein and may be advanced further therein to maintain access and facilitate the rest of the TIPS procedure. More specifically, at step 520, if the portal vein has not been accessed, at step 524, the catheter may be retracted to the tip of the sheath, and the core wire comprising the RF guidewire may be advanced into the portal vein to complete the TIPS procedure.

Example 2 Workflow

Figure 5C:
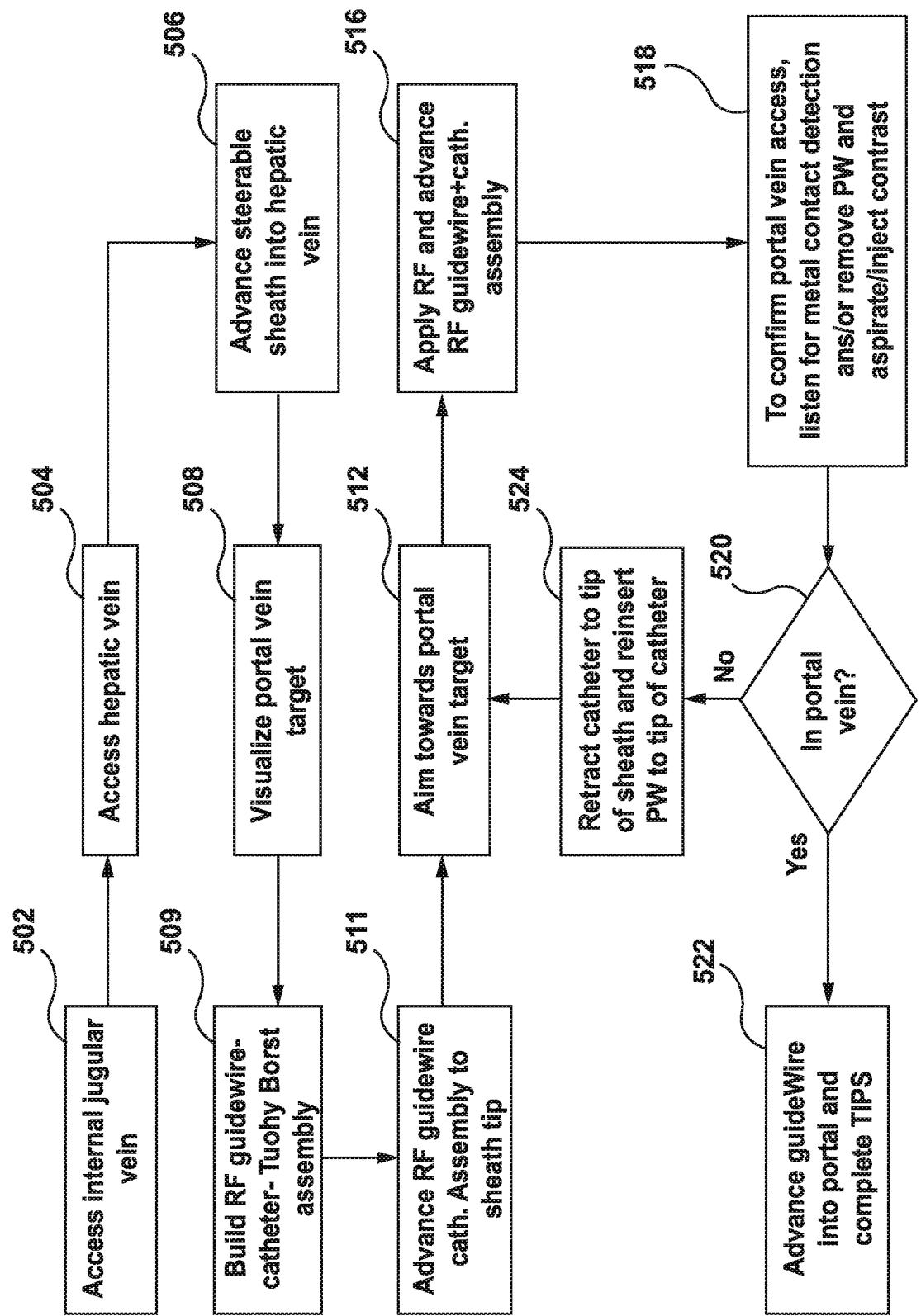
FIG. 5C is a flow diagram showing a method of performing a transvascular procedure using an RF guidewire and a steerable sheath in accordance with a further alternative embodiment of the present invention.

In a second example of this embodiment, as shown in the flowchart illustrated FIG. 5C, a system and method are disclosed for carrying out a TIPS procedure using an RF guidewire and a steerable sheath. In one such example the method comprises the following steps: at step 502, gaining access to internal jugular vein or femoral vein using standard introducer kit; at step 504, gaining access to hepatic vein with a guidewire and catheter via inferior vena cava; removing the catheter; at step 506, advancing the steerable sheath and dilator over guidewire into hepatic vein; removing the dilator and guidewire; and visualizing the portal vein using imaging techniques. In some such examples, at step 508, the method may comprise visualizing the portal vein, for example, using standard $CO_2$ angiography techniques, intravascular ultrasound techniques, or fluoroscopy. In a specific example, the step of visualizing the portal vein may comprise inserting a target device (e.g. guidewire, catheter) into the portal vein to assist in visualizing the portal vein. Alternatively, other imaging techniques may be used to visualize the portal vein, as may be known in the art. At step 509, the method additionally comprises building a locked RF guidewire and catheter assembly, using a locking mechanism to lock the RF guidewire and the supporting catheter, prior to the step of advancing the RF guidewire and the supporting catheter. In some such examples, the method comprises building an RF guidewire and Catheter Tohy Borst assembly More specifically, the method comprises advancing the RF guidewire into a supporting catheter such as a crossing catheter, which for example may be a 5/6 Fr crossing catheter. The RF guidewire is advanced into the crossing catheter ensuring that the tip of the RF guidewire is protruding by about 2-5 mm from the tip of the crossing catheter and its position is locked using a Tuohy-Borst (or equivalent) locking mechanism, forming an RF guidewire catheter assembly. In some examples, as described in the present embodiment, the RF guidewire catheter assembly is formed by an RF guidewire positioned within and coupled to a supporting catheter.

The system and method of the present embodiment additionally comprise the following steps: at step 511, advancing the RF guidewire catheter assembly through the steerable sheath until the assembly is advanced to the tip of the steerable sheath; connecting the RF guidewire to an RF generator; at step 512, aiming towards portal vein target. This may involve actuating the steerable sheath, for example, by rotating the knob on the steerable sheath handle, in order to steer or angle the tip of the steerable sheath towards the portal vein or the target within the portal vein; applying RF using the RF guidewire; and advancing the RF guidewire catheter assembly through the liver parenchyma towards the portal vein or the target within the portal vein.

Example 3A and 3B Workflows

Similar to embodiments discussed herein above, the present example provides an RF guidewire and a steerable sheath that provides a flexible alternative to existing TIPS procedures that use a stiff needle or cannula. The present solution provides flexible devices that can navigate tortuous anatomy in order to effectively aim at the portal vein target. This use of flexible devices provides an advantage over the conventional TIPS procedures use a stiff needle or cannula to aim and puncture from the hepatic vein to the portal vein. The conventional devices are rigid, and as such, they do not provide sufficient adaptability to conform to variations in anatomy. Because of this, aiming towards the target and puncturing may be quite difficult and dangerous.

A system and method are provided for performing a TIPS procedure, the system comprising a flexible RF wire or guidewire, for creating a tract or passage from the hepatic vein to the portal vein, and a steerable guiding sheath for navigating through tortuous anatomy for aiming and directing the RF guidewire. The steerable sheath and RF guidewire combination allows for accessing the hepatic vein, allows for the assembly to be aimed at the portal vein target, and additionally enables puncture through tissue with minimal mechanical resistance using RF while complying with the anatomy. More specifically, the RF guidewire enables puncture through the hepatic vessel wall, the liver tissue, and the portal vessel wall without application of excessive force while reducing the amount of resistance that is encountered during advancement.

Similar to embodiments described above, the present example provides a steerable sheath and an RF guidewire assembly, where the steerable sheath allows for in-situ angle adjustment to gain access the hepatic vein and provides enhanced aiming capabilities to more accurately aim at the portal vein target. The assembly additionally provides an RF guidewire that is usable with the steerable sheath to enable RF puncture. This enables puncture with the use of minimum force with minimal mechanical resistance, while allowing the assembly to comply with the anatomy. The assembly may additionally comprise a guiding sheath or catheter to facilitate crossing, aspiration, contrast injection, and/or device exchange.

Example 3A Workflow

In accordance with an embodiment of the present invention, as shown in FIGS. 11A-11E, a telescoping system 1150 is disclosed comprising an introducer or introducer sheath 1100, for example a 10 Fr Introducer sheath, a steerable guiding sheath 1110 such as a 7 Fr Steerable Sheath, a flexible dilator 1120 such as a 7 Fr flexible dilator, a crossing catheter 1130 such as a 4 Fr crossing catheter, and an RF guidewire 1140. In one such example, the steerable guiding sheath 110 is received within the introducer 1100, the flexible dilator 1120 is received within the steerable guiding sheath 1110, the crossing catheter 1130 is received within the flexible dilator 1120, and the RF guidewire 1140 is received within the crossing catheter. In one example, the telescoped system 1150 comprises an assembly with the introducer 1100, the steerable guiding sheath 1110, the flexible dilator 1120, the crossing catheter 1130 and the RF guidewire 1140 are all received and arranged in the telescoping arrangement described herein above.

In one specific example, the RF guidewire 1140 is a 0.035" guide-wire. In accordance with an embodiment of the present invention, a method is provided for facilitating a Transjugular Intrahepatic Portosystemic Shunt Procedure by creating a pathway between a hepatic vein and a portal vein. In one such example, the method comprises the steps of: advancing the telescoped system into the hepatic vein, as shown in FIG. 11A; steering the 7 Fr steerable sheath to aim towards the portal vein target 1160, as shown in FIG. 11B. In some such examples, the step of steering the steerable sheath comprises active steering. More specifically, the steerable sheath is actuated to aim the telescoping assembly in-situ along a desired trajectory from within the hepatic vein towards the portal vein to orient the RF guidewire towards a desired target site within the portal vein; to orient the RF guidewire towards a desired target site within the portal vein. The method additionally comprises: applying RF and advancing the RF wire into the portal vein, as shown in FIG. 11C. In one such example, RF is applied and the RF guidewire is advanced in a controlled manner from the hepatic vein in order to puncture through a hepatic vessel wall, the liver parenchyma, a portal vessel wall, to create a channel there-through to gain access from the hepatic vein into the portal vein.

Figure 11D:
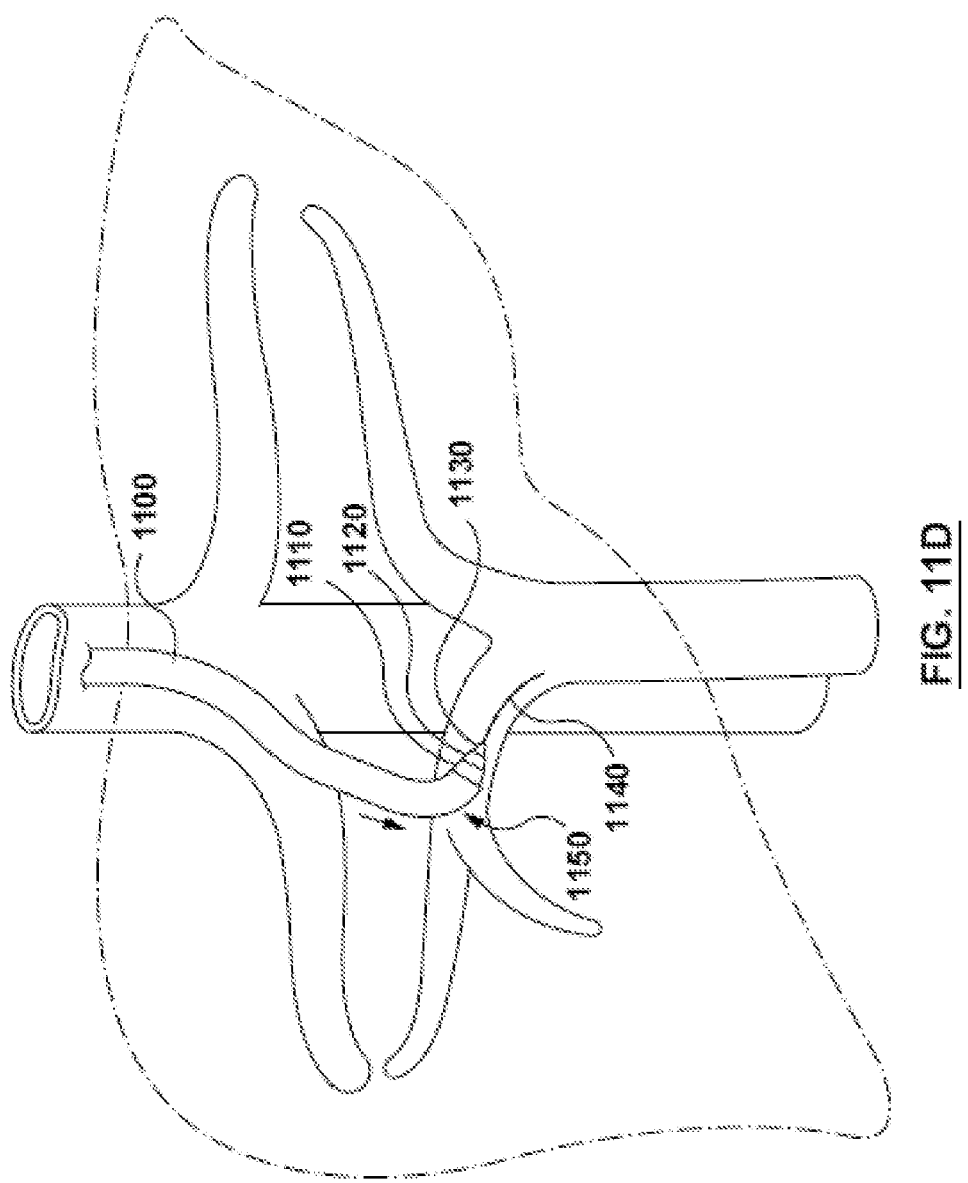

The method then comprises confirming portal vein access, for example using techniques as outlined previously herein above; And after confirmation of the portal access, advancing the telescoped system into the portal vein, as shown in FIG. 11D; removing all devices but the 10 Fr introducer sheath as shown in FIG. 11E to facilitate the rest of the procedure. In some examples, the introducer sheath and guidewire remain to provide access to the portal vein for Stent deployment such as deployment of a GORE® VIATORR® TIPS Endo-prosthesis. In some such embodiments, the method may additionally comprise dilating the channel created by the RF guidewire. In some such examples, the step of dilating the channel is performed using a dilating balloon.

As such an example of the present embodiment provides a telescoping assembly that functions to aim the devices therein from within the hepatic vein towards the portal vein to aim the RF guidewire towards the portal vein to provide a predictable trajectory, and enables creation of a channel between the hepatic and portal vein in a controlled manner using RF with application of minimal force and while minimizing damage to the vasculature and the liver tissue and while reducing the need for device exchanges.

Example 3B Workflow

In accordance with a further alternate embodiment of the present invention, an alternate telescoping system is disclosed as shown in FIGS. 12A-12E. The telescoping system 1250 of the present invention comprises a steerable sheath 1210 comprising a 10 Fr Steerable Sheath, a flexible dilator 1220 such as a 10 Fr Flexible Dilator, a crossing catheter 1230 such as a 4 Fr Crossing Catheter, and an RF guidewire 1240 such as a 0.035" RF Guidewire. In one such example, similar to the example discussed herein above, the steerable guiding sheath 1210 is provided where, the flexible dilator 1220 is received within the steerable guiding sheath 1210, and the crossing catheter 1230 is received within the flexible dilator 1220, and the RF guidewire 1240 is received within the crossing catheter 1230. In one example, the telescoped system 1250 comprises an assembly with the steerable guiding sheath 1210, the flexible dilator 1220, the crossing catheter 1230 and the RF guidewire are all received and arranged in the telescoping arrangement described herein above.

Figure 12C:
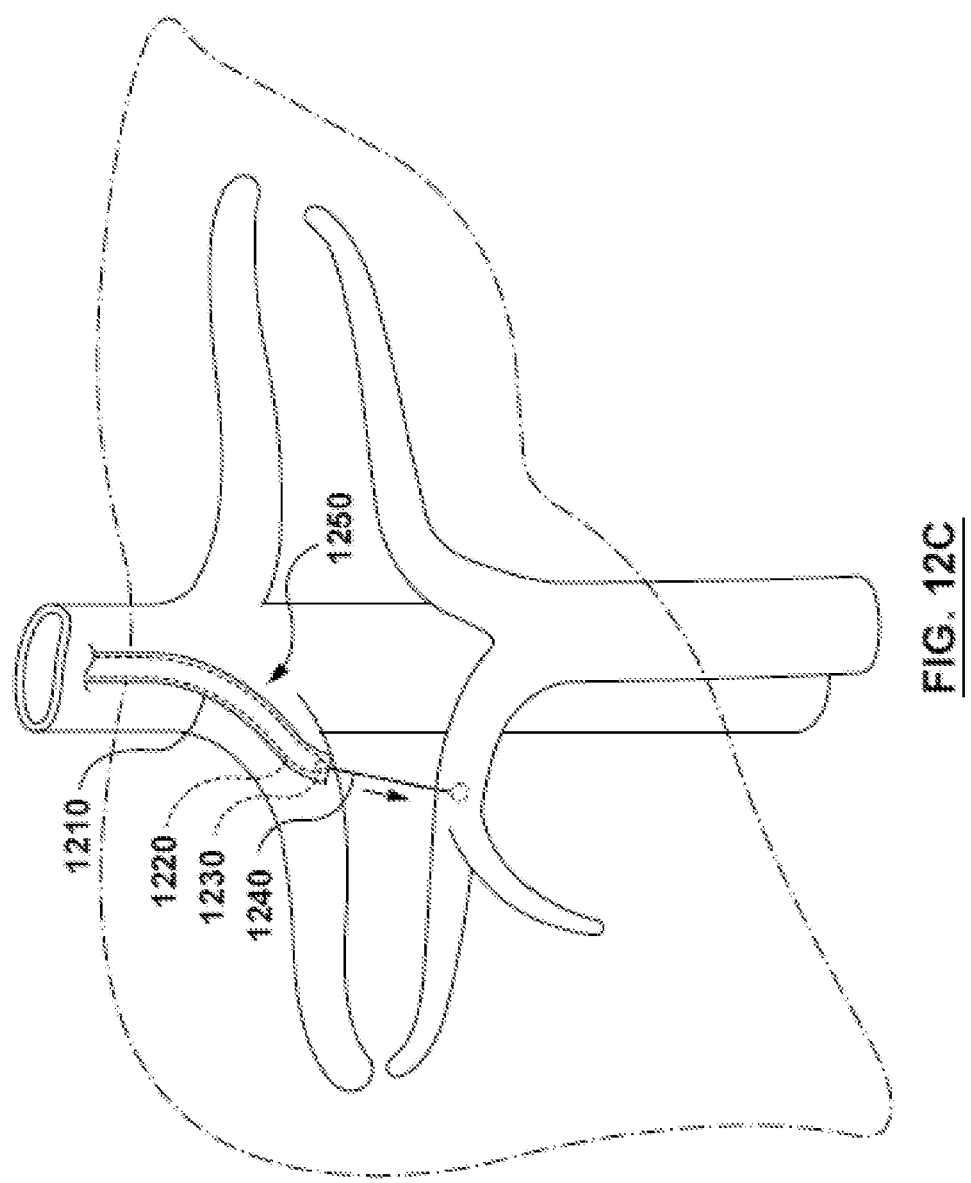
Figure 12E:
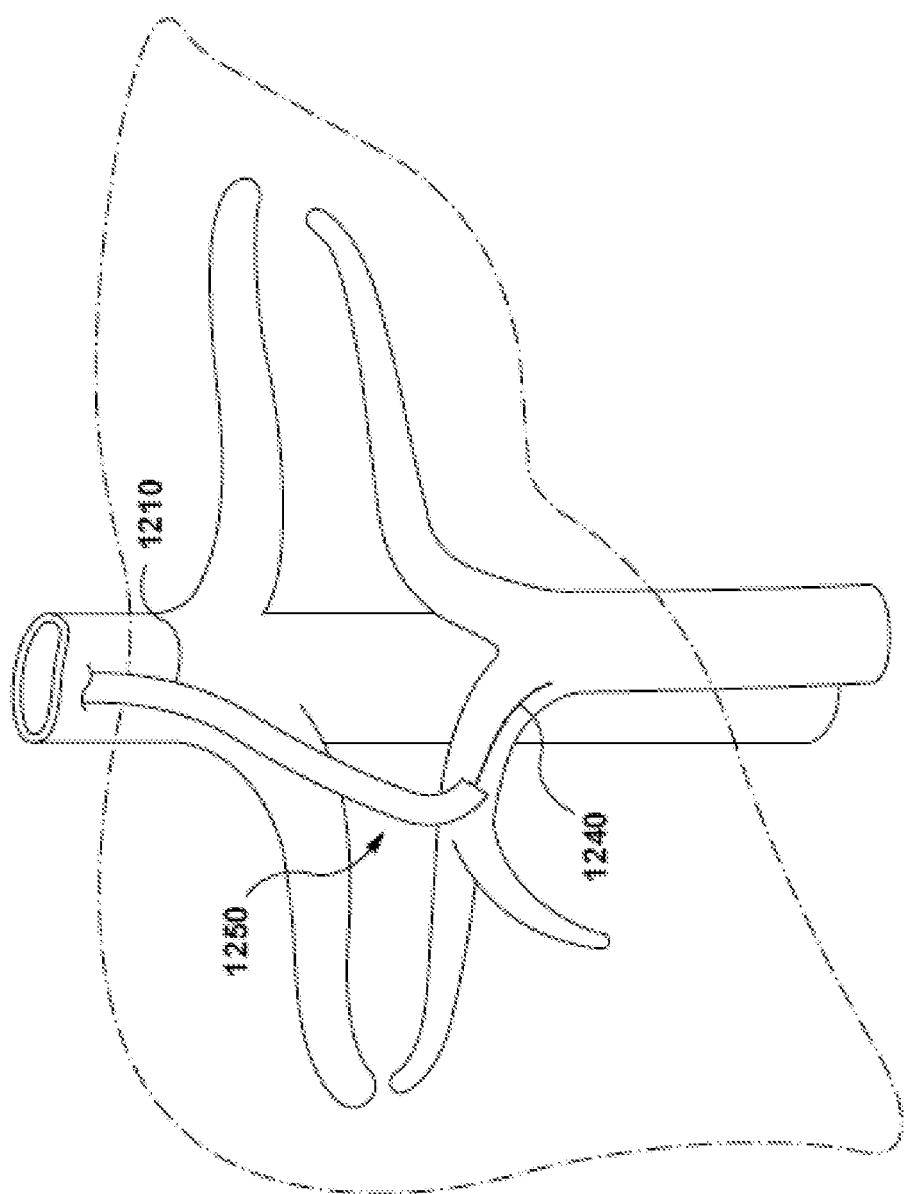

In one specific example, the RF guidewire 1240 is a 0.035" guidewire. In accordance with an embodiment of the present invention, a method is provided for facilitating a Transjugular Intrahepatic Portosystemic Shunt Procedure by creating a pathway between a hepatic vein and a portal vein. The method comprises the steps of: advancing the telescoped system 1250 into the hepatic vein, as shown in FIG. 12A; steering the 10 Fr steerable sheath 1210 to aim towards the portal target, as shown in FIG. 12B. In some such examples, the step of steering the steerable sheath 1210 comprises active steering. The method additionally comprises: applying RF and advancing the RF guidewire 1240 into the portal vein, as shown in FIG. 12C; More specifically, the steerable sheath 1210 is actuated to aim the telescoping assembly 1250 in-situ along a desired trajectory, from within the hepatic vein towards the portal vein to orient the RF guidewire 1240 towards a desired target site within the portal vein to orient the RF guidewire 1240 towards a desired target site within the portal vein. The method additionally comprises: In one such example, the step of applying RF and advancing the RF guidewire 1240 comprises using the RF guidewire 1240 to puncture from the hepatic vein through a hepatic vessel wall, the liver parenchyma, and a portal vessel wall, to gain access from the hepatic vein into the portal vein. In some such embodiments, use of RF enables advancement of the RF guidewire in a controlled manner from the hepatic vein and into the portal through the liver parenchyma. The method then comprises confirming portal vein access, for example using techniques as outlined previously herein above; And after confirmation of the portal access (for example using techniques outlined herein above), advancing the telescoped assembly or system into the portal vein, as shown in FIG. 12D; removing all devices but the 10 Fr sheath, as shown in FIG. 12E, and guidewire to facilitate the rest of the procedure (for example, for stent deployment such as deployment of a GORE® VIATORR® TIPS Endo-prosthesis). As such, the example provided herein provides a telescoping assembly 1250 that function to aim the device therein from within the hepatic vein towards the portal vein to aim the RF guidewire towards the portal vein to provide a predictable trajectory, and enables creation of a channel between the hepatic and portal vein in a controlled manner using RF with application of minimal force and while minimizing damage to the vasculature and the liver tissue and while reducing the need for device exchanges.

As outlined above in Example 3A and Example 3B workflows, embodiments of the present invention provide advantages not known in the prior art. Specifically, the one or more methods provide for controlled advancement using RF with the use of an RF guidewire while providing enhanced aiming through use of a steerable sheath, while minimizing the number of device exchanges required in order to complete the procedure.

More specifically, as shown in examples 3A and 3B, the steerable sheath enables aiming of the telescoping system from within the hepatic vein towards the portal vein to aim the RF guidewire towards the portal vein to provide a predictable trajectory, and enables creation of a channel between the hepatic and portal vein in a controlled manner using RF with application of minimal force and while minimizing damage to the vasculature and the liver tissue and while reducing the need for device exchanges. In some examples, RF is applied in discrete steps. In another example, RF is applied in a continuous manner. In some such examples, the system of the present invention allows for controlled puncture and advancement of the telescoping assembly form the hepatic vein to the portal vein while puncturing only one vessel wall of the portal vein to access the portal vein. This minimizes damage to the portal vessel wall and allows for a more predictable entry into the portal vein while reducing the number of passes required for gaining access into the portal vein. In other words the system of the present invention may help reduce the time required to gain access into the portal vein.

Still furthermore, examples of a method of the present invention provides for advancing a steerable sheath down into the hepatic vein. This enables enhanced aiming capabilities. The steerable sheath provides a flexible distal tip which can actuated to achieve the required curvature or turn to enter further or in other words, deeper into the hepatic vein than a conventional stiff needle, which may only be capable of limited advancement into the hepatic vein due to its rigid curve. In some examples of the prior art, the needle may only be able to advance about 2-3 cm into the hepatic vein. Furthermore, during aiming, the tip of the steerable sheath may angled 'in situ', in addition to being torqued in order to aim directly at the portal vein, which provides an additional advantage over a conventional needle, which may only be torqued, severely limiting the extent to which the physician is able to aim the needle towards the intended target within the portal vein.

The method of the present invention additionally provides for the use of radiofrequency puncture. In contrast a conventional TIPS procedure utilizes a mechanical puncturing technique, which requires a rigid stiff needle in order to advance to the portal vein target. The conventional techniques require the needle to be advanced in a single push which requires extra force to be applied to enable advancement through damaged or cirrhotic liver tissue. Contrary to this, the RF guidewire of the present invention allows for controlled speed and depth of advancement while incurring minimal resistance.

More specifically, examples of the present invention provide for minimization and optimization of the number of device exchanges. More specifically, in example workflow 3A, a 7 Fr steerable sheath is provided as outlined above, that is advanced inside a 10 Fr introducer sheath which is required for the stent delivery after portal access has been obtained. This allows the entire procedure to be streamlined and to minimize device exchanges.

Alternatively, in example workflow 3B, after portal access has been obtained and the 10 Fr steerable sheath has been advanced into the portal vein, the distal portion of 10 Fr steerable sheath remains within the portal vein and the 10 Fr steerable sheath functions as an introducer sheath for the stent delivery. This also allows the entire procedure to be streamlined and to minimize device exchanges.

In some embodiments outlined herein above, the RF guidewire is advanced in a controlled manner in a single step towards a desired target location within the portal vein. Alternatively, the RF guidewire is advanced in several discrete steps towards at desired target site within the portal vein under the application of RF while confirming the trajectory under imaging. In some such examples outlined herein above the RF guidewire is a by Baylis Medical Company Inc. is used, and as disclosed in application referenced herein above, which is previously incorporated herein by reference in its entirety.

Alternatively, a method of the present invention allows for completion of a Direct Intrahepatic Portocaval Shunt procedure (DIPS) procedure. The method may involve a modification of any of the methods described herein, in that access may be obtained from jugular vein and all device may be advanced from the jugular vein down to the inferior vena cava to a point where they are close to the portal vein. The remainder of the procedure may be similar to the methods described herein as aiming, puncture and device advancement may be performed in a similar manner to a TIPS procedure as described herein. As mentioned above, the difference may be that a TIPS procedure is performed from the hepatic vein to the portal vein, and a DIPS procedure is performed from the IVC to the porta vein. As such, any of the TIPS solutions described herein may also be used fora DIPS procedure.

Confirmation of Portal Vein Access

As outlined for embodiments described previously, the physician may then confirm if the portal vein has been accessed. Portal vein access can be confirmed using methods previously described.

Similar to previous embodiments, once portal vein access is confirmed, the present method additionally comprises advancing the supporting catheter further into the portal vein and inserting a stiff guidewire to facilitate the rest of the procedure. Alternatively, the core wire may be re-inserted and may be re-advanced into portal vein and may be advanced further therein to maintain access and facilitate the remainder of the TIPS procedure.

In some embodiments, the RF guidewire may be the PowerWire RF guidewire (Baylis Medical Company Inc.) Further embodiments of exemplary guidewires that may be suitable for the methods described herein are described in greater detail in application Ser. No. 12/926,292, US 2011/0118735A1, previously incorporated herein by reference. In some embodiments, a crossing catheter is used. In some such embodiments the crossing catheter may be Cook CXI® Support Catheter (Cook Medical). In other embodiments, any other suitable RF guidewire and crossing catheter combination may be used. The support catheter and the RF guidewire may be locked together or otherwise coupled by, for example, a Tuohy-Borst adapter to form an RF guidewire catheter assembly to allow for concurrent advancement of the guidewire and catheter. In some such examples, a smooth transition is provided between the RF guidewire and the crossing catheter such that the outer diameter (OD) profile is not substantially larger than that of the RF guidewire. In some such examples, the smooth transition allows the distal edge of the crossing catheter to cross through the hepatic vein wall with relative ease. The smooth advancement of the crossing catheter additionally allows for smooth advancement of the RF guidewire as the RF guidewire is attached to the crossing catheter via the Tuohy-Borst adapter. As such, the RF guidewire catheter assembly formed by the RF guidewire and the crossing catheter can be advanced with relative ease as RF is applied to create the tract or passage between the hepatic and portal veins.

In some such embodiments, the RF guidewire comprises a single RF electrode. In other examples, the RF guidewire may comprise a patterned electrode or multiple electrodes. In some embodiments described above, the supporting catheter, such as a crossing catheter, is configured to mate or couple well to the RF guidewire, including having sufficient pushability and a suitable distal transition with the RF guidewire. In some embodiments, the support catheter of the RF guidewire catheter assembly, such as a crossing catheter, may be a dilator. In further embodiments, the crossing catheter may comprise another device that defines a lumen there-through and allows dilation of the tract or passageway created by the RF guidewire. In some embodiments, as outlined herein above, a selection of fixed curve sheaths may be utilized instead of the steerable sheath. In a further alternative embodiment, an RF needle may be utilized instead of an RF guidewire. In one example, the RF needle comprises a flexible RF needle. The use of an RF needle, as outlined previously, may help solve the problems that are observed during the use of mechanical device in procedures requiring the creation of transvascular pathways such as TIPS procedure, as the use of mechanical devices may lead to the need for applying excessive force in order to cross through tough tissues. The RF needle allows for application of RF in order to cross tough tissues which may allow for controlled advancement of the RF needle through the tissue.

Embodiments of RF Guidewire Catheter Assemblies

Example 1

Figure 6A:
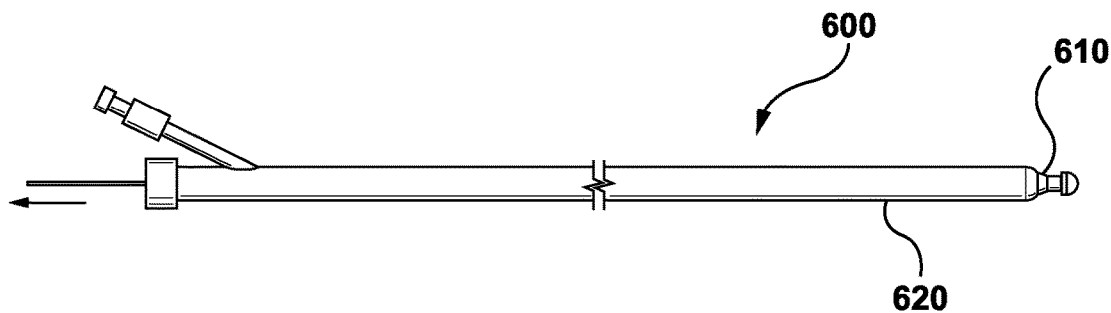
FIGS. 6A-6B are illustrations of a flexible RF puncture device comprising an RF guidewire catheter assembly, the assembly comprising a catheter having a single lumen device design and an RF guidewire disposed therein, in accordance with an embodiment of the present invention.
Figure 6B:
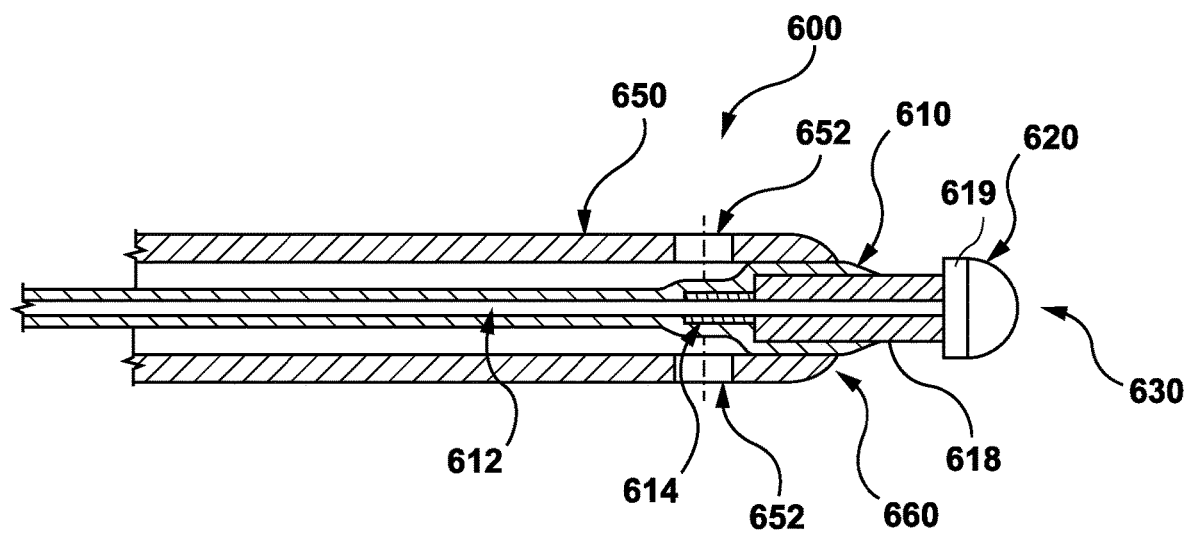
Figure 6C:
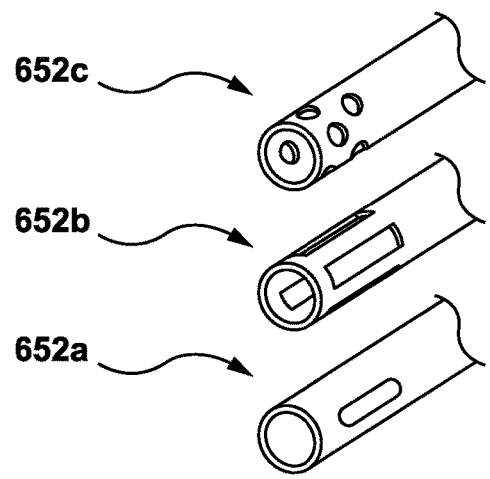
FIG. 6C is an illustration of alternate embodiments of side ports of the catheter of FIGS. 6A-6B, in accordance with an alternative embodiments of the present invention.

In an embodiment of the present invention as shown in FIGS. 6A, 6B and 6C, an RF guidewire catheter assembly 600 is shown for facilitating a Transjugular Intrahepatic Portosystemic Shunt Procedure comprising an RF guidewire 610 and an accompanying catheter 650 with one or more side ports 652 at its distal end. The RF guidewire 610 is connected to an RF supply using a connection means at the proximal end. In some examples, the RF guidewire is removable from the catheter upon disassembly. In some such examples, the guidewire catheter assembly 600 comprises a locking mechanism to lock the position of the RF guidewire 610 within the catheter 650. The RF guidewire catheter assembly 600 may additionally comprise a luer lock. The RF guidewire 610 comprises a core wire 612 such as an insulated core-wire with an RF electrode 620 at the distal end [for example formed on a tantalum puck 619], for example at the distal tip 630, as well as a platinum band 614 proximal to the heat shield 618, which is positioned proximally to the RF electrode.

In one specific example the RF guidewire is an RF guidewire as sold by Baylis Medical Company Inc., and as disclosed in application number referenced herein above, which is previously incorporated herein by reference in its entirety. The body shaft of the core wire 612 has an outer diameter that is smaller than the lumen of the catheter 650, conserving the ability to inject and withdraw fluid through the side ports. Furthermore, the OD of the distal tip of the core wire of the RF guidewire 610 fits tightly with the ID of the distal tip 660 of the catheter. In other words, an outer diameter along the distal tip of the core wire 612 being positioned with force fit engagement within with an inner diameter of the distal tip of the catheter 650. This forms a smooth profile of the RF guidewire catheter assembly 600. Additionally, the RF guidewire 610 comprising the core wire 612, can be removed from the catheter 650 when disassembled. As outlined for RF catheter embodiments described previously, the distal tip of the RF guidewire 610 forming the RF guidewire catheter assembly 600 can be either straight or curved, forming a straight distal tip or conversely a curved distal tip. In some embodiments, the one or more side ports 652 may comprise one or more openings that may be of various, sizes, shapes and configurations as shown in FIG. 6c. More specifically, FIG. 6c illustrates a single side port 652a, with an oval window forming an oval side-port, two or more rectangular side ports 652b, and multiple round or circular side ports 652c, positioned near the catheter 650 distal end.

In one specific example, the inner lumen of the catheter 650 may be maximized so it is as large as possible and the outer diameter of the core wire may be minimized so it is as thin as possible while still retaining enough lateral support to prevent buckling inside the catheter 650 once pressure is applied at the tip. In one specific example, a constant 0.010" wire with a 0.004" thick layer of PTFE presents the best compromise between lumen size (and in turn flow rate) and stiffness. Also, the transition between the core wire's tip and the catheter is smooth, with a snug fit and good taper. Furthermore, the proximal end has a locking mechanism such as a Tuohy-Borst adapter to secure the RF guidewire 610 and as such the core wire in place during advancement, and additionally comprises a luer lock for contrast injection/aspiration.

Example 2

Figure 7A:
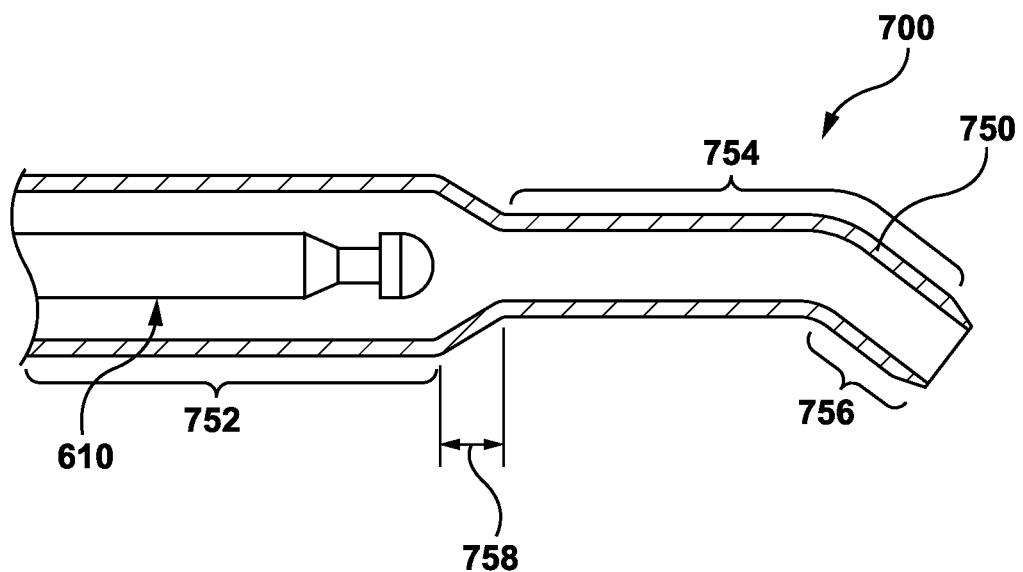
FIGS. 7A-7B are illustrations of an alternate embodiment of a flexible RF puncture device comprising an RF guidewire catheter assembly in use, the assembly comprising a catheter having a tapered-lumen device design for accommodating an RF guidewire therein, in accordance with an alternate embodiment of the present invention.
Figure 7B:
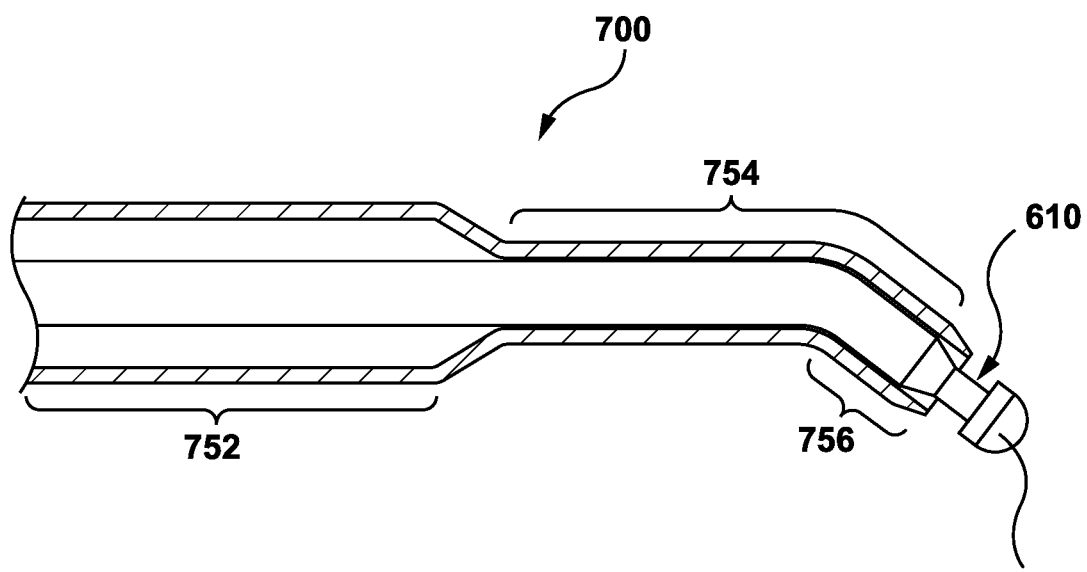

In another embodiment of the present invention, an RF catheter assembly for facilitating a Transjugular Portosystemic Shunt procedure is disclosed. As shown in FIGS. 7A and 7B, an RF guidewire catheter assembly 700 is disclosed that is formed by a regular RF guidewire 610 paired with a tapered-lumen catheter 750. The RF guidewire may be an RF guidewire sold by Baylis Medical Company Inc. and disclosed in application referenced herein above, which is previously incorporated herein by reference in its entirety. More specifically, the RF guidewire may comprise an insulated core-wire with an RF electrode at a distal tip, and a platinum band for supporting a heat shield positioned proximally to the RF electrode, the RF guidewire comprising a connection means at a proximal end for connecting to an RF supply, RF guidewire being removable from the catheter upon disassembly. In one example, the catheter lumen section is about 4 Fr-7 Fr in size. In one such example, proximal lumen section 752 is about 6-7 Fr in size and the distal lumen section is about 4-5 Fr in size. In some such examples, the tapered-lumen catheter 750 comprises a proximal lumen section 752 and a distal lumen section 754. In some such examples, the inner diameter of the proximal lumen section 752 is greater than or relatively larger than an inner diameter of the distal lumen section 754, and wherein the proximal lumen section 752 tapers down along a taper to the distal lumen section 754 to allow an RF guidewire to be positioned flush within the catheter along the distal lumen section 754. In one specific examples, the proximal lumen section 752 has an internal diameter of greater than about (>0.035") which facilitates contrast injection when the RF guidewire is withdrawn to the proximal lumen section 752, leaving enough lumen space for sufficient flow rate. I one such example the distal lumen section 754 is about 4 Fr to about 5 Fr in size and extends along a distance of between about 4 cm to about 8 cm. In other words, the tapered-lumen catheter allows for the RF guidewire to be retracted to the proximal lumen section 752 to allow for fluid injection or aspiration. The catheter lumen tapers down from the proximal lumen section 752 along a taper 758 to become flush with the RF guidewire 610 along the distal lumen section 750 for example along the distal 4 cm-8 cm of the catheter 750. This keeps the distal end of the catheter 750 at a minimum OD so that the tract created by RF cutting does not get dilated more than necessary. As outlined previously, the distal tip 756 of the RF catheter assembly 700 can be either straight or curved.

Example 3

Figure 8A:
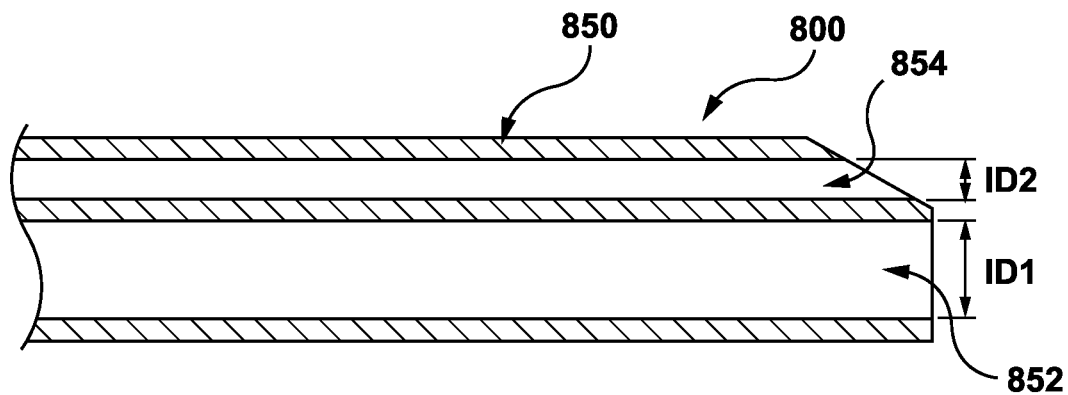
FIG. 8A is an illustration of an alternate embodiment of a flexible RF puncture device comprising an RF guidewire catheter assembly, the assembly comprising a catheter having a dual-lumen device design, in accordance with an alternate embodiment of the present invention.
Figure 8B:
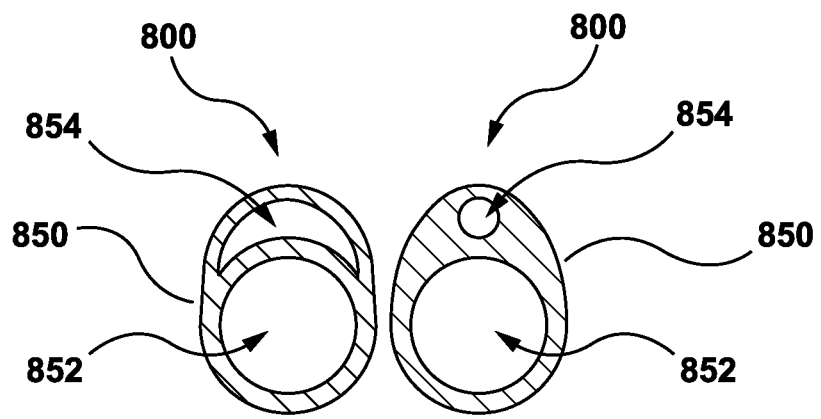
FIG. 8B shows cross-sectional views of alternative embodiments of the RF guidewire catheter assembly of FIG. 8A, in accordance with alternative embodiments of the present invention.
Figure 8C:
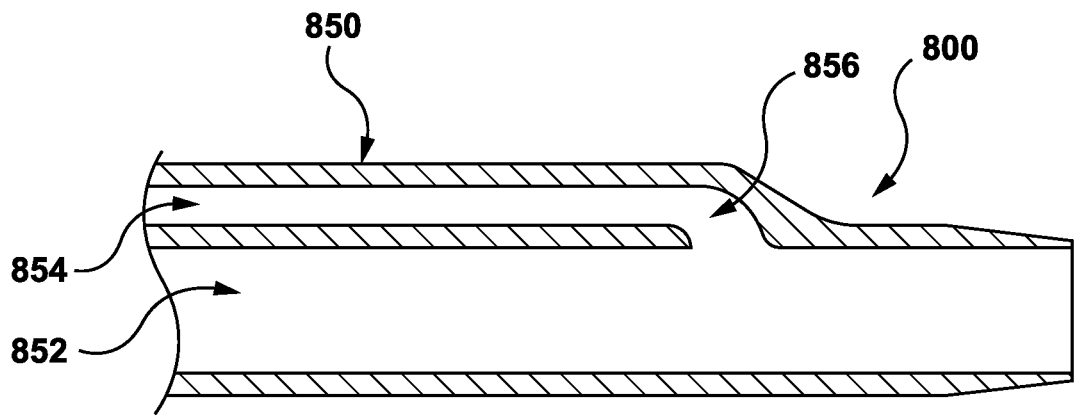
FIG. 8C is an illustration of an alternate embodiment of a flexible RF puncture device comprising an RF guidewire catheter assembly, the assembly comprising a catheter having a dual-lumen device design, in accordance with a further alternative of the present invention.

In still a further alternative embodiment, as shown in FIGS. 8A, 8B and 8C, an RF guidewire catheter assembly 800 is disclosed that comprises a regular RF guidewire that is paired with a dual-lumen 5 Fr-7 Fr catheter 850. The dual lumen catheter 850 comprises a primary lumen 852 that is used for device exchange and a smaller secondary lumen is used for contrast injection. In one such example, the primary lumen 852 has an inner diameter ID1 of between about 0.035"-0.038". In the first alternative, as shown in FIGS. 8A and 8B, contrast can be injected at any time, since the secondary lumen 854 is open at the distal end and has an inner diameter ID2 that is sufficient for allowing delivery of fluids and/or aspiration. In embodiments utilizing the alternative design shown in FIG. 8C, the junction 856 between the two lumens, the primary lumen 852 and the secondary lumen 854, is internal to the catheter 850. In one such example, the RF guidewire may be retracted proximal to the junction 756 between the two lumens to allow for fluid injection. The catheter of FIG. 8C may additionally prevent occlusion of the secondary lumen 854 during device advancement, as the opening to the secondary lumen 854 is not exposed to the surrounding environment during advancement but is rather in communication with the primary lumen 852 at the distal end of the secondary lumen 854.

In some examples of the embodiments illustrated in FIGS. 7A-8C, a smooth tapered transition is provided from the tip of the RF guidewire 610 to the catheter 750, 850, as well as a Tuohy-Borst and Luer lock at a proximal portion of the catheter (not shown). In some embodiments of devices as shown in FIGS. 7A-7C, the proximal lumen 752 of the RF guidewire catheter assembly 700 has a relatively large lumen, allowing for the maximum flow rate possible given the vasculature and other anatomy within which the catheter 750 will be positioned/advanced. Similarly, in some examples of the RF guidewire catheter assembly 800 shown in FIGS. 8A-8C, the primary lumen 852 which is the device exchange lumen is sized to be substantially snug to the RF guidewire, for example an RF guidewire such as an (0.035") guidewire while the secondary lumen 854 is made as large as can be accommodated given the nature of the procedure. In an alternative embodiment, the catheter 850 features an over-the-wire proximal end, allowing for easier device exchange.

In some embodiments, for example those utilizing a core wire, once RF puncture has been performed and access has been confirmed, the core wire can be removed, leaving behind the catheter 750, 850 for device exchange. In some such embodiments the RF electrode can be patterned to do selective arcing. In some embodiments, the catheter 750, 850 of the RF guidewire catheter assembly 700, 800 is compatible with a 0.035" RF guidewire, or alternatively with a 0.038" RF guidewire 610. In a further alternative, the RF guidewire catheter assembly 700, 800 provides a catheter 750, 850 that is compatible with a 0.018" RF guidewire 610.

In alternate embodiments of the present invention, the RF guidewire 610 and support catheter 750, 850, or in other words the RF guidewire catheter assembly 700, 800, may be replaced by an RF catheter that has an electrode for delivery of RF and a lumen and port for aspiration and/or delivery of contrast. In some such embodiments, the RF catheter is provided as a single device that allows for RF cutting, aspiration and/or delivery or contrast injection and device exchange in order to minimize the number of devices required to complete the procedure. This may reduce the number of devices that are to be handled by the physician or user during the procedure.

In some examples the RF catheter may comprise a side port as outlined previously. In other examples, the RF catheter may comprise a front port. Similar to embodiments described for the RF guidewire, in embodiments that utilize an RF catheter, the RF catheter may comprise a single electrode. Alternatively, the RF catheter may comprise a patterned electrode or multiple electrodes.

RF Catheter and Steerable Sheath

In accordance with an additional embodiment of the present invention, a system and method are provided comprising a flexible system that can navigate tortuous anatomy and effectively aim at the portal vein target.

In one such embodiment, a system and method are disclosed for performing a TIPS procedure, the system comprising a flexible RF catheter for creating a tract or passage from the hepatic vein to the portal vein and a steerable guiding sheath for navigating through tortuous anatomy for aiming and directing the flexible RF catheter. The steerable sheath and RF catheter combination allows for accessing the hepatic vein, allows for the assembly to be aimed at the portal vein target, and enables puncture through the hepatic vessel wall, the liver tissue, and the portal vessel wall by applying RF through the RF catheter while complying to the anatomy with minimal mechanical resistance. In some embodiments the assembly comprises a steerable sheath that allows for in-situ angle adjustment for gaining access to the hepatic vein and aiming, and an RF catheter to enable RF cutting and to facilitate crossing, aspiration/contrast injection, and device exchange.

Example 1 Workflow

Figure 9:
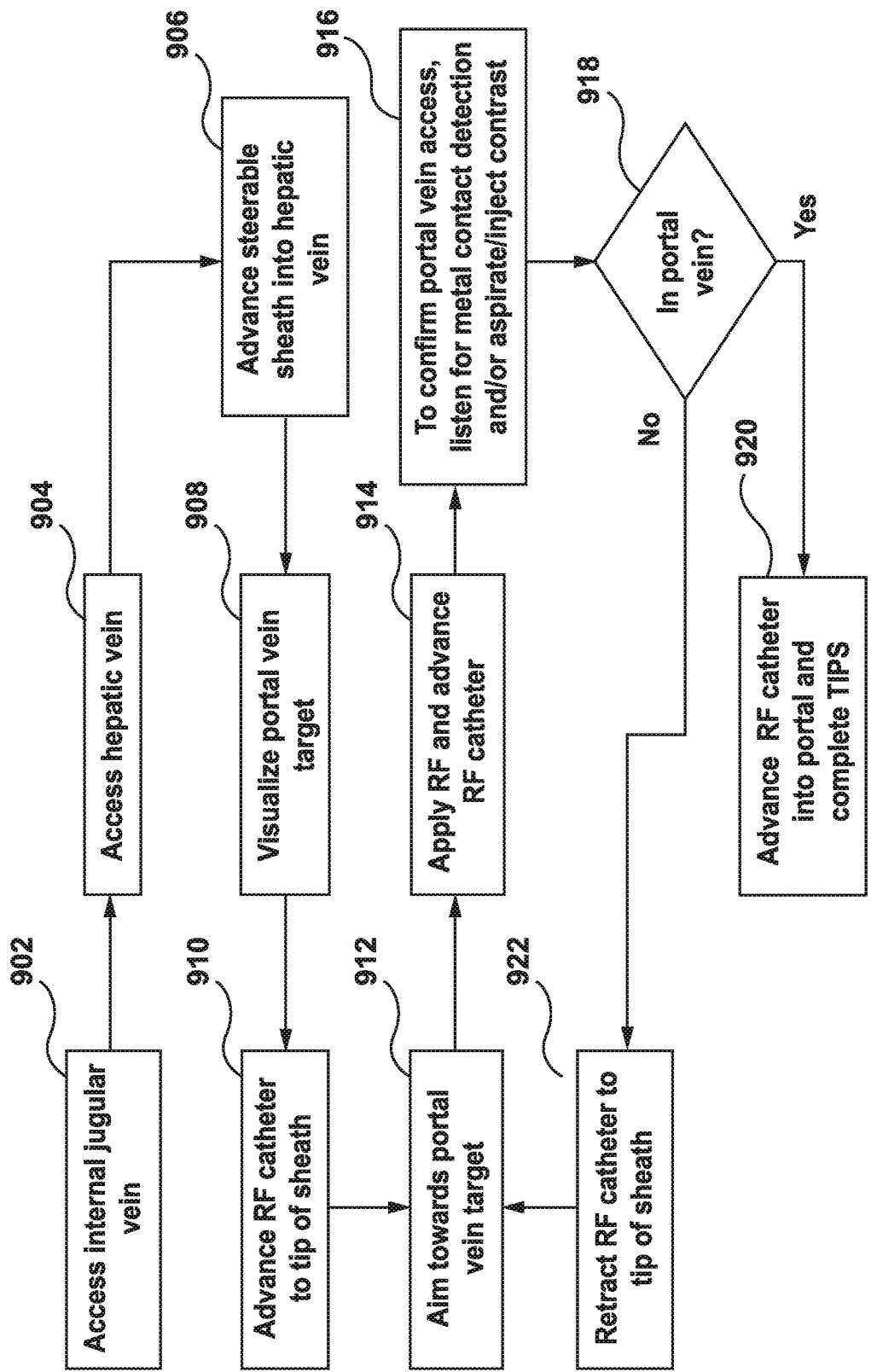
FIG. 9 is a flow diagram showing a method of performing a transvascular procedure using an RF catheter and a steerable sheath in accordance with still a further alternative embodiment of the present invention.

In accordance with an embodiment of the present invention, as shown in the flowchart illustrated FIG. 9, a system and method are disclosed for carrying out a TIPS procedure using an RF catheter and a steerable sheath. In accordance with a particular example, the steerable sheath is a commercial embodiment of a steerable sheath sold by Baylis Medical Company Inc., as described in further in application referenced herein above and previously incorporated by reference in its entirety. In one example, the method comprises the following steps: at step 902, gaining access to internal jugular vein or femoral vein using standard introducer kit; at step 904, gaining access to the hepatic vein with a guidewire and catheter via inferior vena cava; removing the catheter; at step 906, advancing the steerable sheath and dilator over the guidewire into the hepatic vein; removing the dilator and wire; and at step 908, visualizing the target portal vein using imaging techniques. In some such examples, the method may comprise visualizing the target portal vein using standard $CO_2$ angiography techniques, intravascular ultrasound techniques, or fluoroscopy. In a specific example, the step of visualizing the target portal vein may comprise inserting a target device (e.g. guidewire, catheter) into the portal vein to visualize the target portal vein. Alternatively, other imaging techniques may be used to visualize the target portal vein, as may be known in the art. The method additionally comprises the following steps: at step 910, advancing the RF catheter to tip of sheath, and at step 912, aiming towards the portal vein target. In some examples, this may involve, actuating the steerable sheath, for example, by rotating the knob on the steerable sheath handle, in order to permit in-situ aiming by for example, steering or angling the tip of the steerable sheath towards the portal vein or the target within the portal vein; advancing the RF catheter through the steerable sheath to the puncture site; connecting the RF catheter to an RF generator; applying RF; and at step 914, advancing the RF catheter through the liver parenchyma towards the portal vein or the target within the portal vein, the RF catheter enabling puncture through a wall of the hepatic vein, the liver parenchyma and a wall of the portal vein.

Confirmation of Portal Vein Access

As outlined for embodiments described previously, at step 916, the physician may then confirm if the portal vein has been accessed substantially in the manner described above. Access may be confirmed through one or more of various methods described herein. In one specific example, a method is provided whereby a metal target device (i.e. a guidewire) is placed in the portal vein to function as a portal vein target. In some examples the step of confirming portal vein access comprises assessing proximity to the target from the puncturing device. More specifically, as described for RF guidewire embodiments described herein above, as the RF catheter is advanced into the portal vein, it contacts the target device. A radiofrequency generator that is coupled to the RF catheter at is operable to generate or prompt a "Metal Detection" error, suggesting or indicating that the portal vein has been accessed. The procedure is described further in application referenced herein above and previously incorporated by reference in its entirety. The portal vein access can be further confirmed through aspiration. A method is provided to confirm portal vein access, whereby once the RF puncture has been performed and portal vein access is suspected, a syringe is connected to the RF catheter. The plunger of the syringe is then pulled back. If blood is withdrawn it provides an indication that a vessel has been successfully accessed. In order to confirm that the vessel is in fact the portal vein, contrast may be injected under fluoroscopy to observe the vessel under imaging. Alternatively, the step of confirming portal access may comprise using tactile feedback.

As step 918, it is determined if the portal vein has been accessed. At step 920, the remainder of the TIPS procedure may be completed once portal access has been confirmed. More specifically, the core wire can be advanced back into the portal vein and advanced further into the portal vein to maintain access and facilitate the rest of the TIPS procedure. Or in some embodiments, if desired, the RF catheter may be disassembled and the core wire may be removed. The supporting catheter may be advanced further into portal vein and a stiff guidewire may be inserted to facilitate the rest of the procedure. Alternatively, if at step 918, the portal vein has not been accessed, at step 922 the RF catheter can be retracted to the top of the sheath and steps 912 to 918 may be repeated to confirm portal vein access.

As such, some embodiments of the present invention provide a steerable sheath functions to RF catheter from within the hepatic vein along a desired trajectory towards a desired target site within the portal vein, wherein the RF catheter enables creation of a channel between the hepatic and portal vein in a controlled manner using RF with application of minimal force and while minimizing damage to the vasculature and the liver tissue and while reducing the need for device exchanges.

In some embodiments, the systems and methods of the present invention, including the present method utilizing an RF catheter, may be used for Transjugular Intrahepatic Portosystemic Shunt (TIPS) procedures and Direct Intrahepatic Portocaval Shunt (DIPS) procedures. In addition, the methods and systems of the present invention, including the method above utilizing an RF catheter, may be used in transvascular procedures for creating a fistula between two vessels. Furthermore, the systems and method/device combinations of the present invention may be used in other clinical procedures that requires navigation through tortuous anatomy and perforation of tissue (e.g. septum, occlusion).

In some embodiments of the present invention, a steerable sheath sold by Baylis medical Company Inc., Montreal, QC, Canada, may be used as described in application referenced previously and incorporated by reference in its entirely herein above. In one example the steerable sheath is of the short-shaft variety having a usable length of about 45 cm. This sheath may be useful in procedures where access is made through the internal jugular vein, which has a relatively short path to the liver compared to other access points. Use of this sheath ensures that a significant portion of the steerable sheath remains within the patient's body during use, so as not to hinder the use of the device by the physician when manipulating and torqueing the device during the procedure. In other embodiments the steerable sheath may be usable with internal jugular or femoral access points and may have a usable length that ranges from about 45 cm to about 71 cm.

In some embodiments, the steerable sheath has a relatively small radius of curvature, for example about 8.5 mm, and may facilitate steering within the vasculature. In alternative embodiments, the steerable sheath may have different radii of curvatures, for example between about 8.5 mm to about 25 mm. In some examples the radii of curvature may be 8.5 mm, 11 mm or 25 mm. In some examples the steerable sheath shaft may range from about 6 Fr to about 10 Fr. In other embodiments, the curve of the steerable sheath may be of different radii. In some examples the steerable sheath may be a bi-directional sheath or alternatively, the steerable sheath may be a unidirectional or one directional sheath. The sheath may include more than one curve where the curves are in one plane or in different planes.

In some embodiments of the present invention, a metal guidewire is placed in the portal vein to act as a target. There may be several benefits to using a target device in general, as well as pertaining to the particular method described above with respect to the RF catheter. For example, the portal vein may be constantly visible under fluoroscopy by visualizing the target device located therein, thereby limiting the need for contrast injection, which may speed up the procedure.

As a further benefit of this specific method, an RF generator may be used that includes a feature that prompts a "metal contact/low impedance" (or similar) error and ceases RF delivery whenever an RF device comes in contact with metal. This feature can be used as another avenue to confirm portal vein access if the device placed in the portal vein is indeed metal (i.e. a guidewire).

In some embodiments described herein above, the RF device (such as an RF guidewire or RF catheter) is advanced in a single step towards a desired target location within the portal vein. Alternatively, the RF device (such as an RF guidewire or RF catheter) may be advanced in several discrete steps towards the portal vein under the application of RF while confirming the trajectory under imaging.

In some embodiments, the methods described herein, including the method described herein above that utilizes an RF catheter, may also be used with other imaging techniques such as $CO_2$, DSA, angiography, or intravascular ultrasound. Furthermore, a contrast injection may be used as a visualization method, in addition to or alternative to other visualization methodologies. In some embodiments, a balloon may be placed on the RF catheter to allow for dilation of the tract and to facilitate $CO_2$ angiography. In a further alternative, an RF needle may be used instead of RF catheter. In one example, the RF needle comprises a flexible RF needle. As outlined previously, the use of an RF needle, may help solve the problems that are observed during the use of mechanical device in procedures requiring the creation of transvascular pathways such as TIPS procedure, as the use of mechanical devices may lead to the need for applying excessive force in order to cross through tough tissues. The RF needle allows for application of RF in order to cross tough tissues which may allow for controlled advancement of the RF needle through the tissue.

In further alternatives of the present invention as they relate to embodiments that utilize an RF catheter, the RF catheter may comprise a single electrode. Alternatively, the RF catheter may comprise a patterned electrode or multiple electrodes. The RF catheter may of the type as described previously herein.

Therefore, in accordance with some embodiments of the present invention, methods and systems are disclosed that use RF energy to traverse from the hepatic vein to the portal vein which additionally permit the use of flexible devices in conjunction with the use of radiofrequency energy in order to effectively perform transvascular procedures such as TIPS procedures while reducing the risk of damage to internal organs that may be present from use of conventional rigid devices and systems.

In some embodiments, the device combinations provided herein including RF catheter assemblies as well steerable sheath and RF guidewire combinations, may allow easy manipulation by a single operator. In further alternatives, in some embodiments utilizing an RF guidewire, a marker may be provided on the RF guidewire, such as an RF guidewire sold by Baylis Medical Company Inc., as described in application referenced herein above and previously incorporated by reference in its entirety. The marker for example to indicate the distal alignment with the crossing catheter, which may be desirable when they are being advanced together.

An example of a detailed study report of an Animal Study is provided herein below, where the following devices were utilized in an animal, specifically a pig:

I. $CO_2$ portogram for TIPS

1. Baseline: Rosch-Uchida Kit by Cook® Medical with A-P View Only:

The first test was used to set a baseline. As $CO_2$ portogram at A-P view was used for image guidance. A Standard Rosch-Uchida kit and work flow was used. The physician performed the navigation and aiming using the one view. Portal access was achieved using the standard procedural workflow. The testing time of this solution was roughly about ten minutes.

2. Rosch-Uchida Kit with PowerWire® RF Guidewire in Place of the Stylet

With the same imaging method and information, the Rosch-Uchida stylet was then replaced by a stiff PowerWire® RF guidewire. Constant 3s was used for arcing. In other words, power was on for 3s continuously to generate arcing. Portal access was achieved within 10 minutes from the first RF application. 3. Short curve steerable+CXI® support catheter by Cook® Medical+PowerWire® RF guidewire by Baylis Medical (Dual-plane)

In the present example, during imaging, both an AP view and a lateral view of the $CO_2$ portogram were obtained. The physician operated substantially under a roadmap mode at lateral view at first. In the roadmap mode, the outline of the portal vein was not showing. The physician operated by the guidance of landmarks. The PowerWire® RF guidewire was advanced and the CXI® support catheter followed. After two to three RF applications, contrast injection was used which indicated that the device was within a vessel. From the AP view, it was confirmed that the device had accessed the very distal end of the portal vein.

The physician then switched back to AP view with portogram as a reference to operate. The physician was utilizing the steerable sheath for positioning. At a second attempt with two RF applications, portal vein access was obtained. A repeat run was performed. The physician switched between the AP and lateral view frequently after each alignment and RF application to confirm whether the device was in the desired location. The two plane view enabled the physician to quickly and effectively confirm whether the device was in the correct area or not. With $CO_2$ portogram reference and constant verification under two views, the physician was able to obtain a clear view of the target and the device alignment to the target. Within two passes, the portal vein access was obtained again.

4. Short Curve SureFlex® Steerable Sheath+PowerCatheter™ RF Catheter

In another example an RF catheter is used in combination with a SureFlex® steerable sheath, such as a PowerCatheter™ RF Catheter was used with a short curve SureFlex® steerable sheath both by Baylis Medical Company Inc. Both AP and lateral view were used for imaging guidance. The PowerCatheter™ RF catheter provides an advantage of providing instant aspiration/contrast injection without swapping the wire out. The PowerCatheter™ RF catheter enables wire advancement immediately after portal access confirmation. It also allowed for aspiration using negative pressure using a syringe during arcing, where portal access can be indicated instantly by constant blood flow back to the syringe.

In one such example, the PowerCatheter™ RF catheter is provided with a side port that is positioned further back from the electrode and is enlarged to help prevent or minimize blockage from tissue buildup on the side ports of the PowerCatheter™ RF catheter, which may prevent sufficient aspiration. In one example of an RF Catheter Assembly such as the PowerCatheter™ RF catheter, the RF guidewire and the catheter are locked at their proximal end to prevent movement between the electrode and the distal end of the catheter. This may prevent the electrode of the RF guidewire from being positioned within the catheter or very close to the catheter distal during arcing, in order to minimize catheter damage, for example after multiple uses.

II. IVUS

5. TIPS with Rosch-Uchida as Baseline

In another example, a TIPS or DIPS procedure may be performed with an IVUS imaging technique. In one such example, femoral access was used to advance the IVUS catheter into the IVC. A transducer for the IVUS technique was placed between the portal vein and hepatic vein so both can be visualized at the same time. A standard Rosch-Uchida kit was used as a baseline. By adjusting the transducer plane, the tip of the cannula could be visualized and aligned to the target. The needle could also be visualized, as it advanced towards the portal target. Once the needle was in the portal, the needle tip and the portal vein outline were overlapped on the imaging. The portal access was then confirmed by aspiration and contrast injection. Bubbles would show under ultrasound during injection. Wire advancement into the portal vein could also be visualized on the IVUS.

6. TIPS with Rosch-Uchida Catheter+PowerWire® RF Guidewire (Stiff and Flex Versions)

In one specific example, the combination of a Rosch-Uchida catheter by Cook® Medical and a stiff PowerWire® RF guidewire was used. The PowerWire® RF guidewire was echogenic and could be well visualized using the IVUS imaging technique. Portal access was successfully achieved within two RF applications. Confirmation of portal access was obtained by observing the IVUS screen which showed that the wire was in the portal vein. The physician then attempted to advance the PowerWire® RF guidewire further into the portal vein to act as an exchange wire. It was found that the distal end of the wire was too stiff to make a turn into the portal vein. A Flex PowerWire® RF guidewire was swapped in and the physician easily advanced it deep into the portal vein.

7. DIPS with Large Curve SureFlex® Steerable Sheath+CXI® Support Catheter by Cook Medical+Flex PowerWire® RF Guidewire Additionally a large curve SureFlex® steerable sheath with CXI® Support Catheter and flex PowerWire® RF guidewire combination was used for a DIPS procedure. The CXI® Support Catheter and the PowerWire® RF guidewire were locked by Tuohy-Borst connector and advanced together. In some such examples, a mark may be provided on the RF guidewire to facilitate quick alignment at the distal tip of the RF guidewire and the support catheter. In the specific example, the physician did not feel any resistance during advancement of the assembly due to the soft nature of the healthy pig liver. Alternatively, some resistance may be observed during traversal through a cirrhotic liver. In the specific example discussed, the devices used showed good visibility from aiming in the hepatic, to advancing in the parenchyma and to accessing the portal vein. The use of the steerable sheath allows for minor aiming adjustments immediately within the liver.

8. TIPS with Large Curve SureFlex® Steerable Sheath+CXI® Support Catheter+Flex PowerWire® RF Guidewire In another example, the same device combination as above was used for a TIPS procedure. The solution showed good repeatability and success for TIPS procedure under IVUS guidance as well.

9. TIPS with Large Curve Steerable Sheath+CXI+Angled Flex PowerWire RF Guidewire In still a further example, the same device combination as above was used for a TIPS procedure with the Flex PowerWire® RF guidewire was replaced with an angled Flex PowerWire RF guidewire. The solution showed good repeatability and success for TIPS procedure under IVUS guidance as well.

10. DIPS with Large Curve Steerable Sheath+Quick-Cross+Angled Flex PowerWire® RF Guidewire.

A DIPS procedure was performed, similar to the example described herein above with a large curve SureFlex® steerable sheath+CXI® Support Catheter by Cook Medical+Flex PowerWire® RF guidewire. In the present example, the CXI® Support Catheter was replaced with a Quick-cross Catheter, and similar results were achieved, 11. DIPS with Large Curve Steerable Sheath+(Catheter)+Angled Flex PowerWire® RF Guidewire.

In still another example, a DIPS procedure was performed, similar to the above example, where the Quick-cross catheter was replaced with a catheter by Baylis Medical Company Inc.

In still a further example, using a second animal, examples 9-11 were performed to assess the repeatability of the solution under IVUS and different crossing catheters were evaluated. In one example, a CXI® support catheter was used which performed well using the present solution. The slight angle of the Angled Flex PowerWire® RF guidewire, allowed the physician to easily advance the RF guidewire deep into the portal vein once the access was confirmed.

As outlined in examples described herein above, a successful animal study was conducted and effectiveness of the solutions presented herein were confirmed when working with both $CO_2$ portogram and IVUS.

In some embodiments described herein above, the use of RF cutting in combination with IVUS allows for controlled advancement. The present solution involving RF cutting has advantage over the current solutions in cirrhotic liver cutting or patient with portal vein thrombosis. In some examples the system provided herein provide an advantage of instant portal vein access confirmation without conducting extra steps such as withdrawing the wire such as the RF guidewire. Some examples provided herein would additionally allow a single operator to conduct the procedure.

In additional examples, the length of the devices in the same kit may be optimized for easy handling. Furthermore, using a crossing catheter such as a support catheter, a system may allow the RF electrode to protrude distally from the catheter by a length to avoid damage to the catheter due to arcing. In some such examples, the steerable sheath may be provided with a handle that is light for easier handling.

Reference is now made to previous Example 2 using Rosch-Uchida kit with PowerWire® RF guidewire in place of the stylet. In some such examples, the use of an RF guidewire may provide a benefit over a stylet in a dense liver or when ascites present. In some embodiments, the use of an RF guidewire may provide a tactile feedback as the wire enters the portal vein. In other examples, the use of an RF guidewire may be provide minimal or no tactile feedback as the wire enters into the portal vein. Furthermore, the use of an RF guidewire in combination with a catheter or steerable sheath may avoid tissue buildup at the tip which may be observed with the use of standard systems such as the Rosch-Uchida catheter.

In another example, a short curve SureFlex® Steerable Sheath+CXI® Support Catheter+PowerWire® RF guidewire may be provided (using a Gun-Barrel plane view). In other words, a gun-barrel approach may be used. The C-arm may be rotated to achieve the gun-barrel view plane where the hepatic and portal veins are substantially on top of one another in the view. The C-arm may be rotated between the maximum rotating range of the C-arm in order to achieve the gun-barrel view. In some examples, the gun-barrel view plane may be used as a second option when a standard imaging technique has failed.

In accordance with a specific example of a method of the present invention utilizing a steerable sheath and an RF device such as an RF guidewire, an imaging technique utilizing a $CO_2$ portogram is used. The method may additionally utilize techniques as outlined herein directed to Medical Imaging Methods for TransVascular Procedures. The physician is able to readily identify device orientation through the handle of the steerable sheath and no significant difference is observed in comparison to conventional tools in terms of handling. In a specific instance of this example, a method of using a dual lane $CO_2$ in combination with fluoroscopy may provide enhanced imaging guidance information than single plane fluoroscopy view. In some such embodiments, a gun-barrel view may be utilized to aim and target at the portal vein.

In other examples, IVUS imaging techniques may be used, as outlined in more detail herein below. Similar to examples described herein a steerable sheath in conjunction with an RF device, such as an RF guidewire may be used in order to complete a TIPS or a DIPS procedure under IVUS imaging guidance. In some such examples, the steerable sheath is flexible and may allow for precise 'in-situ' aiming adjustment which may provide an advantage over a stiff cannula with a fixed angle. Furthermore, the use of RF may allow for controlled advancement that enables real time position verification under IVUS. In some such examples, the RF guidewire may be the PowerWire® RF guidewire sold by the Baylis Medical Company Inc., and the steerable sheath may be the SureFlex® steerable sheath, also sold by the Baylis Medical Company Inc. The SureFlex® steerable sheath and PowerWire® are echogenic and provide good visibility under IVUS. Furthermore, in some examples a flexible PowerWire® with a slight angle may be preferred by a physician as it allows for immediate advancement into the portal vein after access confirmation. Furthermore, in one such example, IVUS allows visualization of the target [such as the portal vein target] and device in a single plane, which enables real-time device alignment and advancement control. In other examples, any other RF guidewire and steerable sheath combination may be used that provide these functionalities.

In examples described herein, the use of RF to cut or puncture, add value when going through a cirrhotic liver as it may reduce the amount of force required to puncture and cross the liver as may be seen with mechanical puncture. Furthermore, a telescoping system may provide an additional advantage where the devices in a kit may be advanced in sequence.

In accordance with an embodiment of the present invention, the use of RF in puncture or cutting adds value when puncturing through a cirrhotic liver as it reduces the amount of force required to puncture in comparison to the use of mechanical puncturing techniques, which may require a lot of force to go through the liver.

Medical Imaging Methods for Transvascular Procedures

In one example, a method is provided that improves upon the work flow of the current $CO_2$ DSA procedure, for example by adding a second view plane. Generally, an imaging method is provided that provides a dual plane view with $CO_2$ DSA. It provides a way to mark and keep track of different fluoroscopic view positions, allowing the physician to easily and reliably switch between orientations without having to reconfirm the position of the target vein. Imaging methods outlined herein may be used with any procedure that requires DSA or similar techniques with $CO_2$ or any other types of contrast. As such, the present invention provides an imaging solution that provides the physician with (three-dimensional) 3D information of the anatomy while additionally allowing for greater flexibility. In one example, the present invention provides for using a (two-dimensional) 2D imaging system to provide 3D information about a target anatomy such as one or more target vessels.

In one embodiment of the present invention, the method typically includes multiple injections of $CO_2$ to mark the fluoro position and create an anatomy roadmap.

In certain embodiments, the method of the present invention is performed using one or more of the following devices/equipment: a $CO_2$ tank, a $CO_2$ delivery system, a C-arm fluoroscopy system with DSA capabilities, an occlusion balloon catheter, transparencies, and various different color markers/pens.

In some embodiments, the present invention provides methods for visualizing the vasculature during a transvascular procedure. In a specific example, a method is disclosed that provides an imaging technique that is usable to image vasculature, such as the hepatic and portal veins, in a Transvascular Intrahepatic portosystemic Shunt (TIPS) procedure. In some such examples, the method is specifically geared towards visualization of the portal vein in order to facilitate the procedure.

Figure 13:
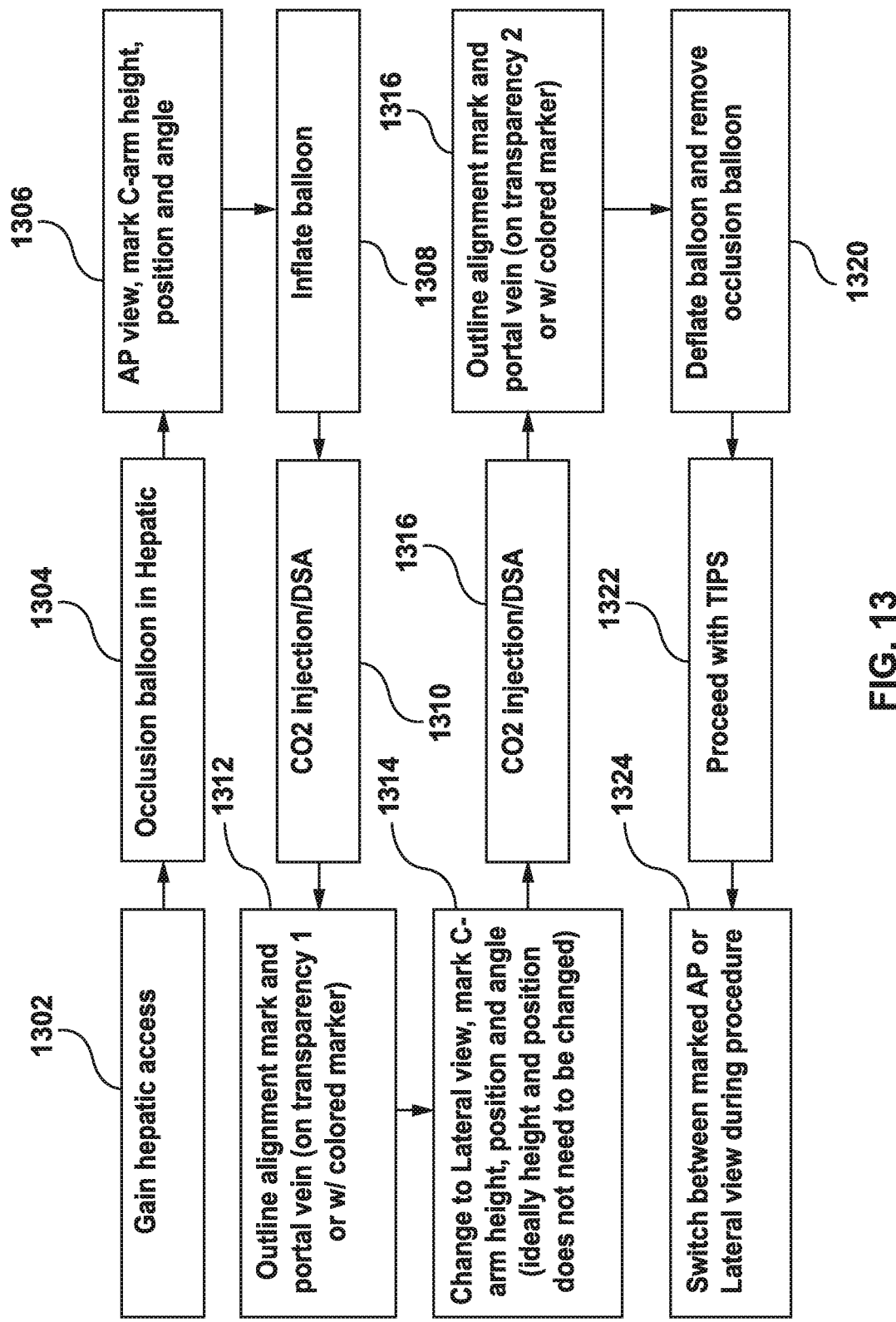
FIG. 13 is a flow diagram showing an imaging method to facilitate a TIPS procedure in accordance with an embodiment of the present invention.

In one example of the present invention, as shown in the flowchart of FIG. 13, an imaging method is disclosed for carrying out a transvascular procedure such as a TIPS procedure. In other embodiments, the methods disclosed herein may be utilized to carry out other transvascular procedures such as Direct Intrahepatic Portocaval Shunt (DIPS) procedures, and any other procedures that include puncture and aspiration/injection/device exchange, such as transseptal procedures. The methods of the present invention may be used in procedures requiring the creation of a fistula between structures such as vessels and/or other organs.

In accordance with some embodiments of the present invention, and as partially illustrated in FIG. 13, an imaging method is provided comprising the following steps: gaining access to the internal jugular vein or femoral vein using standard introducer kit; at step 1302 gaining access to the hepatic vein with a guidewire and catheter via inferior vena cava; removing the catheter; at step 1304, advancing an occlusion balloon catheter over the guidewire into the hepatic vein; at step 1306, ensuring that the C-arm imager is set to AP view and DSA mode; noting the C-arm height, position, and angle; at step 1308, inflating the balloon with saline or contrast solution; removing the guidewire; filling the $CO_2$ delivery system with $CO_2$ gas; at step 1310, connecting the $CO_2$ delivery system to the balloon catheter; under active fluoroscopy in DSA mode, injecting $CO_2$ to see hepatic and portal vasculature; saving the fluoro image; at step 1312, using a transparency and marker, outlining the portal vein target and alignment mark from the fluoroscope screen; at step 1314, switching the C-arm orientation to lateral view (or any other view), noting height, position, and angle; at step 1316, under active fluoroscopy in DSA mode, injecting $CO_2$ to see hepatic and portal vasculature; saving the fluoro image; at step 1318, using a new transparency with a different colored marker, outlining the portal vein target and alignment mark. In one example the same transparency may be used. The method additionally comprises the steps of: at step 1320, deflating and removing the balloon catheter; and at steps 1322 and 1324 with transparencies and documented C-arm positions as reference points, freely switching between views to complete the TIPS procedure. Alternatively, instead of transparencies and markers, one can also use the roadmap function of the fluoroscopy system to overlay with previously saved images which have the portal vein outlined.

In alternative embodiments of the present invention, instead of a $CO_2$ injection, any other type of suitable contrast may be used and injected. In some examples a balloon may be used that allows the contrast to be retained in the area being imaged to facilitate the process. Furthermore, instead of utilizing two different views, there can be more than two viewing planes. A similar work flow applies to each viewing plane. Additionally, in some alternative embodiments, instead of marking the C-arm position(s), the method includes recording the positions and automatically returning to the previously saved positions. Still furthermore, in additional embodiments, rather than outlining the portal vein on a transparency or fluoro screen, a roadmap function that is available on some fluoro machines is used to provide the same functionality.

The present inventors have thus discovered a novel method that provides an imaging solution that generates a reference image of the vasculature, such as the portal vein, under at least two different viewing planes with $CO_2$ DSA. This method provides the physician 3D information of the anatomy for carrying out a transvascular procedure such as a TIPS procedure and allows for some flexibility in the imaging portion of the procedure. Therefore, in accordance with an embodiment of the present invention, a medical imaging method is disclosed which provides the physician with 3D information of the target anatomy.

In accordance with some embodiments of the present invention a medical imaging method is provided that allows for additional flexibility in adjusting positions of the imaging system during a procedure. Furthermore, some embodiments provided a medical imaging method that allows for retention of a contrast agent within a predetermined area during a transvascular or similar procedure. In some embodiments, the 3D information of the target anatomy may be provided using a 2D imaging technique. In some such embodiments, multiple instances of the 2D imaging technique is used in order to provide the 3D information of the target anatomy.

In one specific example of imaging technique utilizing a $CO_2$ portogram, as outlined herein above, $CO_2$ imaging is used with a Transjugular Intrahepatic Portosystemic Shunt (TIPS) Procedure that utilizes an assembly that provides steerability and an RF device. In some such examples, the physician is able to readily identify device orientation through the handle of the steerable sheath and no significant difference is observed in comparison to conventional tools in terms of handling. In a specific instance of this example, a method of using a dual plane $CO_2$ in combination with fluoroscopy may provide enhanced imaging guidance information than single plane fluoroscopy view. In such example, where $CO_2$, a gun-barrel view a gun-barrel view can be achieved in order to further facilitate the TIPS procedure to assist in imaging and guidance to aim the assembly at a target position within the portal vein.

As outlined herein, in some embodiments, a medical imaging method is disclosed that provides 3D information about a target anatomy. More specifically, a medical imaging method is disclosed that provides an imaging solution that generates a reference image of vasculature, such as the portal vein, under two different viewing planes using $CO_2$ digital subtraction angiography (DSA). The method provides the physician with 3D information of the anatomy for carrying out a transvascular procedure such as a Transjugular Intrahepatic Portosystemic Shunt (TIPS) procedure.

In some instances of the embodiments described herein above, the RF guidewire may be the PowerWire RF guidewire (Baylis Medical Company Inc.), the steerable sheath may be the SureFlex® steerable sheath, the VersaCross™ steerable sheath or the SupraCross™ steerable sheath (all by Baylis Medical Company Inc.), and the RF catheter may be the PowerCatheter™ RF catheter (Baylis Medical Company Inc.). Further embodiments of exemplary RF guidewires, steerable sheaths, and RF catheters that may be suitable for the methods described herein are described in greater detail in: U.S. application Ser. No. 12/926,292 and corresponding publication No. US 2011/0118735 A1, PCT application No. PCT/IB2013/055013 and corresponding publication No. WO 2013/190475 A2, PCT application No. PCT/IB2014/059696 and corresponding publication No. WO 2014/141105 A1, and PCT application No. PCT/IB2014/059830 with corresponding publication No. WO 2014/141197 A1, which are all incorporated herein by reference in their entirety. Alternatively, other guidewires, steerable sheaths and catheters maybe used for embodiments of methods and/or procedures as described herein above.

In accordance with one broad aspect, embodiments of the present invention provide a method of carrying out a TransVascular Intrahepatic procedure using a flexible system comprising, an RF catheter and an angled guiding catheter, the method for creating a pathway between vasculature comprising a hepatic vein and a portal vein, the method comprising the steps of: advancing the RF catheter into the hepatic vein; advancing the angled guiding catheter over the RF catheter; utilizing a 'gun-barrel' view from the portal vein to the hepatic vein under imaging such as fluoroscopy while steering the guiding catheter to direct the RF catheter towards the portal vein; delivering RF energy from the RF catheter to puncture through a hepatic vessel wall, the liver parenchyma and a portal vessel wall to access or enter the portal vein to form a tract from the hepatic vein to the portal vein; confirming access into the portal vein; dilating the tract in the liver; and advancing a sheath through the tract to support the placement of a supportive device; wherein the angled guiding catheter functions to guide and aim the RF catheter from within the hepatic vein towards the portal vein to aim the RF catheter towards the portal vein, and applying RF through the RF catheter to puncture through the liver parenchyma tissue for creating a channel between the hepatic and portal veins with minimal force using RF while minimizing damage to the vasculature and the liver tissue.

In accordance with another broad aspect, embodiments of the present invention provide a method of carrying out a TransJugular Intrahepatic Portosystemic shunt procedure using a flexible system comprising, the method comprising the steps of: gaining access to hepatic vein through the inferior vena cava with a guide wire and a catheter and removing the catheter; advancing a guiding catheter into the hepatic vein and placing the distal end of the guiding catheter at the desired puncture location in the hepatic vein, the sheath comprising one or more alignment markers and/or directional markers at the distal end; removing the guide wire; performing imaging at the hepatic vein to visualize the portal vein; advancing the RF catheter within the guiding catheter together through a 10 Fr sheath to the puncture location; steering the guiding catheter to aim towards the portal vein utilizing the directional markers and the alignment markers so that the angled section of the guiding catheter is pointing towards and perpendicular to the 'gun-barrel' viewing plane; While keeping the guiding catheter in this 'aiming' position, at step applying RF energy and advance the RF catheter towards the portal vein, creating a tract from the hepatic vein to the portal vein to create a shunt there-between; and confirming access into the portal vein by verifying that the tip of the RF catheter is within the portal vein outline under the 'gun-barrel' view; and removing the RF catheter and advancing a guidewire into the portal vein to facilitate the placement of a stent within the tract between the hepatic and portal veins; wherein the guiding catheter functions to guide and aim the RF catheter from within the hepatic vein towards the portal vein to aim the RF catheter towards the portal vein, and applying RF through the RF catheter to puncture through the liver parenchyma tissue for creating a channel between the hepatic and portal veins with minimal force using RF while minimizing damage to the vasculature and the liver tissue.

In some examples of these broad aspects, the guiding catheter is steerable to allow for in-situ angle adjustment of the guiding catheter to aim the RF catheter towards a selected position along the portal vein. In another example, the step of advancing the RF catheter in the guiding catheter through a 10 Fr sheath is replaced by the step of advancing a 10 Fr sheath over the guiding catheter after the step of confirming portal vein access.

In additional examples of these broad aspects, the step of imaging comprises: performing standard $CO_2$ angiography at the hepatic vein to visualize the portal vein; rotating the fluoro to the 'gun-barrel' view plane; and removing the $CO_2$ angiography devices. In an alternate example, the step of imaging may comprise utilizing an imaging technique comprise intravascular ultrasound (IVUS).

In still a further example of these broad aspects, the RF catheter is advanced in a single step to a desired distance or length. In other examples, the RF catheter is advanced in several discrete steps under the application of RF while confirming a trajectory under imaging.

In still a further broad aspect, embodiments of the present invention provide a method of carrying out a TransJugular Intrahepatic Portosystemic shunt procedure using a flexible telescoping assembly comprising an RF guidewire, a crossing catheter, a flexible dilator, a steerable sheath and an introducer sheath in a telescoping arrangement, the method for creating a pathway between vasculature comprising a hepatic vein and a portal vein, the method comprising the steps of: gaining access to the hepatic vein; advancing the telescoped assembly into the hepatic vein; Under imaging, using the steerable sheath to aim the telescoped assembly in-situ from within the hepatic vein towards the portal vein to orient the RF guidewire towards the portal vein; delivering RF and advancing the RF guidewire through the liver parenchyma to permit controlled advancement of the RF guidewire towards the portal vein target, the RF guidewire enabling puncturing through the liver parenchyma and a vessel wall of the portal vein; confirming portal vein access; advancing the telescoped assembly into the portal vein and removing all devices except the introducer sheath for deploying a stent there-through; wherein the telescoping assembly allows for creation of an artificial channel between the hepatic and portal veins by enabling the steerable sheath to aim the assembly including the RF guidewire towards the target site within the portal vein, and wherein the system enables the RF guidewire to puncture through a hepatic vein wall, the liver parenchyma, and the portal vein wall with minimal force using RF while minimizing damage to the vasculature and the liver tissue and minimizing the need for device exchanges.

In still a further broad aspect, embodiments of the present invention provide a method for treating portal hypertension using a Transjugular Intrahepatic Portosystemic procedure using an RF guidewire and a steerable sheath to create a pathway between a portal vein and a hepatic vein, the method comprising: gaining access to hepatic vein with a guidewire and catheter via inferior vena cava and removing the catheter; advancing a steerable sheath and dilator over a guidewire into hepatic vein; removing the dilator and guidewire; visualizing the portal vein using imaging techniques; advancing an RF guidewire and a supporting catheter forming an RF guidewire catheter assembly to the tip of the steerable sheath; connecting the RF guidewire to an RF generator; using the steerable sheath to orient in-situ to aim towards the portal vein to provide a predictable trajectory to aim the RF guidewire towards target site within the portal vein; applying RF and advancing the RF guidewire through a wall of the hepatic vein and through the liver parenchyma to permit controlled advancement of the RF guidewire towards a target side within the portal vein; and advancing the supporting catheter over the RF guidewire; confirming portal vein access; and Upon confirmation of portal access, advancing the supporting catheter further into portal vein and inserting and advancing a guidewire into the portal vein to facilitate placement of a stent; wherein the steerable sheath enables the RF guidewire to be aimed towards the target site within the portal vein, and wherein the RF guidewire allows puncture through the hepatic vein wall, the liver parenchyma, and the portal vein wall with minimal force using RF while minimizing damage to the vasculature and the liver tissue and minimizing the need for device exchanges.

In one example of this broad aspect, the RF guidewire and the supporting catheter are coupled to one another. In another example of this broad aspect, the step of aiming comprises actuating the steerable sheath, to angle the tip of the steerable sheath towards the portal vein. In a specific example of this, the step of aiming the steerable sheath towards the portal vein comprises angling the steerable sheath towards a target within the portal vein.

In a further example of this broad aspect, the method further comprises a step of retracting the supporting catheter to the tip of the steerable sheath, if access to the portal vein has not been confirmed, and advancing the RF guidewire into the portal vein to complete the TIPS procedure.

In some examples of broad aspect outlined herein above, the step of visualizing the portal vein comprises inserting a target device into the portal vein to assist in visualizing the portal vein. In a specific example, the target device is taken from the group comprising of a guidewire, catheter or a snare.

In another example of this broad aspect, the method comprises: prior to the step of advancing the RF guidewire and the supporting catheter, building a locked RF guidewire and Catheter assembly using a locking mechanism to lock the RF guidewire and the supporting catheter. In one such example, the step of building a locked RF guidewire and Catheter assembly comprises: advancing the RF guidewire into a supporting catheter, wherein the supporting catheter is a crossing catheter, advancing the RF guidewire into the crossing catheter while ensuring that the tip of the RF guidewire is protruding by about 2-5 mm from the tip of the crossing catheter; and locking the position of the RF guidewire using a locking mechanism, to form an RF guidewire catheter assembly. In a specific instance of this example, the locking mechanism comprises a Tuohy-Borst mechanism.

In some example of this broad aspect, the crossing catheter is between about 5 fr to 6 Fr in size. In one such example, the RF guidewire is protruding by between about 2 mm to about 5 mm from the tip of the crossing catheter.

In another broad aspect, embodiments of the present invention provide a method for facilitating a Transjugular Intrahepatic Portosystemic Shunt Procedure by creating a pathway between a hepatic vein and a portal vein, using a telescoping assembly comprising a steerable guiding sheath, a flexible dilator, a crossing catheter and an RF guidewire are all received and arranged in the telescoping arrangement, the method comprising the steps of: advancing the telescoping assembly into the hepatic vein; steering the steerable sheath to aim the telescoping assembly in-situ along a desired trajectory from within the hepatic vein towards the portal vein to orient the RF guidewire towards a desired target site within the portal vein; applying RF and advancing the RF guidewire in a controlled manner from the hepatic vein through a hepatic vessel wall, the liver parenchyma, a portal vessel wall and into the portal vein; confirming portal vein access; after confirmation of the portal access, advancing the telescoping assembly into the portal vein; removing all devices except the introducer sheath and RF guidewire; and deploying a stent; wherein the telescoping assembly functions to aim the devices therein from within the hepatic vein towards the portal vein to aim the RF guidewire towards the portal vein to provide a predictable trajectory, and enables creation of a channel between the hepatic and portal vein in a controlled manner using RF with application of minimal force and while minimizing damage to the vasculature and the liver tissue and while reducing the need for device exchanges.

In an example of this broad aspect, the telescoping assembly additionally comprises an introducer sheath, wherein the steerable sheath is received within the introducer sheath. In a specific instance of this example, the introducer sheath comprises a 10 Fr Introducer sheath, the steerable guiding comprises a 7 Fr Steerable Sheath, the flexible dilator comprises a 7 Fr flexible dilator, the crossing catheter comprises a 4 Fr crossing catheter and the RF guidewire comprises a 0.035" guidewire.

In another example of this broad aspect, the steerable sheath comprises a 10 Fr steerable sheath, the flexible dilator comprises a 10 Fr flexible dilator, the crossing catheter comprises a 4 Fr crossing catheter, and the RF guidewire comprises a 0.035" RF guidewire.

In some examples provided herein, the step of deploying a stent comprises deploying a GORE® VIATORR® TIPS Endo-prosthesis.

In still another broad aspect, embodiment of the present invention provide a method for facilitating Transjugular Intrahepatic Portosystemic Shunt (TIPS) procedure using an RF catheter and a steerable sheath to create a tract between a hepatic vein and a portal vein, the method comprising: gaining access to the hepatic vein with a guidewire and catheter via inferior vena cava and removing the catheter; advancing the steerable sheath and dilator over the guidewire into the hepatic vein; removing the dilator and wire; visualizing the target portal vein using imaging techniques; advancing the RF catheter to the tip of the steerable sheath; permitting in-situ aiming towards the portal vein target by actuating the steerable sheath towards the portal vein or the target within the portal vein; advancing the RF catheter through the steerable sheath to the puncture site; advancing the RF catheter through the liver parenchyma towards the portal vein or the target within the portal vein, the RF catheter enabling puncture through a wall of the hepatic vein, the liver parenchyma and a wall of the portal vein; Confirming portal vein access; and if the portal vein has been accessed, completing the TIPS procedure; wherein the steerable sheath functions to RF catheter from within the hepatic vein along a desired trajectory towards a desired target site within the portal vein, wherein the RF catheter enables creation of a channel between the hepatic and portal vein in a controlled manner using RF with application of minimal force and while minimizing damage to the vasculature and the liver tissue and while reducing the need for device exchanges.

In some examples of the above broad aspects, embodiments of the present invention provide a step of confirming portal access, wherein the step of confirming portal access comprises aspirating through a catheter (such as an RF catheter) and confirming if blood is withdrawn. In an alternate example, the step of confirming portal access comprises injecting contrast and observing the vessel under imaging. In still a further alternative, the step of confirming portal access comprises using tactile feedback.

In still another alternative, the step of confirming portal access may comprise inserting a target and assessing proximity to the target from the puncturing device. In a specific instance of this example, the target comprises a metal device that is inserted within the portal vein and using a 'metal contact' error from the RF generator as a confirmation feedback.

In some examples of the present invention, the RF device (the RF guidewire or the RF catheter) is advanced in a single step towards a desired target location within the portal vein. Alternatively, the RF device (the RF guidewire or the RF catheter) is advanced in several discrete steps towards the portal vein under the application of RF while confirming the trajectory under imaging.

In another broad aspect, embodiments of the present invention provide an RF catheter for carrying out a TransJugular Intrahepatic Portosystemic shunt procedure, the RF catheter comprising: a hypotube defining an inner lumen comparing a polymer insulation disposed thereon; an RF electrode forming an active RF tip at a distal end of the hypo-tube; and a side-port proximal to the distal end.

In an example of this broad aspect, the RF catheter comprises a laser-cut hypotube. In a specific instance of this example, the hypotube comprises a domed distal hypotube that is receivable within a proximal hypotube, the domed distal hypotube forming a domed RF electrode at the distal tip. In one particular example, the outer diameter of the RF catheter is equal to about 0.035"-0.038". In some instances of this example, the outer diameter of rigid distal hypotube is either equal to, or slightly greater than, the inner diameter of the flexible proximal hypotube.

In another broad aspect of the present invention, an RF guidewire catheter assembly or an RF catheter assembly is disclosed for facilitating a TransJugular Intrahepatic Portosystemic Shunt Procedure comprising: an RF guidewire, the RF guidewire comprising an insulated core-wire with an RF electrode at a distal tip, and a platinum band proximal to a heat shield positioned that is positioned proximally to the RF electrode, the RF guidewire comprising a connection means at a proximal end for connecting to an RF supply, RF guidewire being removable from the catheter upon disassembly; and a catheter having one or more side ports at its distal end and defining a distal tip; a body shaft of the core wire having an outer diameter that is smaller than a lumen of the catheter enabling injection and withdrawal of fluid through the side ports; and an outer diameter along the distal tip of the core wire being positioned with force fit engagement within with an inner diameter of the distal tip of the catheter; a locking mechanism to lock a position of the RF guidewire within the catheter.

In one instance of this example, the locking mechanism comprises a luer lock. In some such embodiments, the RF guidewire defines a curved distal tip. In one example of an RF guidewire catheter assembly, the RF guidewire defines a straight distal tip. In another example, the one or more sideports may comprise one or more openings. In still a further example of an RF catheter assembly, the one or more sideports may be taken from a group comprising of an oval sideport, a rectangular side ports, and a circular side port.

In another broad aspect of the present invention: an RF catheter assembly or an RF guidewire catheter assembly is disclosed for facilitating a TransJugular Portosystemic Shunt procedure, the assembly comprising: an RF guidewire, the RF guidewire comprising an insulated core-wire with an RF electrode at a distal tip, and a platinum band for supporting a heat shield positioned proximally to the RF electrode, the RF guidewire comprising a connection means at a proximal end for connecting to an RF supply, RF guidewire being removable from the catheter upon disassembly; and a tapered-lumen catheter defining a catheter lumen comprising a proximal lumen section and a distal lumen section, wherein the inner diameter of the proximal lumen section is greater than an inner diameter of distal lumen section, wherein the proximal lumen section tapers down along a taper to the distal lumen section to allow an RF guidewire to be positioned flush within the catheter along the distal lumen section.

In one particular example of this broad aspect, an RF catheter assembly is disclosed wherein the proximal lumen section is about 6-7 Fr in size and the distal lumen section is about 4 F r to about 5 Fr in size. In a specific example, of the RF catheter assembly, the distal lumen section is about 4 cm-8 cm in length.

In still another broad aspect, an RF catheter assembly for facilitating a TransJugular Portosystemic Shunt procedure is disclosed, the assembly comprising: an RF guidewire, the RF guidewire comprising an insulated core-wire with an RF electrode at a distal tip, and a platinum band for supporting a heat shield positioned proximally to the RF electrode, the RF guidewire comprising a connection means at a proximal end for connecting to an RF supply, RF guidewire being removable from the catheter upon disassembly; and a dual lumen catheter comprising a primary lumen for device exchange, and a secondary lumen for fluid flow. In one example of this broad aspect, the secondary lumen is open at its distal end to permit fluid flow. In one particular instance of this example, a junction between the primary lumen and the secondary lumen is internal to the catheter to permit an RF guidewire to be retracted proximal to the junction to allow for fluid flow and to prevent occlusion of the secondary lumen during device advancement.

In accordance with an embodiment of the present invention, a method is disclosed for performing a TIPS procedure using a flexible RF device and a steerable sheath, the method comprising: aiming the flexible RF device under imaging by actively steering the steerable sheath to orient the flexible RF device along a trajectory from one vessel to another vessel located at a distance from the first; and delivering RF energy using the flexible RF device to puncture through to the second vessel to advance the RF device in a controlled manner while minimizing the force required to puncture through to the second vessel.

In another broad aspect, embodiments of the present invention provide a method of performing a TIPS procedure using a flexible RF device and a steerable sheath forming a telescoping assembly, the method comprising: aiming the telescoping assembly under imaging by actively steering the steerable sheath to orient the flexible RF device along a trajectory from one vessel to another vessel located at a distance from the first; and delivering RF energy and advancing the flexible RF device in a controlled manner to puncture through the liver tissue to create a channel between the first vessel and the second vessel, wherein application of RF energy minimizes the force required to traverse through the liver tissue, minimizing the risk of damage to vasculature and the liver tissue while reducing the need for device exchanges by reducing the number of required device exchanges in order to complete the procedure.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of performing a TIPS procedure using a flexible radiofrequency (RF) guidewire, which is received within and moveable relative to a crossing catheter, which is received within and moveable relative to a flexible dilator, which is received within and moveable relative to a steerable sheath, forming a telescoping assembly, the method comprising:
   aiming the telescoping assembly under imaging by actively steering the steerable sheath to orient the flexible dilator and the flexible RF guidewire along a trajectory from a first vessel to a second vessel located at a distance from the first vessel;
   delivering RF energy using the flexible RF guidewire;
   advancing the flexible RF guidewire in a controlled manner to puncture through to the second vessel; and,
   advancing the steerable sheath, crossing catheter, and flexible dilator of the telescoping assembly into the second vessel, thereby creating a channel between the first and second vessel.

2. The method of claim 1, wherein the first vessel comprises a branch of a hepatic vein and the second vessel comprises a branch of a portal vein, wherein the step of aiming comprises actuating the steerable sheath, to aim the telescoping assembly from within the hepatic vein towards the portal vein.

3. The method of claim 2, wherein the step of aiming the telescoping assembly orients the flexible RF guidewire towards a target within the portal vein.

4. The method of claim 2, wherein the step of advancing the flexible RF guidewire comprises delivering the RF energy and puncturing through a vessel wall of the hepatic vein, a liver parenchyma and a first vessel wall of the portal vein while avoiding puncturing a second vessel wall of the portal vein.

5. The method of claim 1, wherein the step of aiming the telescoping assembly under imaging comprises visualizing the second vessel.

6. The method of claim 5, wherein visualizing the second vessel comprises:

performing CO₂ angiography at the first vessel to visualize the portal vein under a first viewing plane; and
rotating to a second viewing plane, the second viewing plane comprising a gun-barrel view plane;
wherein a reference image of the portal vein is provided under the two viewing planes using CO₂ digital subtraction angiography to provide 3D information of anatomy of the portal vein.

7. The method of claim 5, wherein the step of wherein visualizing the second vessel comprises using an imaging technique comprising an intravascular ultrasound (IVUS).

8. The method of claim 5, wherein the step of visualizing the second vessel comprises inserting a target device into the second vessel to assist in visualizing the second vessel.

9. The method of claim 1, additionally comprising a step of deploying a stent within the channel.

10. The method of claim 1, wherein the telescoping assembly additionally comprises an introducer sheath, wherein the steerable sheath is received within the introducer sheath.

11. The method of claim 1, additionally comprising a step of confirming access into the second vessel.

12. The method of claim 11, wherein the step of confirming access comprises a step selected from a group comprising: aspirating through the steerable sheath and confirming if blood is withdrawn, injecting contrast and observing the second vessel under imaging, and using tactile feedback to confirm access.

13. The method of claim 11, wherein the step of confirming access to the second vessel comprises inserting a target device proximate the second vessel and assessing proximity to the target device from the flexible RF guidewire.

14. The method of claim 13, wherein the target device that is inserted within the second vessel comprises a metal and wherein the step of confirming access comprises using a metal contact error from a RF generator as feedback of confirmation.

15. The method of claim 1, wherein the flexible RF guidewire is advanced in a single step to a desired distance or length.

16. The method of claim 1, wherein the flexible RF guidewire is advanced in two or more discrete steps under the delivery of the RF energy while confirming the trajectory under imaging.

17. The method of claim 10, additionally comprising a step of removing the steerable sheath, the crossing catheter, and the flexible dilator whereby the introducer sheath and flexible RF guidewire are used to facilitate delivery of a stent following the creation of the channel.

18. The method of claim 1, additionally comprising a step of removably coupling the crossing catheter and the flexible RF guidewire together to allow for concurrent advancement.

* * * * *